US009463010B2

(12) United States Patent
Gittings et al.

(10) Patent No.: US 9,463,010 B2
(45) Date of Patent: Oct. 11, 2016

(54) METHODS AND DEVICES TO TREAT DISEASED OR INJURED MUSCULOSKELETAL TISSUE

(71) Applicant: The Foundry, LLC, Menlo Park, CA (US)

(72) Inventors: Darin C. Gittings, Sunnyvale, CA (US); Mark Deem, Mountain View, CA (US); Michael Hendricksen, Redwood City, CA (US); Vivek Shenoy, Redwood City, CA (US); Hanson S. Gifford, III, Woodside, CA (US); Stephen Boyd, Murrieta, CA (US)

(73) Assignee: The Foundry, LLC, Menlo Park, CA (US)

( * ) Notice: Subject to any disclaimer, the term of this patent is extended or adjusted under 35 U.S.C. 154(b) by 652 days.

(21) Appl. No.: 13/749,038

(22) Filed: Jan. 24, 2013

(65) Prior Publication Data
US 2014/0031863 A1    Jan. 30, 2014

Related U.S. Application Data

(63) Continuation of application No. 12/776,177, filed on May 7, 2010, now abandoned.

(60) Provisional application No. 61/177,602, filed on May 12, 2009.

(51) Int. Cl.
*A61B 17/04* (2006.01)
*A61B 17/00* (2006.01)

(52) U.S. Cl.
CPC ........ *A61B 17/0401* (2013.01); *A61B 17/0466* (2013.01); *A61B 2017/00867* (2013.01);
(Continued)

(58) Field of Classification Search
CPC .................... A61B 17/0401; A61B 2017/0403–2017/0464; A61B 2017/0496
See application file for complete search history.

(56) References Cited

U.S. PATENT DOCUMENTS 3,939,969 A    2/1976    Miller et al.
3,981,307 A    9/1976    Borysko
(Continued)

FOREIGN PATENT DOCUMENTS

EP    1013229 A2    6/2000
EP    1588666 A2    10/2005
(Continued)

OTHER PUBLICATIONS

US 6,238,418, 05/2001, Schwartz et al. (withdrawn)
(Continued)

*Primary Examiner* — Julian W Woo
*Assistant Examiner* — Shaun L David
(74) *Attorney, Agent, or Firm* — Wilson Sonsini Goodrich & Rosati

(57) ABSTRACT

A knotless suture anchoring system includes an outer anchor having a central channel and a distal tip adapted to penetrate tissue. An inner anchor is positionable in the central channel of the outer anchor and a locking feature on one or both of the inner and outer anchors retains the inner anchor within the central channel. A continuous length of suture is coupled with the inner and outer suture anchors and has a free end. At least one of the inner and the outer anchors also has a cinching mechanism that allows the suture to be tensioned by passage of the suture through the cinching mechanism in a first direction while movement of the suture through the cinching mechanism in a second direction opposite the first direction is constrained.

13 Claims, 50 Drawing Sheets

(52) U.S. Cl.
CPC .... *A61B2017/044* (2013.01); *A61B 2017/045* (2013.01); *A61B 2017/0409* (2013.01); *A61B 2017/0414* (2013.01); *A61B 2017/0417* (2013.01); *A61B 2017/0422* (2013.01); *A61B 2017/0429* (2013.01); *A61B 2017/0446* (2013.01); *A61B 2017/0448* (2013.01); *A61B 2017/0451* (2013.01); *A61B 2017/0454* (2013.01); *A61B 2017/0459* (2013.01); *A61B 2017/0462* (2013.01); *A61B 2017/0496* (2013.01)

(56) References Cited

U.S. PATENT DOCUMENTS

| | | | |
|---|---|---|---|
| 4,249,656 A | 2/1981 | Cerwin et al. |
| 4,253,563 A | 3/1981 | Komarnycky |
| 4,406,363 A | 9/1983 | Aday |
| 4,412,614 A | 11/1983 | Ivanov |
| 4,413,727 A | 11/1983 | Cerwin et al. |
| 4,427,109 A | 1/1984 | Roshdy |
| 4,483,437 A | 11/1984 | Cerwin et al. |
| 4,491,218 A | 1/1985 | Aday |
| 4,533,041 A | 8/1985 | Aday et al. |
| 4,555,016 A | 11/1985 | Aday et al. |
| 4,572,363 A | 2/1986 | Alpern |
| 4,608,019 A | 8/1986 | Kumabe et al. |
| 4,615,435 A | 10/1986 | Alpern et al. |
| 4,750,492 A | 6/1988 | Jacobs |
| 4,884,681 A | 12/1989 | Roshdy et al. |
| 4,887,710 A | 12/1989 | Roshdy et al. |
| 4,898,156 A | 2/1990 | Gatturna et al. |
| 4,899,743 A | 2/1990 | Nicholson et al. |
| 4,904,272 A | 2/1990 | Middleton et al. |
| 4,946,043 A | 8/1990 | Roshdy et al. |
| 4,946,468 A | 8/1990 | Li |
| 4,968,315 A | 11/1990 | Gatturna |
| 4,969,892 A | 11/1990 | Burton et al. |
| 4,979,956 A | 12/1990 | Silvestrini |
| 5,002,550 A | 3/1991 | Li |
| 5,019,083 A | 5/1991 | Klapper et al. |
| 5,046,513 A | 9/1991 | Gatturna et al. |
| 5,057,112 A | 10/1991 | Sherman et al. |
| 5,061,283 A | 10/1991 | Silvestrini |
| 5,078,730 A | 1/1992 | Li et al. |
| 5,108,400 A | 4/1992 | Appel et al. |
| 5,152,790 A | 10/1992 | Rosenberg et al. |
| 5,171,251 A | 12/1992 | Bregen et al. |
| 5,174,087 A | 12/1992 | Bruno |
| 5,178,629 A | 1/1993 | Kammerer |
| 5,188,636 A | 2/1993 | Fedotov |
| 5,192,303 A | 3/1993 | Gatturna et al. |
| 5,201,656 A | 4/1993 | Sicurelli, Jr. |
| 5,207,679 A | 5/1993 | Li |
| 5,217,092 A | 6/1993 | Potter |
| 5,217,486 A | 6/1993 | Rice et al. |
| 5,242,457 A | 9/1993 | Akopov et al. |
| 5,258,016 A | 11/1993 | DiPoto et al. |
| 5,259,398 A | 11/1993 | Vrespa |
| 5,268,001 A | 12/1993 | Nicholson et al. |
| 5,282,809 A | 2/1994 | Kammerer et al. |
| 5,318,570 A | 6/1994 | Hood et al. |
| 5,336,240 A | 8/1994 | Metzler et al. |
| 5,352,230 A | 10/1994 | Hood |
| 5,358,511 A | 10/1994 | Gatturna et al. |
| 5,370,662 A | 12/1994 | Stone et al. |
| 5,380,334 A | 1/1995 | Torrie et al. |
| 5,383,905 A | 1/1995 | Golds et al. |
| 5,397,357 A | 3/1995 | Schmieding et al. |
| 5,407,420 A | 4/1995 | Bastyr et al. |
| 5,411,506 A | 5/1995 | Goble et al. |
| 5,411,523 A | 5/1995 | Goble |
| 5,415,651 A | 5/1995 | Schmieding |
| 5,417,691 A | 5/1995 | Hayhurst |
| 5,441,502 A | 8/1995 | Bartlett |
| 5,443,482 A | 8/1995 | Stone et al. |
| 5,454,815 A | 10/1995 | Geisser et al. |
| 5,464,425 A | 11/1995 | Skiba |
| 5,464,427 A | 11/1995 | Curtis et al. |
| 5,466,243 A | 11/1995 | Schmieding et al. |
| 5,480,403 A | 1/1996 | Lee et al. |
| 5,484,451 A | 1/1996 | Akopov et al. |
| 5,486,197 A | 1/1996 | Le et al. |
| 5,520,700 A | 5/1996 | Beyer et al. |
| 5,522,817 A | 6/1996 | Sander et al. |
| 5,522,843 A | 6/1996 | Zang |
| 5,522,844 A | 6/1996 | Johnson et al. |
| 5,527,342 A | 6/1996 | Pietrzak et al. |
| 5,540,718 A | 7/1996 | Barlett |
| 5,545,180 A | 8/1996 | Le et al. |
| 5,554,171 A | 9/1996 | Gatturna et al. |
| 5,569,306 A | 10/1996 | Thal |
| 5,571,139 A | 11/1996 | Jenkins, Jr. |
| 5,573,543 A | 11/1996 | Akopov et al. |
| 5,573,548 A | 11/1996 | Nazre et al. |
| 5,575,801 A | 11/1996 | Habermeyer et al. |
| 5,578,057 A | 11/1996 | Wenstrom, Jr. |
| 5,584,835 A | 12/1996 | Greenfield |
| 5,584,836 A | 12/1996 | Ballintyn et al. |
| 5,584,860 A | 12/1996 | Goble et al. |
| 5,591,207 A | 1/1997 | Coleman |
| 5,601,557 A | 2/1997 | Hayhurst |
| 5,618,314 A | 4/1997 | Harwin et al. |
| 5,626,587 A | 5/1997 | Bishop et al. |
| 5,626,612 A | 5/1997 | Barlett |
| 5,626,613 A | 5/1997 | Schmieding |
| 5,630,824 A | 5/1997 | Hart |
| 5,643,320 A | 7/1997 | Lower et al. |
| 5,643,321 A | 7/1997 | McDevitt |
| 5,647,874 A | 7/1997 | Hayhurst |
| 5,649,963 A | 7/1997 | McDevitt |
| 5,658,313 A | 8/1997 | Thal |
| 5,662,662 A | 9/1997 | Bishop et al. |
| 5,681,333 A | 10/1997 | Burkhart et al. |
| 5,683,401 A | 11/1997 | Schmieding et al. |
| 5,683,418 A | 11/1997 | Luscombe et al. |
| 5,683,419 A | 11/1997 | Thal |
| 5,690,676 A | 11/1997 | DiPoto et al. |
| 5,690,677 A | 11/1997 | Schmieding et al. |
| 5,702,397 A | 12/1997 | Goble et al. |
| 5,713,903 A | 2/1998 | Sander et al. |
| 5,720,753 A | 2/1998 | Sander et al. |
| 5,720,766 A | 2/1998 | Zang et al. |
| 5,725,529 A | 3/1998 | Nicholson et al. |
| 5,725,557 A | 3/1998 | Gatturna et al. |
| 5,728,100 A | 3/1998 | Skiba |
| 5,728,135 A | 3/1998 | Bregen et al. |
| 5,728,136 A | 3/1998 | Thal |
| 5,733,307 A | 3/1998 | Dinsdale |
| 5,769,894 A | 6/1998 | Ferragamo |
| 5,782,863 A | 7/1998 | Barlett |
| 5,782,864 A | 7/1998 | Lizardi |
| 5,782,865 A | 7/1998 | Grotz |
| 5,782,866 A | 7/1998 | Wenstrom, Jr. |
| 5,788,063 A | 8/1998 | Van Ness |
| 5,792,142 A | 8/1998 | Galitzer |
| 5,797,963 A | 8/1998 | McDevitt |
| 5,800,447 A | 9/1998 | Wenstrom, Jr. |
| 5,807,403 A | 9/1998 | Benderev et al. |
| 5,810,848 A | 9/1998 | Hayhurst |
| 5,814,051 A | 9/1998 | Wenstrom, Jr. |
| 5,814,070 A | 9/1998 | Borzone et al. |
| 5,814,071 A | 9/1998 | McDevitt et al. |
| 5,817,095 A | 10/1998 | Smith |
| 5,824,011 A | 10/1998 | Stone et al. |
| 5,842,478 A | 12/1998 | Benderev et al. |
| 5,843,087 A | 12/1998 | Jensen et al. |
| 5,851,219 A | 12/1998 | Goble et al. |
| 5,885,294 A | 3/1999 | Pedlick et al. |
| 5,894,921 A | 4/1999 | Le et al. |
| 5,899,920 A | 5/1999 | DeSatnick et al. |
| 5,904,704 A | 5/1999 | Goble et al. |
| 5,906,624 A | 5/1999 | Wenstrom, Jr. |
| RE36,289 E | 8/1999 | Le et al. |
| 5,935,129 A | 8/1999 | McDevitt et al. |

(56) References Cited

U.S. PATENT DOCUMENTS

| | | |
|---|---|---|
| 5,935,134 A | 8/1999 | Pedlick et al. |
| 5,938,686 A | 8/1999 | Benderev et al. |
| 5,941,882 A | 8/1999 | Jammet et al. |
| 5,944,724 A | 8/1999 | Lizardi |
| 5,944,739 A | 8/1999 | Zlock et al. |
| 5,948,000 A | 9/1999 | Larsen et al. |
| 5,948,001 A | 9/1999 | Larsen |
| 5,950,633 A | 9/1999 | Lynch et al. |
| 5,951,559 A | 9/1999 | Burkhart |
| 5,957,924 A | 9/1999 | Tormala et al. |
| 5,957,953 A | 9/1999 | DiPoto et al. |
| 5,961,538 A | 10/1999 | Pedlick et al. |
| 5,964,783 A | 10/1999 | Grafton et al. |
| 5,972,000 A | 10/1999 | Beyar et al. |
| 5,980,558 A | 11/1999 | Wiley |
| 5,993,451 A | 11/1999 | Burkhart |
| 5,993,458 A | 11/1999 | Vaitekunas et al. |
| 5,993,477 A | 11/1999 | Vaitekunas et al. |
| 6,007,566 A | 12/1999 | Wenstrom, Jr. |
| 6,019,768 A | 2/2000 | Wenstrom, Jr. et al. |
| 6,027,523 A | 2/2000 | Schmieding |
| 6,029,805 A | 2/2000 | Alpern et al. |
| 6,045,573 A | 4/2000 | Wenstrom, Jr. et al. |
| 6,045,574 A | 4/2000 | Thal |
| 6,066,160 A | 5/2000 | Colvin et al. |
| 6,080,154 A | 6/2000 | Reay-Young et al. |
| 6,086,608 A | 7/2000 | Ek et al. |
| 6,093,201 A | 7/2000 | Cooper et al. |
| 6,117,162 A | 9/2000 | Schmieding et al. |
| 6,146,406 A | 11/2000 | Shluzas et al. |
| 6,179,840 B1 | 1/2001 | Bowman |
| 6,183,479 B1 | 2/2001 | Tormala et al. |
| 6,190,401 B1 | 2/2001 | Green et al. |
| 6,214,031 B1 | 4/2001 | Schmieding et al. |
| 6,241,736 B1 | 6/2001 | Sater et al. |
| 6,264,676 B1 | 7/2001 | Gellman et al. |
| 6,267,718 B1 | 7/2001 | Vitali et al. |
| 6,270,518 B1 | 8/2001 | Pedlick et al. |
| 6,287,324 B1 | 9/2001 | Yarnitsky et al. |
| 6,293,961 B2 | 9/2001 | Schwartz et al. |
| 6,306,159 B1 | 10/2001 | Schwartz et al. |
| 6,319,252 B1 | 11/2001 | McDevitt et al. |
| 6,319,270 B1 | 11/2001 | Grafton et al. |
| 6,319,271 B1 | 11/2001 | Schwartz et al. |
| 6,319,272 B1 | 11/2001 | Brenneman et al. |
| 6,334,446 B1 | 1/2002 | Beyar |
| 6,338,765 B1 | 1/2002 | Statnikov |
| 6,368,350 B1 | 4/2002 | Erickson et al. |
| 6,387,113 B1 | 5/2002 | Hawkins et al. |
| 6,406,480 B1 | 6/2002 | Beyar et al. |
| 6,423,072 B1 | 7/2002 | Zappala |
| 6,461,373 B2 | 10/2002 | Wyman et al. |
| 6,500,169 B1 | 12/2002 | Deng |
| 6,511,499 B2 | 1/2003 | Schmieding et al. |
| 6,514,274 B1 | 2/2003 | Boucher et al. |
| 6,517,542 B1 | 2/2003 | Papay et al. |
| 6,520,980 B1 | 2/2003 | Foerster |
| 6,524,317 B1 | 2/2003 | Ritchart et al. |
| 6,527,794 B1 | 3/2003 | McDevitt et al. |
| 6,527,795 B1 | 3/2003 | Lizardi |
| 6,533,795 B1 | 3/2003 | Tran et al. |
| 6,544,281 B2 | 4/2003 | ElAttrache et al. |
| 6,551,330 B1 | 4/2003 | Bain et al. |
| 6,554,852 B1 | 4/2003 | Oberlander |
| 6,569,186 B1 | 5/2003 | Winters et al. |
| 6,569,188 B2 | 5/2003 | Grafton et al. |
| 6,575,984 B2 | 6/2003 | Beyar |
| 6,582,453 B1 | 6/2003 | Tran et al. |
| 6,585,730 B1 | 7/2003 | Foerster |
| 6,616,674 B2 | 9/2003 | Schmieding |
| 6,616,694 B1 | 9/2003 | Hart |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,561 B1 | 11/2003 | Tran |
| 6,652,562 B2 | 11/2003 | Collier et al. |
| 6,652,563 B2 | 11/2003 | Dreyfuss |
| 6,656,183 B2 | 12/2003 | Colleran et al. |
| 6,660,008 B1 | 12/2003 | Foerster et al. |
| 6,660,023 B2 | 12/2003 | McDevitt et al. |
| 6,673,094 B1 | 1/2004 | McDevitt et al. |
| 6,685,728 B2 | 2/2004 | Sinnott et al. |
| 6,689,153 B1 | 2/2004 | Skiba |
| 6,692,516 B2 | 2/2004 | West, Jr. et al. |
| 6,716,234 B2 | 4/2004 | Grafton et al. |
| 6,726,707 B2 | 4/2004 | Pedlick et al. |
| 6,743,233 B1 | 6/2004 | Baldwin et al. |
| 6,746,483 B1 | 6/2004 | Bojarski et al. |
| 6,767,037 B2 | 7/2004 | Wenstrom, Jr. |
| 6,770,073 B2 | 8/2004 | McDevitt et al. |
| 6,770,076 B2 | 8/2004 | Foerster |
| 6,773,436 B2 | 8/2004 | Donnelly et al. |
| 6,780,198 B1 | 8/2004 | Gregoire et al. |
| 6,830,572 B2 | 12/2004 | McDevitt et al. |
| 6,855,157 B2 | 2/2005 | Foerster et al. |
| 6,887,259 B2 | 5/2005 | Lizardi |
| 6,916,333 B2 | 7/2005 | Schmieding et al. |
| 6,932,834 B2 | 8/2005 | Lizardi et al. |
| 6,942,666 B2 | 9/2005 | Overaker et al. |
| 6,972,027 B2 | 12/2005 | Fallin et al. |
| 6,984,237 B2 | 1/2006 | Hatch et al. |
| 6,986,781 B2 | 1/2006 | Smith |
| 6,989,034 B2 | 1/2006 | Hamme et al. |
| 6,991,636 B2 | 1/2006 | Rose |
| 6,994,719 B2 | 2/2006 | Grafton |
| 7,022,129 B2 | 4/2006 | Overaker et al. |
| 7,029,490 B2 | 4/2006 | Grafton et al. |
| 7,033,380 B2 | 4/2006 | Schwartz et al. |
| 7,037,324 B2 | 5/2006 | Martinek |
| 7,052,499 B2 | 5/2006 | Steger et al. |
| 7,063,717 B2 | 6/2006 | St. Pierre et al. |
| 7,081,126 B2 | 7/2006 | McDevitt et al. |
| 7,083,638 B2 | 8/2006 | Foerster |
| 7,090,690 B2 | 8/2006 | Foerster et al. |
| 7,104,999 B2 | 9/2006 | Overaker |
| 7,131,973 B2 | 11/2006 | Hoffman |
| 7,144,414 B2 | 12/2006 | Harvie et al. |
| 7,144,415 B2 | 12/2006 | Del Rio et al. |
| 7,150,757 B2 | 12/2006 | Fallin et al. |
| 7,153,312 B1 | 12/2006 | Torrie et al. |
| 7,163,563 B2 | 1/2007 | Schwartz et al. |
| 7,195,634 B2 | 3/2007 | Schmieding et al. |
| 7,204,839 B2 | 4/2007 | Dreyfuss et al. |
| 7,217,279 B2 | 5/2007 | Reese |
| 7,226,469 B2 | 6/2007 | Benavitz et al. |
| 7,232,455 B2 | 6/2007 | Pedlick et al. |
| 7,235,100 B2 | 6/2007 | Martinek |
| 7,247,164 B1 | 7/2007 | Ritchart et al. |
| 7,250,057 B2 | 7/2007 | Forsberg et al. |
| 7,279,008 B2 | 10/2007 | Brown et al. |
| 7,300,451 B2 | 11/2007 | Crombie et al. |
| 7,309,337 B2 | 12/2007 | Colleran et al. |
| 7,309,346 B2 | 12/2007 | Martinek |
| 7,320,701 B2 | 1/2008 | Haut et al. |
| 7,329,272 B2 | 2/2008 | Burkhart et al. |
| 7,331,982 B1 | 2/2008 | Kaiser et al. |
| 7,335,221 B2 | 2/2008 | Collier et al. |
| RE40,237 E | 4/2008 | Bilotti et al. |
| 7,357,810 B2 | 4/2008 | Koyfman et al. |
| 7,361,195 B2 | 4/2008 | Schwartz et al. |
| 7,371,244 B2 | 5/2008 | Chatlynne et al. |
| 7,381,213 B2 | 6/2008 | Lizardi |
| 7,390,329 B2 | 6/2008 | Westra et al. |
| 7,390,332 B2 | 6/2008 | Selvitelli et al. |
| 7,407,512 B2 | 8/2008 | Bojarski et al. |
| 7,442,202 B2 | 10/2008 | Dreyfuss |
| 7,455,674 B2 | 11/2008 | Rose |
| 7,455,683 B2 | 11/2008 | Geissler et al. |
| 7,468,074 B2 | 12/2008 | Caborn et al. |
| 7,556,638 B2 | 7/2009 | Morgan et al. |
| 7,556,640 B2 | 7/2009 | Foerster |
| 7,566,339 B2 | 7/2009 | Fallin et al. |
| 7,572,275 B2 | 8/2009 | Fallin et al. |
| 7,572,283 B1 | 8/2009 | Meridew |

(56) References Cited

U.S. PATENT DOCUMENTS

| | | | |
|---|---|---|---|
| 7,585,311 B2 | 9/2009 | Green et al. | |
| 7,591,850 B2 | 9/2009 | Cavazzoni | |
| 7,601,165 B2 | 10/2009 | Stone | |
| 7,780,701 B1 | 8/2010 | Meridew et al. | |
| 7,874,839 B2 | 1/2011 | Bouneff | |
| 8,545,535 B2 | 10/2013 | Hirotsuka et al. | |
| 2001/0027321 A1 | 10/2001 | Gellman et al. | |
| 2002/0026187 A1 | 2/2002 | Swanson | |
| 2002/0111653 A1 | 8/2002 | Foerster | |
| 2002/0183762 A1 | 12/2002 | Anderson et al. | |
| 2003/0060835 A1 | 3/2003 | Wenstrom, Jr. | |
| 2003/0088272 A1 | 5/2003 | Smith | |
| 2003/0105474 A1 | 6/2003 | Bonutti | |
| 2003/0120309 A1 | 6/2003 | Colleran et al. | |
| 2003/0130694 A1 | 7/2003 | Bojarski et al. | |
| 2003/0135151 A1 | 7/2003 | Deng | |
| 2003/0195563 A1 | 10/2003 | Foerster et al. | |
| 2004/0002734 A1 | 1/2004 | Fallin et al. | |
| 2004/0030341 A1 | 2/2004 | Aeschlimann et al. | |
| 2004/0138706 A1 | 7/2004 | Abrams et al. | |
| 2004/0236373 A1 | 11/2004 | Anspach, III et al. | |
| 2005/0149122 A1 | 7/2005 | McDevitt et al. | |
| 2005/0240199 A1 | 10/2005 | Martinek et al. | |
| 2005/0245932 A1 | 11/2005 | Fanton et al. | |
| 2005/0251208 A1 | 11/2005 | Elmer et al. | |
| 2005/0283192 A1 | 12/2005 | Torrie et al. | |
| 2006/0100630 A1 | 5/2006 | West, Jr. | |
| 2006/0106422 A1 | 5/2006 | Del Rio et al. | |
| 2006/0106423 A1 | 5/2006 | Weisel et al. | |
| 2006/0149286 A1 | 7/2006 | Hoffman | |
| 2006/0282083 A1 | 12/2006 | Fanton et al. | |
| 2006/0293710 A1 | 12/2006 | Foerster et al. | |
| 2007/0088391 A1 | 4/2007 | McAlexander et al. | |
| 2007/0088412 A1 | 4/2007 | Ashman et al. | |
| 2007/0162022 A1 | 7/2007 | Zhang et al. | |
| 2007/0219557 A1 | 9/2007 | Bourque et al. | |
| 2007/0225719 A1 | 9/2007 | Stone et al. | |
| 2007/0255317 A1* | 11/2007 | Fanton | A61B 17/062 606/232 |
| 2007/0260259 A1 | 11/2007 | Fanton et al. | |
| 2008/0009904 A1 | 1/2008 | Bourque et al. | |
| 2008/0021474 A1 | 1/2008 | Bonutti et al. | |
| 2008/0027444 A1 | 1/2008 | Malek | |
| 2008/0054814 A1 | 3/2008 | Deppe et al. | |
| 2008/0058816 A1 | 3/2008 | Philippon et al. | |
| 2008/0086072 A1 | 4/2008 | Bonutti et al. | |
| 2008/0103528 A1 | 5/2008 | Zirps et al. | |
| 2008/0109080 A1 | 5/2008 | Aeschlimann et al. | |
| 2008/0147119 A1 | 6/2008 | Cauldwell et al. | |
| 2008/0188854 A1* | 8/2008 | Moser | A61B 17/0401 606/80 |
| 2008/0275469 A1 | 11/2008 | Fanton et al. | |
| 2008/0306510 A1 | 12/2008 | Stchur | |
| 2009/0012617 A1 | 1/2009 | White et al. | |
| 2009/0069845 A1* | 3/2009 | Frushell | A61B 17/0401 606/228 |
| 2009/0088798 A1 | 4/2009 | Snyder et al. | |
| 2009/0099598 A1 | 4/2009 | McDevitt et al. | |
| 2010/0016892 A1 | 1/2010 | Kaiser et al. | |
| 2010/0121355 A1 | 5/2010 | Gittings et al. | |
| 2010/0292731 A1 | 11/2010 | Gittings et al. | |
| 2010/0292732 A1 | 11/2010 | Hirotsuka et al. | |
| 2010/0292733 A1 | 11/2010 | Hendricksen et al. | |
| 2013/0345746 A1 | 12/2013 | Gittings et al. | |
| 2014/0005720 A1 | 1/2014 | Hirotsuka et al. | |
| 2014/0142627 A1 | 5/2014 | Hendricksen et al. | |
| 2015/0112384 A1 | 4/2015 | Hirotsuka et al. | |
| 2015/0320413 A1 | 11/2015 | Gittings et al. | |

FOREIGN PATENT DOCUMENTS

| | | |
|---|---|---|
| GB | 2084468 A | 4/1982 |
| WO | WO95/29637 A1 | 11/1995 |
| WO | WO97/30649 A1 | 8/1997 |
| WO | WO 03/096908 A2 | 11/2003 |
| WO | WO 03/096908 A3 | 4/2004 |
| WO | WO2006/037131 A2 | 4/2006 |
| WO | WO2006/039296 A2 | 4/2006 |
| WO | WO-2007078281 A2 | 7/2007 |
| WO | WO 2008/054814 A2 | 5/2008 |
| WO | WO 2008/054814 A3 | 6/2008 |
| WO | WO2008/109087 A1 | 9/2008 |
| WO | WO 2008/124206 A2 | 10/2008 |
| WO | WO 2008/124463 A2 | 10/2008 |
| WO | WO 2008/124206 A3 | 12/2008 |
| WO | WO 2009/023034 A1 | 2/2009 |
| WO | WO 2009/039513 A1 | 3/2009 |

OTHER PUBLICATIONS

Notice of allowance dated Aug. 2, 2013 for U.S. Appl. No. 12/776,208.
Office action dated Jun. 5, 2012 for U.S. Appl. No. 12/605,065.
Office action dated Jun. 18, 2013 for U.S. Appl. No. 12/776,208.
Office action dated Oct. 23, 2014 for U.S. Appl. No. 14/015,934.
U.S. Appl. No. 14/015,934, filed Aug. 30, 2013, Hirotsuka et al.
U.S. Appl. No. 13/692,596, filed Dec. 3, 2012, Gittings et al.
U.S. Appl. No. 13/855,445, filed Apr. 2, 2013, Hendricksen et al.
Ambrose et al., "Bioabsorbable Implants: Review of Clinical Experience in Orthopedic Surgery," Annals of Biomedical Engineering, Jan. 2004; 32(1):171-177.
Arthrex, Inc., 2.5 mm PushLock® Knotless Suture Anchor [brochure], 2007, 2 pages total.
Arthrex, Inc., "4.5 mm/6.7 mm Low Profile Screw System Surgical Technique" [brochure], 2009, 6 pages total.
Arthrex, Inc., "Acetabular Labral Repair Using the Bio-SutureTak® Suture Anchor System Surgical Technique" [brochure], 2007, 6 pages total.
Arthrex, Inc., "Achilles SutureBridgeTM Surgical Technique" [brochure], 2009, 6 pages total.
Arthrex, Inc., "ACL Graft Tensioning using the Suture Tensioner with Tensionmeter Surgical Technique" [brochure], 2009, 6 pages total.
Arthrex, Inc., "AdapteurTM Power System II" [brochure], 2008, 12 pages total.
Arthrex, Inc., "Advanced Technology" [brochure], 2008, 15 pages total.
Arthrex, Inc., "All-Inside BTB ACL RetroConstructionTM with Bone-Tendon-Bone Grafts Surgical Technique" [brochure], 2007, 8 pages total.
Arthrex, Inc., "Arthrex 300 Power System—Small Bone" [brochure], undated, 2 pages total.
Arthrex, Inc., "Arthrex 600 Power System—Small Bone" [brochure], undated, 2 pages total.
Arthrex, Inc., "Arthrex ACPTM Double Syringe System" [brochure], 2009, 6 pages total.
Arthrex, Inc., "Arthrex Bio-Composite Suture Anchors", p. 9 of 510(k) Summary, FDA Approval Letter and Indications of Use for 510(k) No. K082810, Jan. 2009, 6 pages total.
Arthrex, Inc., "Arthrex Flatfoot Solutions"[brochure], 2008, 2 pages total.
Arthrex, Inc., "Arthrex Hallux Valgus Solutions"[brochure], 2008, 2 pages total.
Arthrex, Inc., "Arthrex PushLock, Tak, and Corkscrew Products", p. 12 of 510(k) Summary, FDA Approval Letter and Indications of Use for 510(k) No. K061863, Oct. 2006, 6 pages total.
Arthrex, Inc., "Arthroscopic Meniscal Repair: Arthroscopic All-Inside Meniscal Repair with the Mensical ViperTM and DarkstickTM Surgical Technique" [brochure], 2006, 6 pages total.
Arthrex, Inc., "Arthroscopic Rotator Cuff Repair: Bio-Corkscrew® Suture Anchor Rotator Cuff Repair Surgical Technique" [brochure], 2007, 6 pages total.
Arthrex, Inc., "Arthroscopy Instruments" [brochure], 2008, 12 pages total.
Arthrex, Inc., "Beach Chair Lateral Traction Device Assembly Instructions" [instructions for use], 2006, 2 pages total.

(56) References Cited

OTHER PUBLICATIONS

Arthrex, Inc., "BioComposite SutureTak, BioComposite Corkscrew FT and BioComposite PushLock: An In Vitro Degradation Study" [white paper], Arthrex Research and Development, 2009, 1 page.

Arthrex, Inc., "BioCompositeTM Interference Screws for ACL and PCL Reconstruction," Arthrex Research and Development, 2008, 5 pages total.

Arthrex, Inc., "BioCompositeTM Interference Screws: A Stronger Turn in ACL/PCL Reconstruction," 2008, 56 pages total.

Arthrex, Inc., "Bio-Compression Screw System" [brochure], 2008, 6 pages total.

Arthrex, Inc., "Bio-FASTak® Bankart Repair Surgical Technique" [brochure], 2007, 6 pages total.

Arthrex, Inc., "Biomechanical Testing Comparison of Cayenne Medical and Arthrex, Inc. Repair Products" [white paper], Arthrex Research and Development, 2009, 1 page total.

Arthrex, Inc., "Bio-PostTM and Washer System" [brochure], 2001, 2 pages total.

Arthrex, Inc., "Bio-SutureTak Suture Anchor" [brochure], 2006, 2 pages total.

Arthrex, Inc., "Bio-TenodesisTM Screw System" [brochure], 2008, 6 pages total.

Arthrex, Inc., "Bone, Tendon or Ligament Repair?" [brochure], 2004, 1 page total.

Arthrex, Inc., "ClearCut Burrs" [brochure], 2006, 2 pages total.

Arthrex, Inc., "Comprehensive Solutions for Forefoot and Midfoot Surgery using the Mini TightRope® System—Five Surgical Techniques" [brochure], 2008, 13 pages total.

Arthrex, Inc., "CoolCut Series: Shaver Blades and Burrs" [brochure], 2009, 4 pages total.

Arthrex, Inc., "Double Row Rotator Cuff Repair using the Bio-Corkscrew® FT Surgical Technique" [brochure], 2007, 6 pages total.

Arthrex, Inc., "Elbow/Ankle Arthroscopy Instrument Set" [brochure], 2007, 8 pages total.

Arthrex, Inc., "Endoscopic Carpal Tunnel Release System" [brochure], 2000, 2 pages total.

Arthrex, Inc., "FiberWire® Braided Composite Suture" [brochure], 2008, 8 pages total.

Arthrex, Inc., "FiberWire® Collective Summary of Strength and Biocompatibility Testing Data Comparisons of Polyester and Polyblend Sutures" [white paper], 2006, 4 pages total.

Arthrex, Inc., "FiberWire® Confidence After Closure" [brochure], 2008, 6 pages total.

Arthrex, Inc., "FiberWire® Orthopaedic Composite Suture" [sell sheet], 2007, 2 pages total.

Arthrex, Inc., "FlipCutter ACL Reconstruction™: ACL Reconstruction using the FlipCutterTM and the Constant Femoral Guide Surgical Technique" [brochure], 2008, 6 pages total.

Arthrex, Inc., "FlipCutterTM" [brochure], 2009, 2 pages total.

Arthrex, Inc., "Freedom in Anatomic Femoral Socket Placement" [brochure], 2009, 2 pages total.

Arthrex, Inc., "Fulfilling the Need for Precision and Speed Rotator Cuff Repair" [brochure], 2009, 12 pages total.

Arthrex, Inc., "Innovative Solutions for Hip Arthroscopy" [brochure], 2008, 16 pages total.

Arthrex, Inc., "Knotless Rotator Cuff Repair: SpeedBridgeTM and SpeedFixTM Knotless Rotator Cuff Repair using the SwiveLockTM C and FiberTape® Surgical Technique" [brochure], 2008, 8 pages total.

Arthrex, Inc., "Knotless SingleRow Rotator Cuff Repair using the PushLockTM and FiberTape® Surgical Technique" [brochure], 2007, 4 pages total.

Arthrex, Inc., "MultiFire Scorpion™ Independently Pass Two FiberWire® Suture Tails Through Tissue Without Scorpion Removal" [brochure], 2009, 4 pages total.

Arthrex, Inc., "Next Generation in Knee Ligament Reconstruction & Repair Technology" [brochure], 2009, 42 pages total.

Arthrex, Inc., "Orthopaedic Procedure Electrosurgical System (ORES®)" [brochure], 2008, 11 pages total.

Arthrex, Inc., "OSferion: Porous Trapezoid 6-TCP Synthetic Grafting of BTB Autograft Harvest Sites" [brochure], 2008, 18 pages total.

Arthrex, Inc., "OSferion: Porous Trapezoid 6-TCP Synthetic Wedge Grafting of Tibial and Femoral Opening Wedge Osteotomy Sites" [brochure], 2009, 6 pages total.

Arthrex, Inc., "Percutaneous Glenohumeral Repair with SutureTak® Implants" [brochure], 2009, 2 pages total.

Arthrex, Inc., "ProStop® and ProStop® Plus for Correction of Posterior Tibial Tendon Dysfunction," [brochure], 2009, 6 pages total.

Arthrex, Inc., "ProWickTM Knee Postoperative and Cold Therapy Dressing System" [brochure], 2009, 4 pages total.

Arthrex, Inc., "ProWickTM Shoulder Postoperative and Cold Therapy Dressing System" [brochure], 2009, 4 pages total.

Arthrex, Inc., "Pull Out Strength of a 3.5 mm Bio-PushLock (AR-1926B)" [white paper], Arthrex Research and Development Nov. 10, 2005, 1 page total.

Arthrex, Inc., "PushLock® Bankart & SLAP Repair: PushLock® Knotless Anchor for Bankart & SLAP Repair Surgical Technique" [brochure], 2009, 8 pages total.

Arthrex, Inc., "PushLock® Knotless Instability Repair" [brochure], 2009, 12 pages total.

Arthrex, Inc., "PushLock®" [advertisement], 2008, 1 page total.

Arthrex, Inc., PushLockTM [directions for use], DFU-0099, Revision 8, 2 page total.

Arthrex, Inc., "Raising the Bar in Arthroscopic Imaging and Resection Technology" [brochure], 2009, 8 pages total.

Arthrex, Inc., "RetroConstruction™ Minimally Invasive Options for Anatomic ACL/PCL Reconstruction" [brochure], 2009, 11 pages total.

Arthrex, Inc., "Scorpion—Fulfilling the Need for Precision and Speed in Arthroscopic Rotator Cuff Repair" [brochure], 2008, 6 pages total.

Arthrex, Inc., "Shaver Blades and Burrs" [brochure], 2005, 1 page total.

Arthrex, Inc., "Single Use Disposable Shaver Blades and Burrs" [brochure], 2008, 2 pages total.

Arthrex, Inc., "Small Joint: Fracture—Fusion—Osteotomy Fixation Options" [brochure], 2007, 2 pages total.

Arthrex, Inc., "SutureLasso™ SD Products Reference Guide" [brochure], 2007, 1 page total.

Arthrex, Inc., "SutureTakTm Suture Anchors" [directions for use], DFU-0069, Revision 10, 2 page total.

Arthrex, Inc., "SwiveLockTM & FiberChain™ Knotless Rotator Cuff Repair Surgical Technique" [brochure], 2007, 8 pages total.

Arthrex, Inc., "Thumb UCL Repair/Reconstruction: 2.5 mm PushLock®/3 mm×8 mm BioTenodesisTM Thumb Collateral Ligament Repair/Reconstruction" [brochure], 2008, 8 pagest total.

Arthrex, Inc., "Transtibial ACL Reconstruction with Soft Tissue Grafts Surgical Technique" [brochure], 2007, 5 pages total.

Arthrex, Inc., "Trim-It Drill Pin™ The Need to Remove Hardware is Disappearing" [brochure], 2009, 2 pages total.

Arthrex, Inc., "Trim-It Drill Pin® Osteotomy Fixation Kit" [brochure], 2009, 6 pages total.

Arthrex, Inc., "Trim-ItTm Screw System" [brochure], 2006, 6 pages total.

Arthrex, Inc., "V-TakTm Soft Tissue Anchor" [brochure], 2006, 6 pages total.

Arthrex, Inc., "Wishbone™ Series Arthroscopy Instruments" [brochure], 2008, 8 pages total.

Arthrex, Inc., In Arthroscopic Surgery, You Can't Treat It If You Can't Reach It[brochure], 2007, 12 pages total.

Arthrex, Inc., New Materials in Sports Medicine [white paper], 2006, 7 pages total.

Arthrex, Inc., The Arthrex Chondral DartTM [brochure], 2006, 4 pages total.

Arthrex, Inc., The Continuous Wave III Arthroscopy Pump: Clear Vision in Arthroscopic Fluid Management [brochure], 2006, 12 pages total.

Arthrex, Inc., The Fully Threaded Family of Soft Tissue Repair Anchors: Cortical Cancellous Fixation with Fiberwire® Composite Suture for Superior Repair Strength [brochure], 2008, 6 pages total.

(56) References Cited

OTHER PUBLICATIONS

Arthrex, Inc., The Next Generation in Foot and Ankle Repair Technology [brochure], 2009, 44 pages total.
Arthrex, Inc., The Next Generation in Hand, Wrist and Elbow Repair Technology [brochure], 2009, 28 pages total.
Arthrex, Inc., The Next Generation in Shoulder Repair Technology [brochure], 2008, 24 pages total.
Arthrex, Inc., The Next Generation in Shoulder Repair Technology [brochure], 2009, 26 pages total.
Arthrex, Inc., The OATS® Sterile, Single Use Kit [brochure], 2007, 2 pages total.
Arthrex. Acetabular Labral Repair [brochure], Arthrex, Inc., 2007, 6 pages total; retrieved from the Internet: <http://arthromed.org/pdf/hip/Surgical%20Techniques/Acetabular%20Labral%20Repair%2Ousing%20the%20PushLock%20Knotless%20Anchor%20System.pdf>.
Arthrex. Bio-Corkscrew Anchor FT and Corkscrew FT II Suture Anchors [brochure], Arthrex, Inc., 2005, 6 pages total; retrieved from the Internet: <http://www.rcsed.ac.uk/fellows/Ivanrensburg/classification/surgtech/arthrex/arthrex%20man uals/biocorkscrew.pdf>.
Arthrex. Bio-SutureTak Bankart & SLAP Repair [brochure], Arthrex, Inc., 2007, 6 pages total; retrieved from the Internet: <http://depts.washington.edu/shoulder/Surgery/ArthroscopicTechniques/Arthrex/Bio-SutureTak-SLAP-Bankart-Repair.pdf>.
Arthrocare Corporation, "LabraLock P Knotless Implant w/Inserter Handle" [website], 1 page; retrieved: <http://www.arthrocaresportsmedicine.com/products/view/430>.
Arthrocare Corporation, "Magnum® MP Suture Implant" [brochure], 2009, 2 pages total.
Arthrocare Corporation, "Mini Magnum Knotless Implant w/Inserter Handle" [website], 1 page; retrieved: <http://www.arthrocaresportsmedicine.com/products/view/429>.
Arthrocare Corporation, "Mini Magnum® Knotless Fixation Implant" [brochure], 2009, 2 pages total.
Arthrocare Corporation, "SpeedScrewTM Fully Threaded OPUS® Knotless Fixation Implant" [brochure], 2009, 2 pages total.
Arthrocare Corporation, The OPUS® AutoCuff System Featuring SpeedScrew for Rotator Cuff Repair Technical Guide [brochure], 2009, 8 pages total.
Arthrocare Corporation, The OPUS® AutoCuff System for Rotator Cuff Repair Technical Guide [brochure], 2008, 8 pages total.
Arthrocare. OPUS LabraFix Knotless System [brochure], ArthroCare Corporation, 2008, A1027 Rev D, 6 pages total; retrieved: <http://www.arthrocaresportsmedicine.com/files/datasheets/A1027D.pdf>.
ARTHROTEK®. Charlotte™ Shoulder System: Arthroscopic Bankart Lesion Repair Using the 3.5 mm LactoScrew Suture Anchor [brochure], a Biomet Company. 2006, 4 pages total.
ARTHROTEK®. MicroMax˜fly Resorbable Suture Anchor [brochure], a Biomet Company. 2006, 8 pages total.
ARTHROTEK®. Charlotte™ Shoulder System [brochure], a Biomet Company. 2006, 16 pages total.
ARTHROTEK®. CharlotteTM Shoulder System: SLAP Lesion Repair Using the 3.5 mm LactoScrew Suture Anchor [brochure], a Biomet Company. 2002, 4 pages total.
ARTHROTEK®. MaxBraidTM PE Suture [brochure], a Biomet Company. 2004, 2 pages total.
Barber et al., "Suture Anchors—Update 1999," Arthroscopy, Oct. 1999; 15(7):719-725.
Bardana et al, The Effect of Suture Anchor Design and Orientation on Suture Abrasion: An In Vitro Study, Arthroscopy, Mar. 2003; 19(3,):274-281.
Benthien et al., "Cyclic Loading Achilles Tendon Repairs: A Comparison of Polyester and Polyblend Suture," Foot Ankle Int. Jul. 2006;27(7):512-518.
Biomet Sports Medicine, Hitch Suture Anchor [brochure], 2008, 2 pages total.

Biomet Sports Medicine, MicroMax™ Flex Suture Anchor MicroMaxTM Resorbable Suture Anchor [brochure], 2009, 20 pages total.
Biomet Sports Medicine, MicroMaxTm Flex Suture Anchor [advertisement], 2009, 2 pages total.
Biomet Sports Medicine, The Material Difference: Options for Rotator Cuff Repair, Labral Repair and Suture Management [brochure], 2008, 12 pages total.
Biomet, Inc., MicroMax-rm Resorbable Suture Anchor [website], 1 page; retrieved from the Internet: <http://www.biomet.com/sportsMedicine/productDetail.cfm?category=23&subCategory=33& product=108.
Blokhuis et al., "Properties of Calcium Phosphate Ceramics in Relation to Their In Vivo Behavior," J Trauma. Jan. 2000;48(1):179-86.
Brady et al., "Arthroscopic Rotator Cuff Repair: Establishing the Footprint," Techniques in Shoulder & Elbow Surgery, Dec. 2005; 6(4):242-251.
Burkhart et al., "Loop Security as a Determinant of Tissue Fixation Security," Arthroscopy, Oct. 1998;14(7):773-776.
Burkhart et al., "SLAP Lesions in the Overhead Athlete," Operative Techniques in Sports Medicine, Jul. 2000; 8(3):213-220.
Burkhart, "Arthroscopic Repair of Retracted Adhesed Rotator Cuff Tears and Subscapularis Tears: The Effective Use of Interval Slide Releases," Int J Shoulder Surg 2007; 1(1):39-44; retrieved from the internet: <http://www.internationalshoulderjournal.org/text.asp?2007/1/1/39/30677>.
Burkhart, "Arthroscopic Rotator Cuff Repair: Indications and Technique," Operative Techniques in Sports Medicine, Oct. 1997; 5(4):204-214.
Burkhart, "Knotless Self-Reinforcing Rotator Coff Repair with FiberChain-SwiveLock System" [video recording], ArthroCologne, 2nd International Symposium on Operative and Biologic Treatments in Sports Medicine, Cologne, Germany, Jun. 15-16, 2007; retrieved from thet Internet: <http://www.arthrocologne.com/SwiveLock-Rotator-Cuff¬ Repair.16361.html.
Burkhart, New Thoughts on SLAP Lesions, Arthroscopy and Arthroplasty of the Shoulder 15th Annual San Diego, 1998; pp. 351-355.
Bynum et al., "Failure Mode of Suture Anchors as a Function of Insertion Depth," Am J Sports Med Jul. 2005; 33(7):1030-1034.
C2M Medical, Inc., "CinchTM Knotless Fixation Implant System", pp. 63-65 of 510(k) Summary, FDA Approval Letter and Indications of Use for 510(k) No. K073226, Dec. 2007, 5 pages total.
Caborn et al., "A Biomechanical Comparison of Initial Soft Tissue Tibial Fixation Devices: The Intrafix Versus a Tapered 35-mm Bioabsorbable Interference Screw," Am J Sports Med, Jun. 2004; 32(4):956-961.
Chang et al., "Biomechanical Evaluation of Meniscal Repair Systems: A Comparison of the Meniscal Viper Repair System, the Vertical Mattress FasT-Fix Device, and Vertical Mattress Ethibond Sutures," Am J Sports Med, Dec. 2005; 33(12):1846-1852.
Chokshi et al., The effect of arthroscopic suture passing instruments on rotator cuff damage and repair strength, Bulletin of the NYU Hospital for Joint Diseases, Winter-Spring, 2006; 63(3/4):123-125; retrieved from the Internet: <http://www.nyuhjdbulletin.org/Mod/BulletinA/63N3-4/DocsA/63N3-4_11.pdf>.
ConMed Corporation, "Bio Mini-Revo® Anchor" [website], 1 page; retrieved from the Internet: <http://www.conmed.com/products_shoulder_biominirevo.php>.
ConMed Corporation,, "Bio Mini-Revo Suture Anchor", 510(k) Summary, FDA Approval Letter, FDA Approval Letter, and Indications of Use for 510(k) No. K073226, Jul. 2008, 5 pages total.
ConMed Linvatec, "Arthroscopy Product Catalog" [catalog], 2009, 194 pages total.
ConMed Linvatec, "Bio Mini-Revo™ Surgical Technique" [brochure] 2006, 12 pages total.
ConMed Linvatec, "Bio-Anchor® Shoulder Instability Repair System" [website], 2006, 1 page; retrieved from the Internet: <http://www.conmed.com/products_shoulder_bioanch.php>.

(56) References Cited

OTHER PUBLICATIONS

ConMed Linvatec, "Course: Bio Mini-Revo TM Surgical Technique—Designed in conjunction with Stephen J. Snyder, MD" [Slideshow] 2006, 26 pages; retrieved from the Internet: <http://www.conmed.com/SurgicalTechniques/BioMiniRevo.swf>.
ConMed Linvatec, "DuetTM Suture Anchor" [brochure], 2008, 4 pages total.
ConMed Linvatec, "Linvatec SRS Shoulder Restoration System: Simple Solutions for Complex Procedures" [website], 2009, 2 pages; retrieved from the Internet: <http://www.conmed.com/products_shoulder_srs_system.php?SelectCountry=0THER+COUNTRY.>.
ConMed Linvatec, "Paladin $^{TM}$ Rotator Cuff Anchor" [brochure], 2009, 2 pages total.
ConMed Linvatec, "Shoulder Restoration System" [brochure], 2009, 4 pages total.
ConMed Linvatec, "Shoulder Restoration System" [website], 2009, 1 page; retrieved from the Internet: <http://srs.linvatec.com/>.
ConMed Linvatec, "Shoulder Restoration System: PopLokTM Deployment Stages" [brochure], 2009, 2 pages total.
ConMed Linvatec, "Spectrum® II Soft Tissue Repair System" [brochure], 2006, 4 pages total.
ConMed Linvatec, "Spectrum® MVPTM" [brochure], 2008, 4 pages total.
ConMed Linvatec, "Super Shuttle™" [brochure], 2009, 2 pages total.
Covidien AG, "HerculonTM Soft Tissue Fixation System—Bringing greater pull-out strength to rotator cuff repair" [brochure], 2008, 4 pages total.
Daculsi et al., "Current State of the Art of Biphasic Calcium Phosphate Bioceramics," Journal of Materials Science, Mar. 2003; 14(3):195-200.
Depuy Mitek, Inc, a Johnson & Johnson Company, "Biocryl Rapide—TCP/PLGA Composite" [brochure], 2007, 4 pages total.
Depuy Mitek, Inc, a Johnson & Johnson Company, "BioKnotlessTM RC Suture Anchor: Rotator Cuff Repair Surgical Technique" [brochure], 2006, 6 pages total.
Depuy Mitek, Inc, a Johnson & Johnson Company, "Dual Threaded Suture Anchor Healix PEEKTM" [brochure], 2009, 2 pages total.
Depuy Mitek, Inc, a Johnson & Johnson Company, "ExpresSewTM Flexible Suture Passer" [instructions for use], Aug. 2007, 124 pages total.
Depuy Mitek, Inc, a Johnson & Johnson Company, "ExpresSewTM II Flexible Suture Passer" [instructions for use], Oct. 2006, 105 pages total.
Depuy Mitek, Inc, a Johnson & Johnson Company, "ExpresSewTM II: Surgical Technique" [brochure], 2007, 8 pages total.
Depuy Mitek, Inc, a Johnson & Johnson Company, "ExpresSewTM Surgical Technique" [brochure], 2005, 2 pages total.
Depuy Mitek, Inc, a Johnson & Johnson Company, "ExpresSewTM: A Single-Step Passer Under 5 mm" [brochure], 2005, 2 pages total.
Depuy Mitek, Inc, a Johnson & Johnson Company, "Healix BRTM" [brochure], 2009, 2 pages total.
Depuy Mitek, Inc, a Johnson & Johnson Company, "Healix PEEKTM—Dual Threaded Suture Anchor" [brochure], 2009, 2 pages total.
Depuy Mitek, Inc, a Johnson & Johnson Company, "Lupine$^{7}$" BR & BioknotlessTM BR Anchors . . . Now with Biocryl Rapide—BIOCRYL Rapide has refined our Suture Anchors as "Bio-Replaceable" [brochure], 2007, 4 pages total.
Depuy Mitek, Inc, a Johnson & Johnson Company, "Mitek Suture Grasper" [instructions for use], 2007, 60 pages total.
Depuy Mitek, Inc, a Johnson & Johnson Company, "Palenlok® RC—Quick Anchor Plus® Absorbable" [brochure] 2006, 2 pages total.
Depuy Mitek, Inc, a Johnson & Johnson Company, PathSeekerTM Flexible Suture Grasper [brochure], 2005, 2 pages total.
Depuy Mitek, Inc, a Johnson & Johnson Company, "PathSeekerTM Suture Passer" [instructions for use], 2007, 174 pages total.

Depuy Mitek, Inc, a Johnson & Johnson Company, Procedural Solutions in Shoulder Repair [advertorial and detail],2005; retrieved from the Internet: <http://issuu.com/valmaass/docs/mitek_advertorial?mode=a_p.
Depuy Mitek, Inc, a Johnson & Johnson Company, "Quick Anchor® Plus Family" [brochure], 2005, 2 pages total.
Depuy Mitek, Inc, a Johnson & Johnson Company, SpiraLokTM Absorbably Dual-Eyelet Theaded Suture Anchor [brochure], 2005, 2 pages total.
Depuy Mitek, Inc, a Johnson & Johnson Company, VersalokTM Anchor [instructions for use], Aug. 2007, 92 pages total.
Dines et al., "Horizontal Mattress With a Knotless Anchor to Better Recreate the Normal Superior Labrum Anatomy," Arthroscopy, Dec. 2008;24(12):1422-1425.
Esch, "Arthroscopic Rotator Cuff Repair with the Elite™ Shoulder System," A Smith & Nephew Techique Plus $^{T}$ Illustrated Guide, 2001, 16 pages total.
Ethicon, Inc., a Johnson & Johnson Company, Mitek® Products BioknotlessTM Anchors: The First Absorbable Knotless Suture Anchor [brochure], 2007, 2 pages total.
Ethicon, Inc., a Johnson & Johnson Company, Mitek® Products, "Absorbable Soft Anchor PANALOK®" [brochure] 2001, 2 pages; can be retrieved from the Internet: <www.shoulderdoc.co.uk/documents/mitek_panalok.pdf >.
Fox et al., "Update on Articular Cartilage Restoration," Techniques in Knee Surgery, Mar. 2003; 2(1):2-17.
Gartsman et al., "Arthroscopic Rotator Cuff Repair," Techniques in Shoulder and Elbow Surgery, 1999, pp. 1-7.
Gartsman, "Arthroscopic Repair of Full-Thickness Tears of the Rotator Cuff," The Journal of Bone and Joint Surgery, 1998; 80:832-840.
Gartsman, Shoulder Series Technique Guide: Bankart Repair Using the Smith & Nephew Bioraptor 2.9 Suture Anchor [brochure], Smith & Nephew, Inc., Sep. 2004, Rev. A, 7 pages total; retrieved from the Internet: <http://global.smith-nephew.com/cps/rde/xbcr/smithnephewls/V1-1061563A_bioraptorpdf.
Gill, The Treatment of Articular Cartilage Defects Using Microfracture and Debridement, Am J Knee Surg 2000;13(1):33-40.
Green et al., "Arthroscopic versus open Bankart procedures: a comparison of early morbidity and complications," Arthroscopy, 1993; 9(4):371-374.
Guanche et al., "Labral Repair" [video recording], A young track athlete with a pincer lesion in her hip undergoes an arthroscopic labral takedown and repair by Carlos Guanche, MD at Southern California Orthopedic institute in Van Nuys, CA. Dr. Guanche performs complex hip arthroscopic procedures including resection of cam lesions, labral repairs, psoas releases and abductor repairs, posted on the Internet: <http://www.youtube.com/watch?v=onCIESDRVZM&feature=channel_page> on Jun. 18, 2008.
Guanche, "Large Hip Labral Repair Using PushLockTM Anchor" [video recording], Arthroscopic surgery of a hip labral repair with a knotless anchor performed by Dr. Carlos Guanche in Van Nuys, CA, posted on the Internet: <http://www.youtube.com/watch?v=t04fj2TcXv0>on Mar. 25, 2008.
Halbrecht, "Versalok: A New technique for Arthroscopic Knotless Rotator Cuff Repair" [presentation], Mitek Sponsored Dinner Meeting. Tuscon AZ. Jun. 5, 2007; retrieved from the Internet: <http://www.iasm.com/pdfs/KnotlessArthroscopicRotatorCuffRepairUsingVersalok.pdf>, 44 pages total.
Hughes, The Kinematics and Kinetics of Slipknots for Arthroscopic Bankart Repair, Am J Sports Med, Nov. 2001; 29( 6):738-745.
International search report and written opinion dated Jul. 2, 2010 for PCT/US2010/034118.
International search report and written opinion dated Jul. 2, 2010 for PCT/US2010/034104.
International search report and written opinion dated Jul. 9, 2010 for PCT/US2010/034115.
Jeys et al., "Bone Anchors or Interference Screws? A Biomechanical Evaluation for Autograft Ankle Stabilization," Am J Sports Med, Oct. 2004; 32( 7):1651-1659.

(56) References Cited

OTHER PUBLICATIONS

KFX® Medical, Arthroscopic Double Row Rotator Cuff Repair [procedural Video], Performed by Joe Tauro, M.D., Toms River, NJ; can be view at: <http://www.kfxmedical.com/technology_procedu re. htm>.

KFX® Medical, "Arthroscopic PASTA lesion repair using the SutureCross® System" [procedural Video] Performed by Joe Tauro, M.D., Toms River, NJ; can be view at: <http://www.kfxmedical.com/technology_procedure_pasta_video.htm.

KFX® Medical, "SutureCross® Knotless Anatomic Fixation System: Double Row Fixation for Rotator Cuff Repair Animation" [video screenshots] 2008, 52 pages total.; video available online at <http://www.kfxmedical.com/video/SURGTECH9-23.wmv>.

KFX® Medical, "SutureCross® Knotless Anatomic Fixation System: Double Row Fixation Rotator Cuff Repair Surgical Technique" [brochure], 2008, 12 pages total.

KFX® Medical, "SutureCross® Knotless Anatomic Fixation System: Double Row Rotator Cuff Fixation" [website] ; retrieved from the Internet: <http://www.kfxmedical.com/product_suturecross.htm>, 1 page.

KFX® Medical, "SutureCross® Knotless Anatomic Fixation System: Rotator Cuff Repair" [datasheet], 2008, 2 pages total.

KFX® Medical, The PASTAFxTM System Surgical Technique: Simplified PASTA Rotator Cuff Repair [technique guide], 2008, 8 pages total.

KFX® Medical, The PASTAFxTM System: No need to Tear to Repair [website]; retrieved from the internet: <http://www.kfxmedical.com/product_pastafx.htm>, 2 pages total.

KFX® Medical, The PASTAFxTM System: Simplified PASTA Repair [datasheet] 2008, 2 pages total.

Khabie et al., "Fixation Strength of Suture Anchors After Intraoperative Failure of the First Anchor," 45th Annual Meeting of Orthopaedic Research Society, Feb. 1-4, 1999, Anaheim, p. 1074 ; retrieved from the Internet: <http://www.ors.org/web/Transactions/45/1074.PDF>.

Langdown et al., In Vivo Evaluation of 6-TCP Bone Graft Substitutes in a Bilateral Tabial Defect Model, Paper No. 1712, 52nd Annual Meeting of the Orthopaedic Research Society, The Lakeside Center, McCormick Place, Chicago, IL, Mar. 19-22, 2006, 1 page total.

Larson et al., "Arthroscopic Management of Femoroacetabular Impingement: Early Outcomes Measures," Arthroscopy. May 2008;24(5):540-546.

Linvatec, "Course: Bio-Anchor® Surgical Technique" [Slideshow], 2004, 13 pages; retrieved from the Internet: <http://www.conmed.com/SurgicalTechniques/BioAnchor.swf>.

Linvatec, a CONMED® Company, "Bio-Anchor® Surgical Technique: Shoulder Instability System" [brochure], 2004, 2 pages; retrieved from the Internet: <http://www. con med.com/PDF%20files/CST%203021%20Rev%201%20BioAnchorST.pdf.

Linvatec, a CONMED® Company, "ImpactTM Suture Anchor Surgical Technique" [brochure], 2004, 4 pages total.

Lo et al., "Abrasion Resistance of Two Types of Nonabsorbable Braided Suture," Arthroscopy, Apr. 2008; 20(4):407-413.

Lo et al., "Arthroscopic Knots: Determining the Optimal Balance of Loop Security and Knot Security," Arthroscopy. May 2004;20(5):489-502.

Louden et al., "Tendon Transfer Fixation in the Foot and Ankle: A Biomechnanical Study Evaluating Two Sizes of Pilot Holes for Bioabsorbable Screws," Foot & Ankle International, Jan. 2003; 24(1):67-72.

Ma et al., "Biomechanical Evaluation of Arthroscopic Rotator Cuff Stitches," The Journal of Bone and Joint Surgery, 2004; 86:1211-1216.

McGuire et al., "Bioabsorbable Interference Screws for Graft Fixation in Anterior Cruciate Ligament Reconstruction," Arthroscopy, Jul. 1999; 15(5):463-473.

Menche et al., "Inflammatory Foreign-Body Reaction to an Arthroscopic Bioabsorbable Meniscal Arrow Repair," Arthroscopy. Oct. 1999;15(7):770-772.

Meyer et al., "Mechanical Testing of Absorbable Suture Anchors," Arthroscopy, Feb. 2003; 19(2):188-193.

Middleton et al., "Synthetic Biodegradable Polymers as Orthopedic Devices," Biomaterials, Dec. 2000, 21(23):2335-2346.

Millett et al., "Mattress Double Anchor Footprint Repair: A Novel, Arthroscopic Rotator Cuff Repair Technique," Arthroscopy Oct. 2004; 20(8):875-879.

Morgan, "Arthroscopic Management of Rotator Cuff Tears" [Presentation Outline], The Morgan Kalman Clinic, Wilmington, Delaware, undated, 2 pages.

Murray, Jr., "Arthroscopic Rotator Cuff Repair with a Bioabsorbable Suture Anchor: Preliminary Results," [Abstract] Orthopaedic Associates of Portland, Portland, ME, 1 page.

Ogose et al., "Histological Assessment in Graft of Highly Purified Beta-Tricalcium Phosphate (Osferion) in Human Bones," Biomaterials. Mar. 2006;27(8):1542-1549.

Ogose et al., "Histological Examination of 6-Tricalcium Phosphate Graft in Human Femur," J Biomed Mater Res, 2002;63(5):601-604.

Parcus Medical, LLC, "Parcus V-LoxTM PEEK CF Suture Anchor", pp. 15, 16 of 510(k) Summary, FDA Approval Letter and Indications of Use for 510(k) No. K091094, Sep. 2009, 5 pages total.

Parcus Medical, LLC, "PEEK CF V-LoxTM Suture Anchor Demo" [video]; can be view at: <http://www.parcusmedical.com/techniques/animations/peek-vlox-anchor-demo.html>.

Parcus Medical, LLC, "V-LoxTM PEEK CF Suture Anchor [Production Information and Directions for use", undated, 2 pages total.

Parcus Medical, LLC, "V-LoxTM PEEK CF Suture Anchors Product Information Sheet" [brochure] undated, 1 page total.

Parcus Medical, LLC, "V-LoxTM PEEK CF Suture Anchors" [website]; retrieved from the Internet: <http://www.parcusmedical.com/products/peek-anchor.html>, 2 pages total.

Park et al., "Transosseous-Equivalent Rotator Cuff Repair Technique," Arthroscopy, Dec. 2006; 22(12):1360.e1-1360.e5.

Romeo et al., "Arthroscopic Repair of Full-Thickness Rotator Cuff Tears: Surgical Technique and Instrumentation" Orthopedic Special Edition, 2001; 7(1 of 2):25-30; retrieved from the Internet: <http://www.cartilagedoc.org/downloads/shoulder/Rotat.pdf>.

Schamblin, Conexa® Case Series Report: Arthroscopic Reinforcement of Revision Rotator Cuff Repair Tornier, Inc., 2009, 2 pages; retrieved from the Internet: <www.bhportho.com/docs/Conexa_RCR_Repair_Schamblin.pdf>.

Smith & Nephew, Inc., "2008 Product Catalog" [catalog], 2009, 311 pages total.

Smith & Nephew, Inc., "2009 Product Catalog" [catalog], 2008, 373 pages total.

Smith & Nephew, Inc., "ACCU-PASS Suture Shuttle" [video animation] 2005, 59 image screen shots; can be view at : <http://endo.smith-nephew.com/fr/View.asp?guid={6F27C42E-1632-4974-84E9-F18922FC19AA}&b=2-->.

Smith & Nephew, Inc., Bioraptor 2.9 Suture Anchor [video animation], 2004; can be viewed at: <http://endo.smith-nephew.com/fr/View.asp?guid={98BCCE86-B5C2-413F-80AE ¬CF7260A38C17}&b=2-BIORAPTOR%20animation. wmv>.

Smith & Nephew, Inc., "Bioraptor 2.9" [website], 3 pages total; retrieved from the Internet: <http://endo.smith-nephew.com/fr/node.asp?NodeId=3608>.

Smith & Nephew, Inc., "Bioraptor PK suture Anchor", 510(k) Summary, FDA Approval Letter, and Indications of Use for 510(k) No. K071586, Aug. 2007, 5 pages total.

Smith & Nephew, Inc., "ELITE PASS Premium Arthroscopic Suture Shuttle" [video animation], Mar. 2005, 44 image screen shots; video can be viewed at: <http://global.smith-nephew.com/us/showfile.xml?doc=V1-ELITE_PASS_Animation(26)_.wmv>.

Smith & Nephew, Inc., "FOOTPRINT PK Suture Anchor: Arthroscopic Shoulder Repair Using the Smith & Nephew FOOTPRINT PK Suture Anchor" [brochure], 2008, 12 pages total.

Smith & Nephew, Inc., "KINSA* Suture Achnor" [website], 2 pages; retrieved from the Internet: <http://www.endo.smith-nephew.com/fr/node.asp?NodeId=3739>.

Smith & Nephew, Inc., "OsteoraptorTM Suture Anchor", pp. 10-11 of 510(k) Summary, FDA Approval Letter, and Indications of Use for 510(k) No. K082215, Nov. 2008, 5 pages total.

(56) References Cited

OTHER PUBLICATIONS

Smith & Nephew, Inc., "TWINFIX Suture Anchors with ULTRABRAID Suture—Unparalleled strength, superior handling" [brochure], 2005, 12 pages total.
SmithNephew. Shoulder Series Technique Guide: Arthroscopic Shoulder Repair Using the Smith & Nephew Kinsa Suture Anchor [brochure], Smith & Nephew, Inc., Sep. 2006, Rev. B, 12 pages total; retrieved from the Internet: <http://global.smith-nephew.com/cps/rde/xbcr/smithnephewls/V1-10600180b%2829%29.pdf.
Spiralok and-Bio-Corkscrew FT Cadaver Study [white paper], no publication information, 2 pages total.
Stryker Corporation, "PEEK TwinLoop" [website], 1 page; retrieved from the Internet: <http://www.strykercom/enus/products/Orthopaedics/SportsMedicine/ShoulderInstrumentation/Anchors/Peek/056652.
Stryker Corporation, "Point to the Solution: BioZip Absorbable Suture Anchor" [brochure,] 2008, 4 pages total.
Stryker Corporation, "Shoulder Repair Made Simpler: Champion Shoulder Instrumentation" [brochure], 2008, 4 pages total.
Stryker Corporation, Strength & Flexibility in Soft-Tissue Repair [brochure], 2008, 4 pages total.
Stryker Corporation, Stronger Than Ever: PEEK Zip Anchor [brochure] 2008, 4 pages total.
Stryker Corporation, "Suture Sliding Made Simple" [brochure], 2005, 4 pages total.
Stryker Corporation, One Shot for Success—Titanium Wedge Anchor [brochure], 2008, 4 pages total.
Stryker. Stability, Precision, Flexibility—PEEK Twinloop Anchor [brochure], Stryker Corporation, Jun. 2008, Rev 1, 4 pages total; retrieved from the Internet: <http://www.strykercom/stellent/groups/public/documents/web_prod/056750.pdf>.
Tetik et al., "Bioabsorbable Interference Screw Fixation in a Bone Tunnel: Comparison of 28mm; 35 \mm Single Screw Fixation and Bi-Cortical Fixation with a 20mm and 17mm Screws," Lexington, Kentucky, undated, 3 pages total.
Tornier, Inc., "CINCHTM Knotless Fixation Implant System", pp. 38-40 of 510(k) Summary, FDA Approval Letter and Indications of Use for 510(k) No. K080335 , Feb. 2008, 6 pages total.
Tornier, Inc., "InsiteTM Suture Anchors", pp. 66-67 of 510(k) Summary, FDA Approval Letter and Indications of Use for 510(k) No. K080368, Feb. 2009, 5 pages total.
Tornier. Piton Knotless Fixation System, Tornier, Inc., 2009, 3 pages total; retrieved from the Internet: <http://www.tornier-us.com/sportsmed/smd003/index.php?pop=1> on Oct. 14, 2009.
Vogt et al., "Injuries to the Articular Cartilage," European Journal of Trauma, Aug. 2006; 32(4):325-331.
Walsh et al., "Healing of a Critical Size Defect in Sheep Using Bone Graft Substitutes in Block Form," Poster No. 1433, 53rd Annual Meeting of the Orthopaedic Research Society, San Diego Convention Center, San Diego, California, Feb. 11-14, 2007, 1 page total.
Warden et al., "Magnetic Resonance Imaging of Bioabsorbably Polylactic Acid Interference Screws During the First 2 Years After Anterior Cruciate Ligament Reconstruction," Arthroscopy, July-August, 15(5):474-480.
Weiler et al., "Biodegradable Implants in Sports Medicine: The Biological Base," Arthroscopy, Apr. 2000;16(3):305-321.
Yanke et al., 'Arthroscopic Double-Row and "Transosseous-Equivalent" Rotator Cuff Repair,' Am J Orthop (Belle Mead NJ). Jun. 2007;36(6):294-297.
Zimmer, Inc., "Labral Repair with Statak Suture Anchors—Surgical Techniques: Arthroscopic & Open" [brochure], 1996, 6 pages total.
Zimmer, Inc., "Rotator Cuff Repair with Statak Suture Anchors—Surgical Techniques: Arthroscopic & Open" [brochure], 1996, 6 pages total.
Office action dated Jun. 5, 2009 for U.S. Appl. No. 12/605,065.
Office action dated Oct. 4, 2012 for U.S. Appl. No. 12/776,225.
European search report and search opinion dated Apr. 2, 2015 for EP Application No. 10775303.0.
European search report and search opinion dated Apr. 20, 2015 for EP Application No. 10775304.8.
Office action dated Apr. 20, 2015 for U.S. Appl. No. 13/692,596.
U.S. Appl. No. 14/585,654, filed Dec. 30, 2014, Hirotsuka et al.
Office action dated Dec. 5, 2014 for U.S. Appl. No. 13/692,596.
Office action dated Dec. 4, 2015 for U.S. Appl. No. 13/855,445.
Co-pending U.S. Appl. No. 14/804,178, filed Jul. 20, 2015.
European search report and search opinion dated Apr. 15, 2016 for EP Application No. 10775301.4.

* cited by examiner

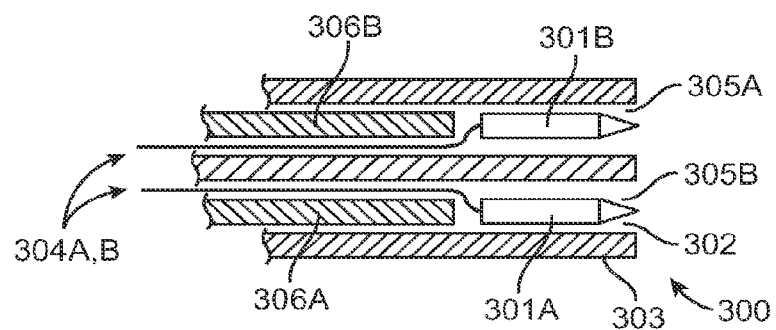
FIG. 8A
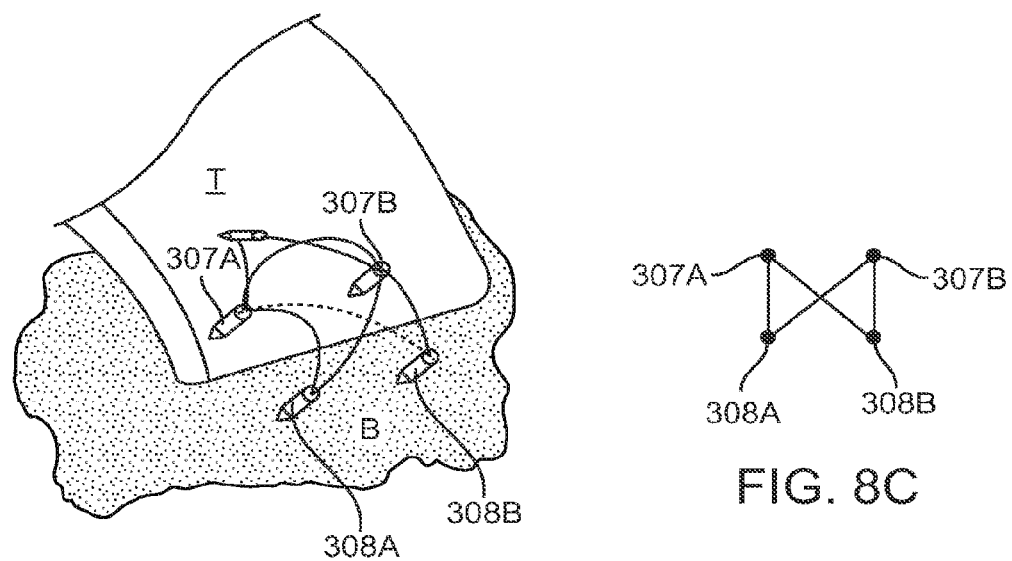
FIG. 8B
FIG. 8C

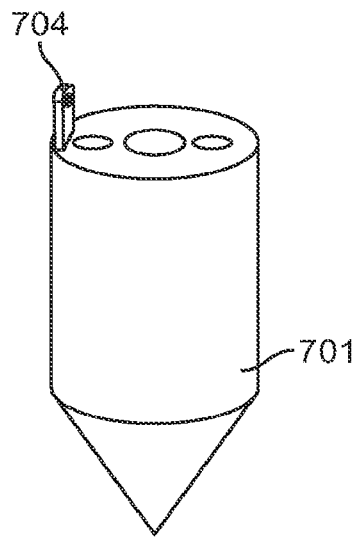
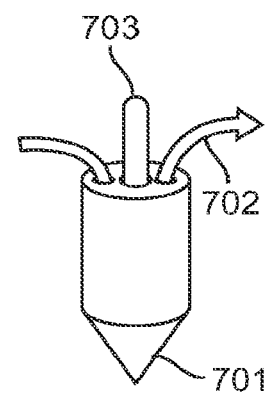
FIG. 12A    FIG. 12B
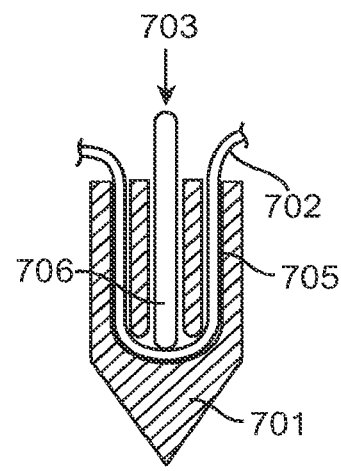
FIG. 12C

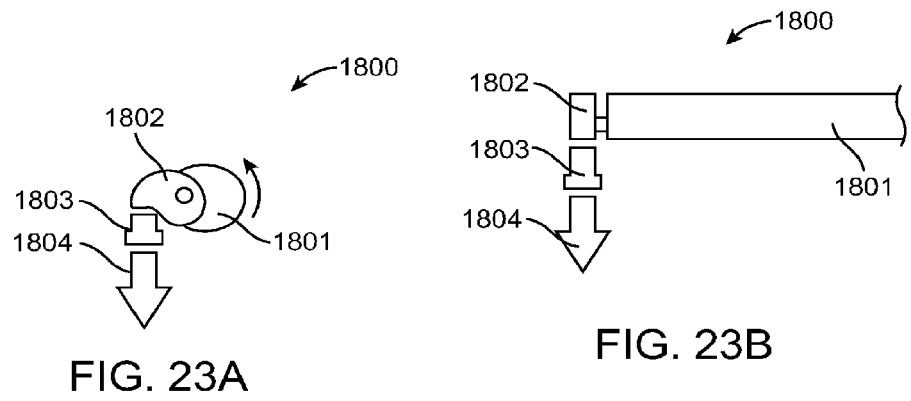
FIG. 23A
FIG. 23B
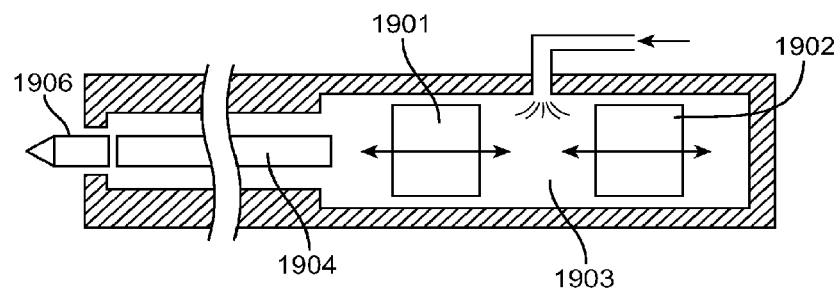
FIG. 24

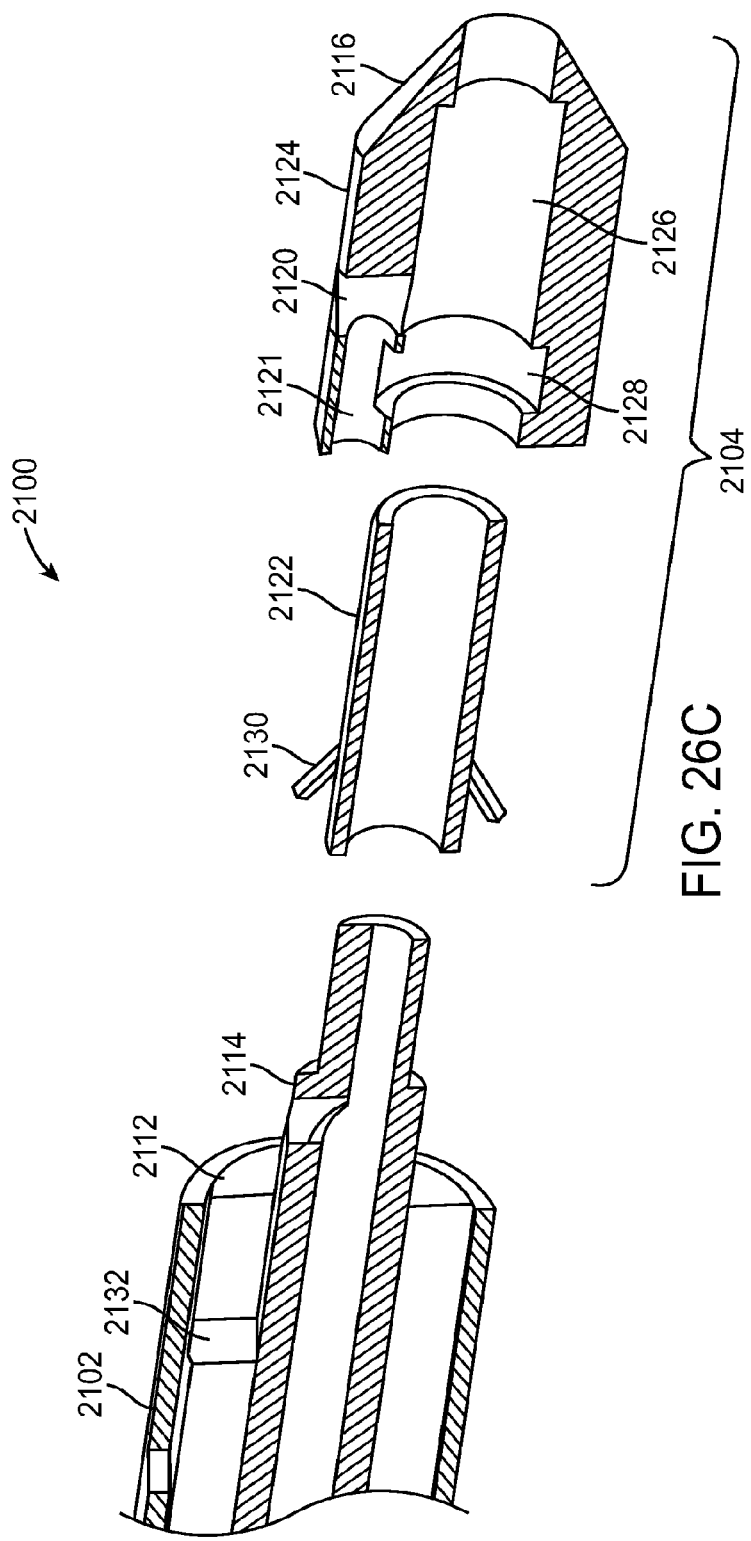

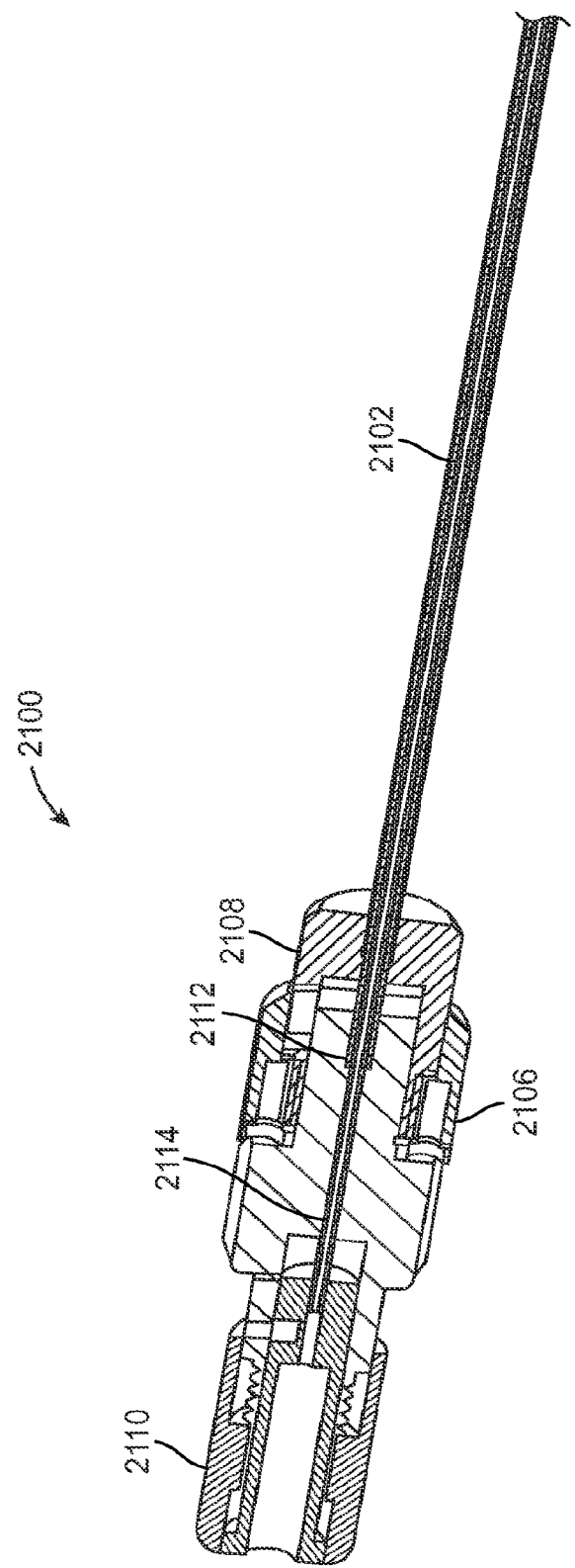

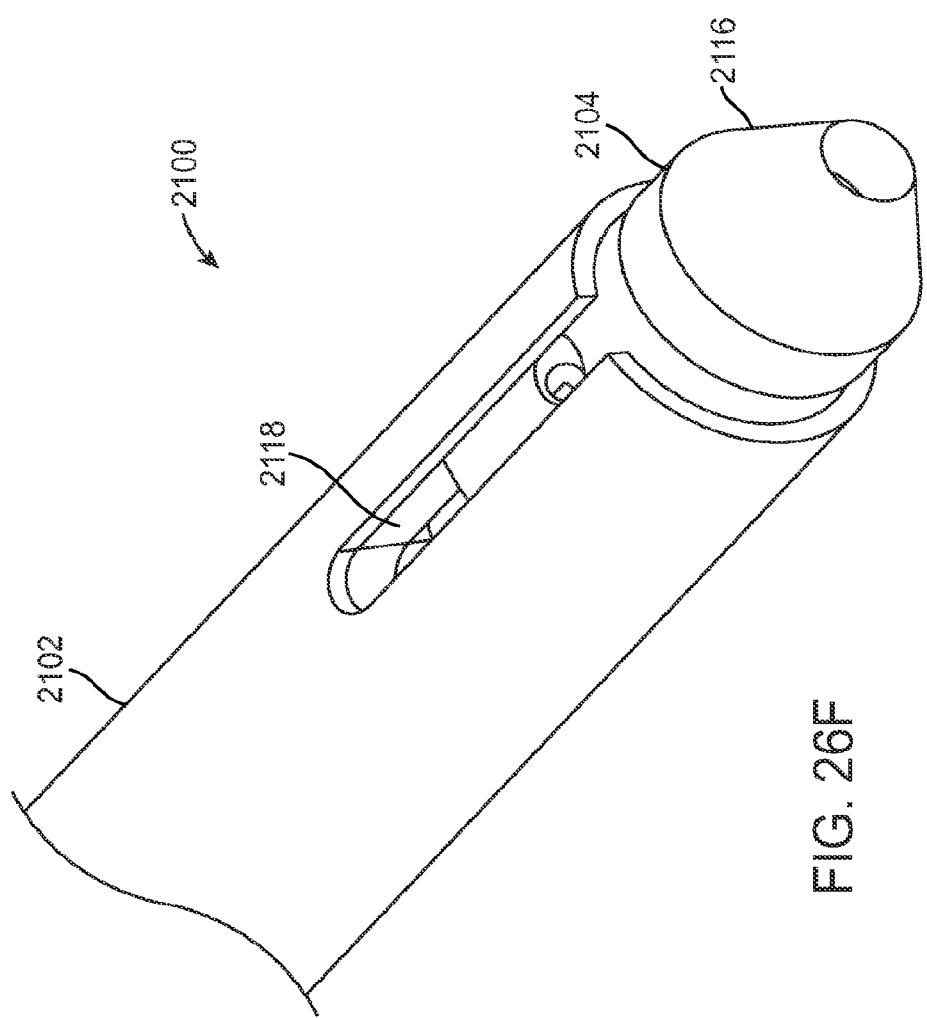

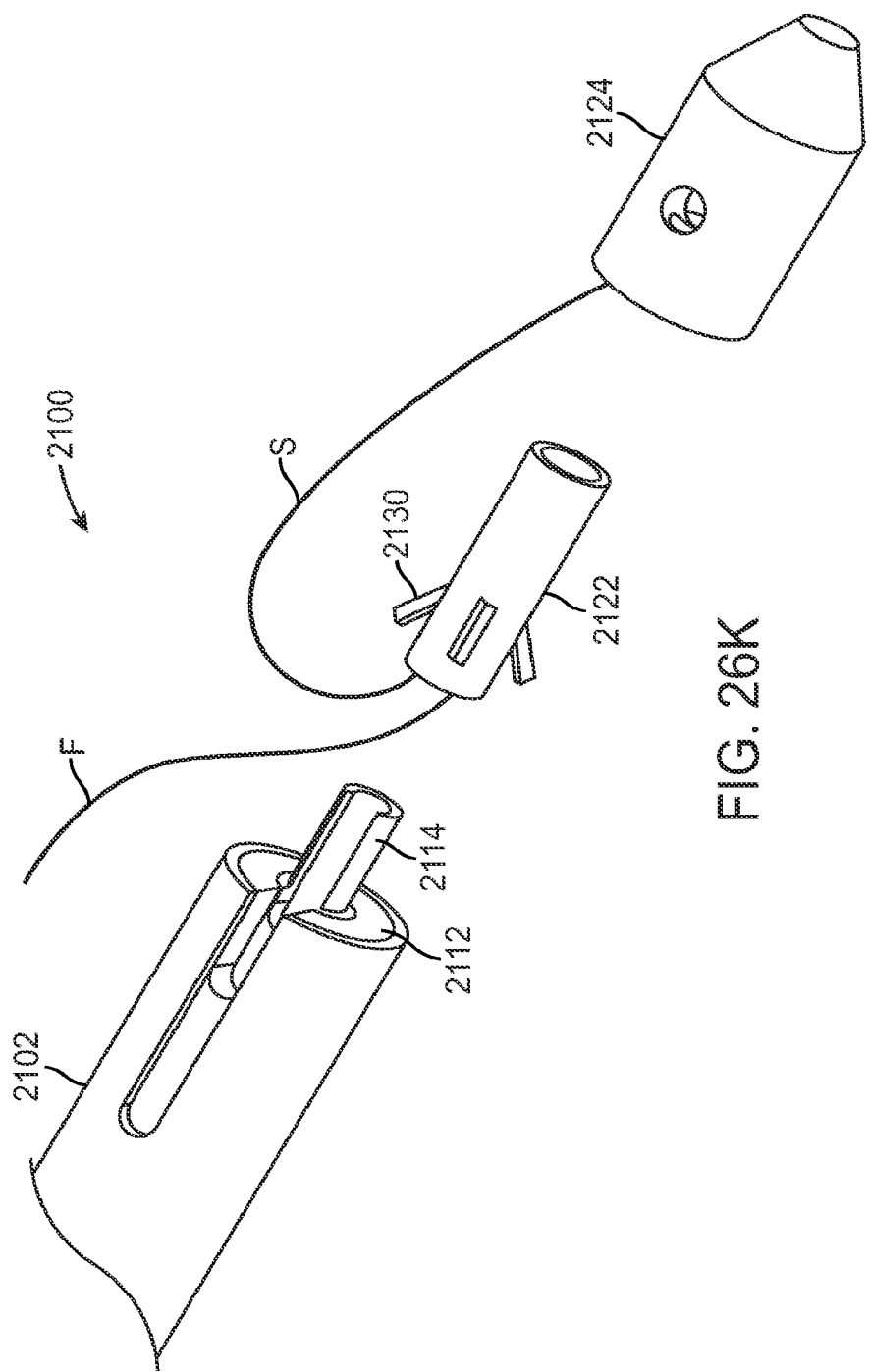

METHODS AND DEVICES TO TREAT DISEASED OR INJURED MUSCULOSKELETAL TISSUE

CROSS-REFERENCE

The present application is continuation of U.S. patent application Ser. No. 12/776,177, which is a non-provisional of, and claims the benefit of U.S. Provisional Patent Application No. 61/177,602, filed May 12, 2009, the entire contents of which are incorporate herein by reference.

The present application is related to U.S. patent application Ser. No. 12/605,065, filed Oct. 23, 2009, the entire contents of which are incorporated herein by reference.

BACKGROUND OF THE INVENTION

1. Field of the Invention

The present disclosure relates to medical devices, systems and methods, and more specifically to methods, systems and devices used for knotless suturing of tissue.

Soft tissue such as tendons, ligaments and cartilage are generally attached to bone by small collagenous fibers which are strong, but which nevertheless still can tear due to wear or disease. Examples of musculoskeletal disease include a torn rotator cuff as well as a torn labrum in the acetabular rim of a hip joint or the glenoid rim in a shoulder joint.

Thus, treatment of musculoskeletal disease may involve reattachment of torn ligaments or tendons to bone. This may require the placement of devices such as suture anchors within bone. A suture anchor is a device which allows a suture to be attached to tissue such as bone. Suture anchors may include screws or other tubular fasteners which are inserted into the bone and become anchored in place. After insertion of the anchor, the tissue to be repaired is captured by a suture, the suture is attached to the anchor (if not already preattached), tension is adjusted, and then the suture is knotted so that the tissue is secured in a desired position. Frequently two or more anchors and multiple lengths of suture are required. This process can be time consuming and difficult to undertake in the tight space encountered during endoscopic surgery and sometimes even in conventional open surgery. Recently, knotless suture anchors having suture clamping mechanisms have been developed to eliminate the need to tie knots but they still can be difficult or awkward to use. Thus, it would be desirable to provide improved knotless suture anchors that are easier to use and also that may take up less space during deployment and that are easier to deploy.

In particular, treating musculoskeletal disease in a hip joint can be especially challenging. The hip joint is a deep joint surrounded by a blanket of ligaments and tendons that cover the joint, forming a sealed capsule. The capsule is very tight thereby making it difficult to advance surgical instruments past the capsule into the joint space. Also, because the hip joint is a deep joint, delivery of surgical instruments far into the joint space while still allowing control of the working portions of the instrument from outside the body can be challenging. Additionally, the working space in the joint itself is very small and thus there is little room for repairing the joint, such as when reattaching a torn labrum to the acetabular rim. Moreover, when treating a torn labrum, the suture anchor must be small enough to be inserted into the healthy rim of bone with adequate purchase, and the anchor also must be short enough so that it does not protrude through the bone into the articular surface of the joint (e.g. the acetabulum). Existing anchors can be too large. Thus, it would be desirable to provide suture anchors that have a small diameter and length.

Additionally, in most surgical procedures, a pilot hole is drilled at the implantation site prior to screwing in the suture anchor. In other cases a self-tapping device tip is used to screw in the device without a pilot hole. Alternatively, ultrasonic energy has been proposed in embedding bone anchors in bony tissue without pre-drilling a pilot hole. These methods of implanting a device in bone tissue, while commonly used in surgery today, are not optimal. Pre-drilling a pilot hole prior to placing the device requires the surgeon to exchange tools through the cannula and to locate the pilot hole after introducing the implant in the arthroscopic field. Self-tapping devices are limited to use at sites with the appropriate thickness of cortical bone. Ultrasonic energy based devices are susceptible to large energy losses with minor changes in device configuration, and rely on ultrasonic energy sources which can be expensive. Therefore, there is a need for improved devices, systems and methods which overcome some of the aforementioned challenges.

In addition, current arthroscopic devices are limited in that they generally approach a surgical site in a longitudinal manner. If it is necessary to implant a bone anchor at an angle, which is often the case, the current devices do not fully address the need for an off axis approach. Furthermore, there is a need for anchors to be compatible with a device that implants the anchors at an angle off of the longitudinal axis of the shaft of the driving device. At least some of these objectives will be met by the inventions described hereinbelow.

2. Description of the Background Art

Patents disclosing suture anchoring devices and related technologies include U.S. Pat. Nos. 7,390,329; 7,309,337; 7,144,415; 7,083,638; 6,986,781; 6,855,157; 6,770,076; 6,656,183; 6,066,160; 6,045,574; 5,810,848; 5,728,136; 5,702,397; 5,683,419; 5,647,874; 5,630,824; 5,601,557; 5,584,835; 5,569,306; 5,520,700; 5,486,197; 5,464,427; 5,417,691; and 5,383,905. Patent publications disclosing such devices include U.S. Patent Publication Nos. 2009/0069845 and 2008/0188854 and PCT Publication No. 2008/054814.

SUMMARY OF THE INVENTION

The present invention provides devices, systems and method for knotless suturing of tissue. Exemplary procedures where knotless suturing may be advantageous include repair of torn rotator cuffs, as well as a torn labrum in the acetabular rim of a hip joint or the glenoid rim in a shoulder joint.

In a first aspect of the present invention a knotless suture anchoring system comprises an outer anchor having a central channel and a distal tip adapted to penetrate tissue and an inner anchor positionable in the central channel of the outer anchor. The system also includes a locking feature on one or both of the inner and outer anchors and that is configured to retain the inner anchor within the central channel. A continuous length of suture is coupled with the inner and outer anchors and the suture has a free end. At least one of the inner and outer anchors further comprises a cinching mechanism that is adapted to allow the suture to be tensioned by passage of the suture through the cinching mechanism in a first direction while movement of the suture through the cinching mechanism in a second direction opposite the first direction is constrained.

In another aspect of the present invention, a knotless suture anchoring system comprises an outer anchor having a central channel and a distal tip adapted to penetrate tissue. An inner anchor is positionable in the central channel of the outer anchor and has a distal tip that is adapted to penetrate and be retained in tissue outside the outer anchor whereby the inner anchor may be positioned either in the outer anchor or in tissue apart from the outer anchor. The system also includes a locking feature on one or both of the inner and outer anchors that is configured to retain the inner anchor within the central channel and a continuous length of suture coupled with the inner and outer anchors. The suture has a free end. At least one of the inner and outer anchors further comprises a clamping mechanism adapted to clamp the suture under tension without knotting the suture.

Sometimes the central channel extends only partially through the outer anchor and the locking feature may comprise an annular recessed region in the central channel of the outer anchor. The outer anchor may comprise an outer surface having surface features that are adapted to anchor the outer anchor with the tissue or to promote tissue ingrowth.

The inner anchor locking feature may comprise a plurality of resilient fingers extending radially outward from the inner anchor. The clamping mechanism may comprise a cinching mechanism adapted to allow the suture to be tensioned by passage of the suture through the cinching mechanism in a first direction while movement of the suture through the cinching mechanism in a second direction opposite the first direction is constrained. The cinching mechanism may comprise a deflectable arm coupled to either the inner or the outer anchor. Additionally, the cinching mechanism often may be operative regardless of the position of the inner anchor relative to the outer anchor. The deflectable arm may be integral with either the inner or the outer anchor and the deflectable arm may be disposed in an aperture within either the inner or the outer anchor. The aperture may be in an axial channel extending at least partially through the inner anchor. The deflectable arm may move in a first radial direction when the suture is pulled in the first direction and the arm may move in a second radial direction when the suture is pulled in the second direction. The suture may be clamped between the arm and a wall of the aperture when the suture is pulled in the second direction. The arm may be resilient so as to return to an unbiased position after moving in either the first or the second radial directions. The arm may deflect radially inward when the suture is pulled in the second direction to clamp the suture between the arm and an opposing wall of the aperture, thereby constraining movement of the suture in the second direction.

The system may also comprise a delivery instrument having a longitudinal axis, and the delivery instrument may be adapted to carry both the inner anchor and the outer anchor simultaneously. The delivery instrument often may have an axial lumen, the inner and the outer anchors being releasably carried in the axial lumen. The delivery instrument may comprise a steering mechanism that is adapted to deflect a distal portion of the instrument. Also the delivery instrument may comprise a suture management feature that is adapted to releasably hold the length of suture and prevent tangling thereof. In some embodiments, the delivery instrument may be configured to receive a drill which is adapted to create an aperture in the tissue sized to receive the inner or the outer anchor. In still other embodiments, the delivery instrument may be adapted to deliver the inner anchor and the outer anchor at an angle transverse to the longitudinal axis of the delivery instrument. The delivery instrument may have a hammer element that is coupled with the delivery instrument and that is adapted to convert axial movement along the longitudinal axis of the delivery instrument into an impacting force transverse to the longitudinal axis of the delivery instrument. Each of the inner and the outer anchors have a longitudinal axis and the delivery instrument may carry the inner and the outer anchors such that the longitudinal axis of both anchors is transverse to the longitudinal axis of the delivery instrument.

The central channel of the outer anchor may be disposed at an angle transverse to a longitudinal axis of the outer anchor. Thus, the inner anchor may be disposed at an angle transverse to the longitudinal axis of the outer anchor when received in the central channel.

The delivery instrument may comprise a jaw having first opposable member pivotably coupled with a second opposable member. The first opposable member may carry the inner anchor and the second opposable member may carry the outer anchor, and actuation of the jaw may insert the inner anchor into the outer anchor. The inner and the outer anchors may each have a longitudinal axis and the anchors may be carried by the opposable members such that the longitudinal axis of the anchors are transverse to a longitudinal axis of the opposable members.

In still another aspect of the present invention, a knotless suture anchoring system comprises a first anchor having a housing with a central channel sized to receive a suture therein. The system also has a cinching mechanism with a radially deflectable arm integral with the housing and disposed at least partially in the central channel. The suture passes through an opening in the arm and passes between a free end of the arm and the housing. The cinching mechanism is adapted to allow the suture to pass through the cinching mechanism in a first direction while movement of the suture through the cinching mechanism in a second direction opposite the first direction is constrained.

The cinching mechanism may comprise a deflectable arm coupled to the first anchor. The deflectable arm may be integral with the first anchor and it may be disposed in an aperture within the first anchor. The aperture may be in an axial channel extending at least partially through the first anchor. The arm may move in a first radial direction when the suture is pulled in the first direction and the arm may move in a second radial direction when the suture is pulled in the second direction. The suture may be clamped between the arm and a wall of the aperture when the suture is pulled in the second direction. The arm may be resilient so as to return to an unbiased position after moving in either the first or the second radial directions. The arm may deflect radially inward when the suture is pulled in the second direction to clamp the suture between the arm and an opposing wall of the aperture, thereby constraining movement of the suture in the second direction.

The housing may comprise a distal tip adapted to penetrate tissue. The housing may also comprise an outer surface having surface features adapted to anchor the first anchor in the tissue or to promote tissue ingrowth. The system may also include a second anchor having an inner channel configured to receive the first anchor. The inner channel may comprise a locking feature adapted to engage with the first anchor to retain the first anchor in the second anchor.

In yet another embodiment of the present invention, a knotless suture anchoring system may comprise a pin having a distal tip adapted to penetrate tissue, an anchoring bracket and a length of suture. The suture is adapted to be coupled to the pin and the bracket. The bracket may be L-shaped and may comprise a suture management feature adapted to receive and hold the suture. The suture management feature may comprise a slit in the bracket. The bracket may also have an anchoring pin that is adapted to penetrate the tissue thereby fixing the bracket to the tissue. The suture may be formed into a loop sized to capture tissue to be repaired and the tissue to be repaired may comprise a torn labrum. The anchoring bracket or the pin may further comprise a cinching mechanism adapted to allow the suture to be tensioned by passage of the suture through the cinching mechanism in a first direction while movement of the suture through the cinching mechanism in a second direction opposite the first direction is constrained.

In another aspect of the present invention, a knotless suture anchoring system comprises a delivery instrument having a longitudinal axis, a shaft axially movable along the longitudinal axis, and a hammer adapted to convert axial movement along the longitudinal axis into movement transverse thereto. A first anchor is carried by the delivery instrument and has a distal tip adapted to penetrate tissue. Axial movement of the slidable shaft along the longitudinal axis moves the hammer in a motion transverse thereto, thereby impacting the anchor, whereby the first anchor is driven into the tissue at an angle transverse to the longitudinal axis of the delivery instrument.

In still another aspect of the present invention, a method of knotless suturing comprises providing a delivery instrument carrying a first anchor and a second anchor, wherein a continuous length of suture is coupled with the first and the second anchors. The delivery instrument is advanced to a treatment region comprising treatment tissue and the first anchor is placed into a first region of the tissue. The suture is coupled to a portion of the treatment tissue and the second anchor is attached to the first anchor. The suture is tensioned and secured without knotting the suture. The suture is secured by moving the suture through a cinching mechanism in the first or the second anchor, wherein the cinching mechanism is adapted to allow the suture to move through the cinching mechanism in a first direction while movement of the suture through the cinching mechanism in a second direction opposite the first direction is constrained independently of the position of the second anchor relative to the first anchor.

The second anchor may be stationary relative to the first anchor during the entire step of securing the suture. The tissue may comprise bone and the step of placing the first anchor or the step of placing the second anchor may comprise drilling a pilot hole into the bone. The pilot hole may be sized to receive the first or the second anchor. The method may further comprise deflecting a distal portion of the delivery instrument. The first region of tissue may comprise the acetabulum and the treatment tissue may comprise an acetabular labrum.

The step of attaching the second anchor to the first anchor may comprise inserting the second anchor into a central channel of the first anchor and locking the two anchors together to prevent axial movement of the first anchor relative to the second anchor. The delivery instrument may further comprise an actuator mechanism near a proximal end of the instrument and the step of placing the first anchor or the step of placing the second anchor comprises actuating the actuator mechanism to expose the first or the second anchor from the delivery instrument. The step of securing may comprise clamping the suture between a deflectable arm and an inner wall of the first or the second anchor. The arm may be integral with either the first or the second anchor.

The step of attaching may comprise placing the second anchor in a central channel within the first anchor. The cinching mechanism may be disposed in an inner channel of the second anchor. The delivery instrument has a longitudinal axis, and the step of placing the first anchor may comprise placing the first anchor into the first region at an angle transverse to the longitudinal axis of the delivery instrument. The step of attaching the second anchor to the first anchor may comprise actuating a jaw disposed on the delivery instrument.

In another aspect of the present invention, a method of knotless suturing comprises providing an anchoring device having an anchoring bracket, a length of suture and a pin, wherein the suture is coupled to the bracket and the pin. The bracket is anchored to a first tissue region and tissue to be treated is captured with the suture. The pin is secured to a structure selected from the bracket and a second tissue region and the suture is tensioned.

The step of anchoring the bracket may comprise inserting a pin coupled to the anchoring bracket into the first region. The step of capturing the tissue to be treated may comprise looping the suture around said tissue. The step of tensioning the suture may comprise passing the suture through a cinching mechanism in the pin or in the anchoring bracket. The cinching mechanism is adapted to allow the suture to pass through the cinching mechanism in a first direction while movement of the suture through the cinching mechanism in a second direction opposite the first direction is constrained. Tensioning the suture may comprise securing the suture without knotting the suture.

These and other embodiments are described in further detail in the following description related to the appended drawing figures.

BRIEF DESCRIPTION OF THE DRAWINGS

FIGS. 8A-8C illustrate an exemplary embodiment of a device that drives two anchors through a single conduit.
FIGS. 12A-12C show devices for temporary attachment of tissue to bone.

FIGS. 23A-23B show an eccentrically mounted impact driver for driving bone anchors.

FIG. 24 shows an inertia equalizing driver for driving bone anchors.

DETAILED DESCRIPTION OF THE INVENTION

Figure 1:
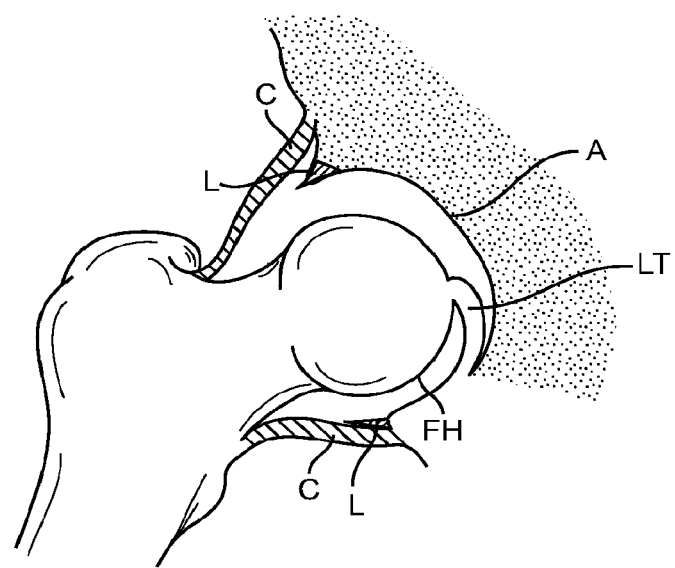
FIG. 1 illustrates anatomy of the hip joint.
Figure 2:
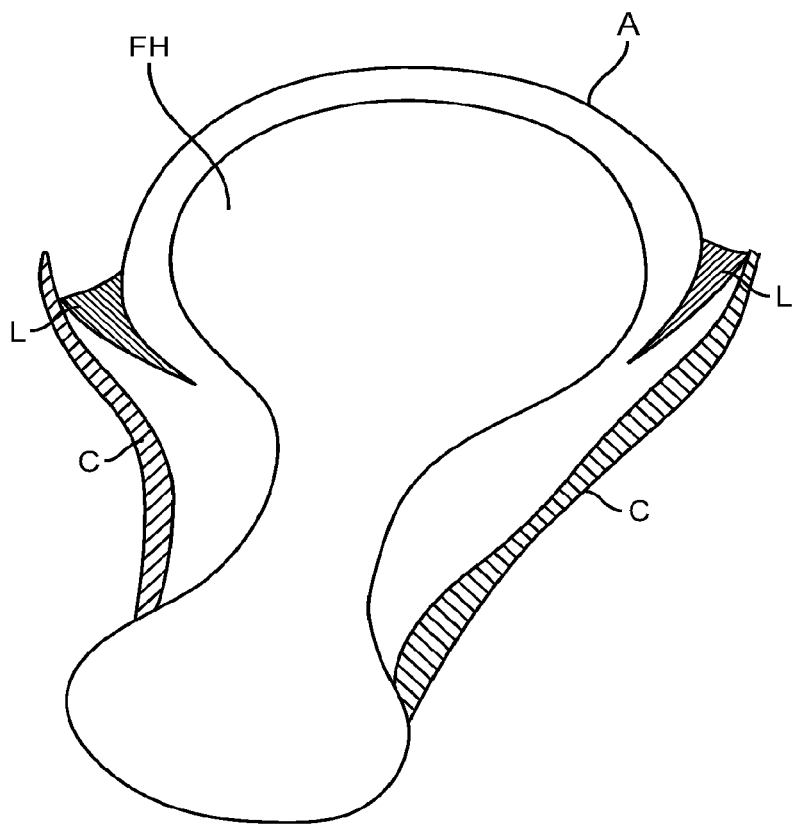
FIG. 2 is a top view of the hip joint.

Exemplary use of the devices, systems and methods of the present invention will be discussed primarily in terms of treatment of a hip joint. However, one of skill in the art will appreciate that other areas of the body including joints such as the shoulder joint, the ankle, wrist and other joints may also be treated. Thus, the exemplary usage described herein is not intended to be limiting. FIG. 1 illustrates the basic anatomy of a hip joint. In FIG. 1 the hip joint is formed between the head of the femur FH and the acetabulum A, a concave surface of the pelvis. A blanket of ligaments cover the joint forming a capsule C. Additionally the acetabular labrum L, a fibrocartilaginous lip, surrounds the head of the femur, deepens the joint pocket and increases the surface area of contact. The ligamentum teres LT is a ligament attached to a depression in the acetabulum (the acetabular notch or fossa) and a depression on the femoral head (the fovea of the head). FIG. 2 is a top view of a hip joint highlighting the labrum L.

Figure 3:
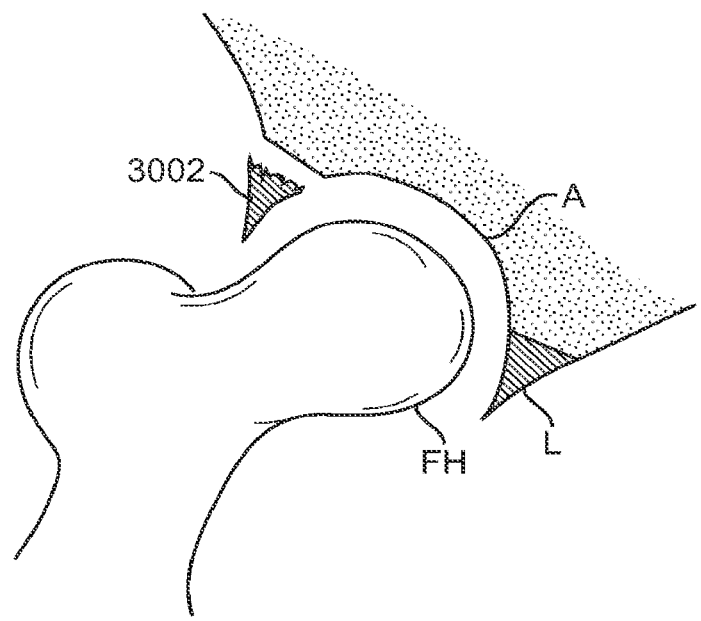
FIG. 3 illustrates a torn labrum in a hip joint.
Figure 4:
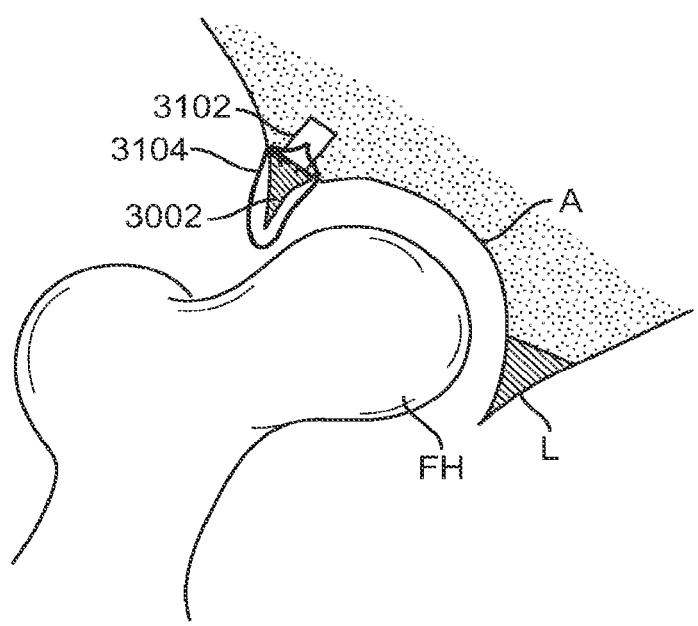
FIG. 4 illustrates reattachment of a labrum in a hip joint.

The labrum L can tear or separate from the acetabular rim due to wear or disease and this can result in pain as well as loss of joint mobility. FIG. 3 illustrates a torn labrum 3002. Surgeons typically use suture and suture anchors to reattach the labrum to the acetabular rim. FIG. 4 illustrates how a suture anchor 3102 is used to anchor suture 3104 to the acetabular rim A. The suture 3104 is looped around and captures the torn labrum 3002 holding it against the bone until it heals and reattaches. The suture is either pre-attached to the anchor, or it is attached during the repair procedure. Suture length and tension is then adjusted to ensure apposition of the damaged tissue with the substrate tissue. Suture anchors are typically used instead of screws, pins, rivets or other fasteners due to the limited working space within the joint.

Figure 5A:
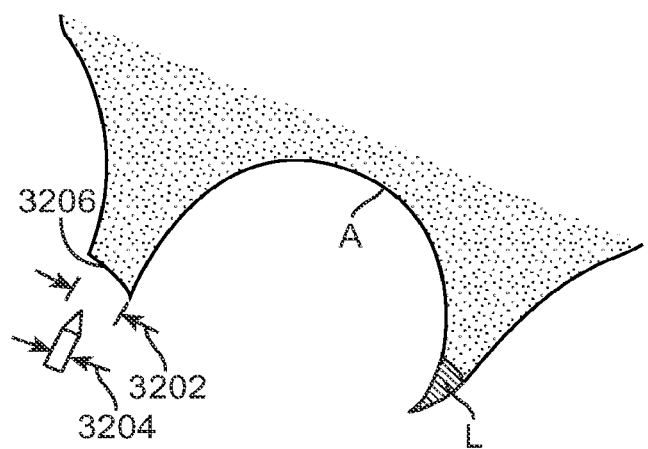
FIGS. 5A-5C illustrate use of a suture anchor in an acetabular rim.
Figure 5B:
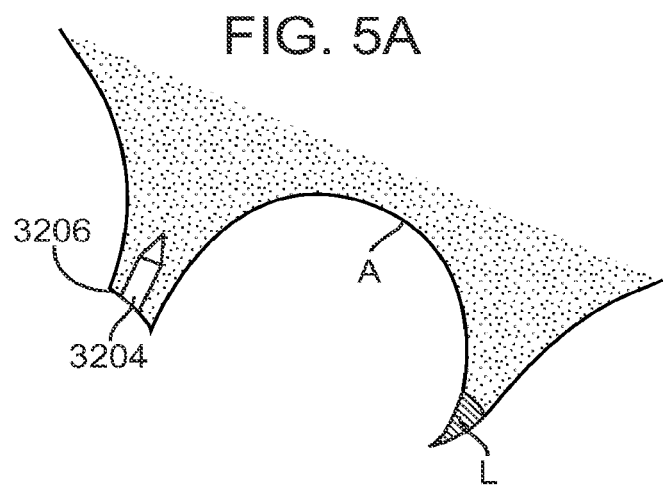
Figure 5C:
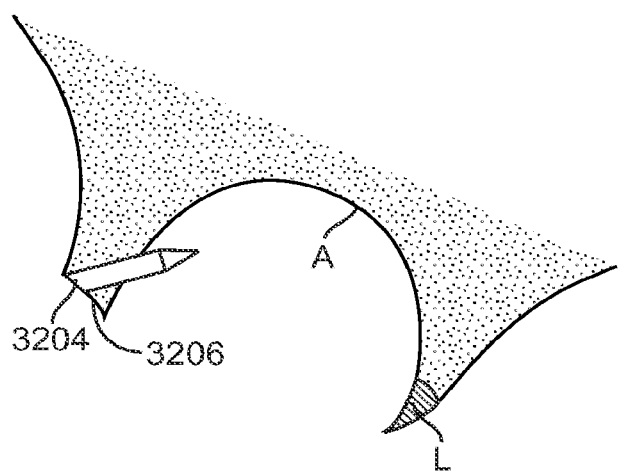

Referring now to FIGS. 5A-5C, the size of the suture anchor can be very important depending on the treatment zone. For example, when placing a suture anchor into the acetabular rim 3206 to repair the labrum L, the anchor width or diameter 3204 cannot exceed the width 3202 of the acetabular rim 3206. Moreover, as shown in FIGS. 5A-5B, the anchor width 3204 must be small enough relative to the width of the acetabular rim 3206 so that adequate purchase is obtained without comprising strength of the rim 3206. Additionally, length of the anchor can also be critical. In FIG. 5B, the anchor 3204 is placed orthogonally into the acetabular rim and thus anchor may be as long as necessary to obtain adequate purchase in the bone without risk of extending into the joint socket. However, it may be difficult to insert the anchor orthogonally into the acetabular rim due to the angle of approach, the narrow width of the rim, or other reasons. In such cases, the anchor may be placed at a non-perpendicular angle relative to the rim surface, or it may be placed into a lateral facet of the acetabulum. In such cases, if the anchor is either too long or the angle is too great as shown in FIG. 5C, the anchor may pass entirely through the bone and exit into the joint itself, here the acetabular socket A, potentially damaging the cartilage and interfering with joint motion. Thus, when repairing a torn labrum in an acetabular or glenoid rim, the anchor has a diameter usually less than 5 mm, preferably less than 4 mm, and more preferably 3.5 mm or less. The length must be long enough to gain adequate purchase in the bone while short enough to avoid penetration into the articular surface, preferably being at least about 5 mm and less than about 14 mm in length.

Figure 6:
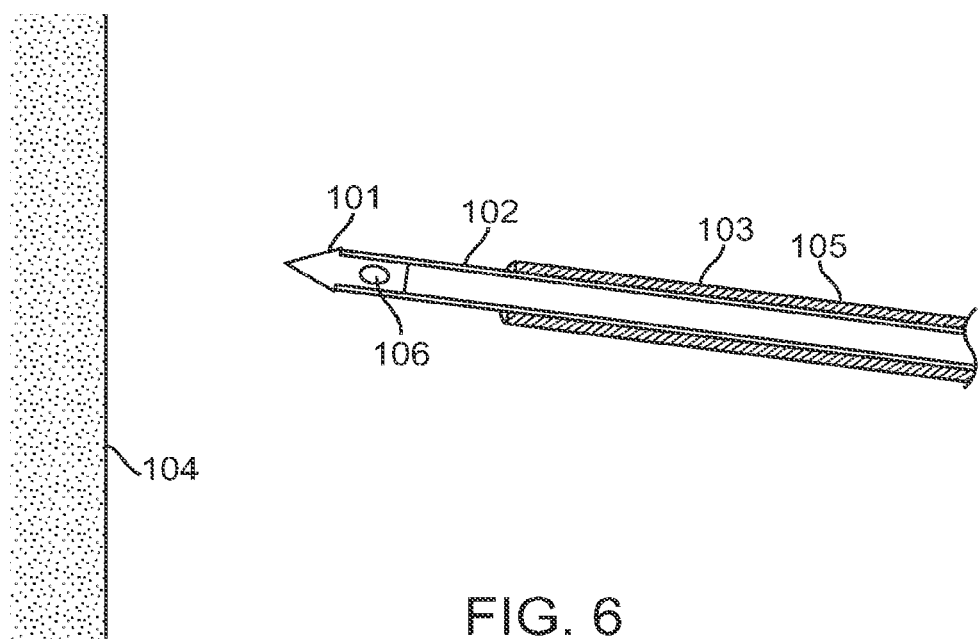
FIG. 6 is a sectional view of an anchor loaded in the distal end of an anchor driver and placed through a shaft.

Referring now to FIG. 6, an arthroscopic delivery instrument may be used to deliver an implantable device, here a suture anchor, to a desired anchor site. FIG. 6 shows a cross-sectional view of a delivery instrument 103 having an tubular outer shaft 105 that is sized for endoscopic delivery into a joint space, such as the hip, shoulder, ankle, wrist, or other joint. A common cannula used in arthroscopy has an inner diameter of approximately 5.5 mm and therefore the outer shaft 105 should have a diameter small enough to freely move in the cannula, thus outer shaft 105 is preferably about 5.4 mm in diameter or less. Additionally, the shaft 105 is long enough to extend into the treatment region such as a joint space and thus is preferably at least about 16.5 cm (6.5 inches) long. These dimensions may be applied to any of the delivery instruments disclosed below.

Figure 7A:
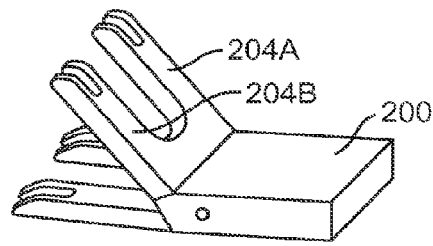
FIGS. 7A-7E show an exemplary embodiment of a device that drives two anchors.
Figure 7B:
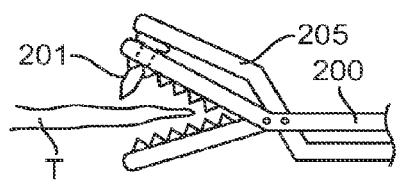
Figure 7C:
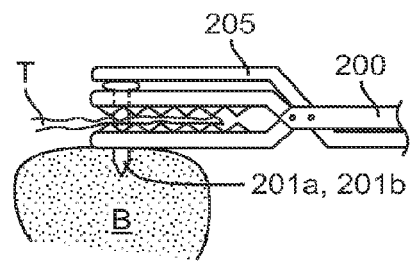
Figure 7D:
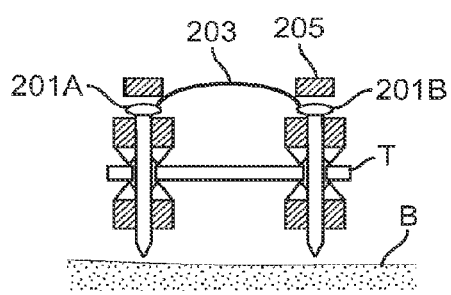
Figure 7E:
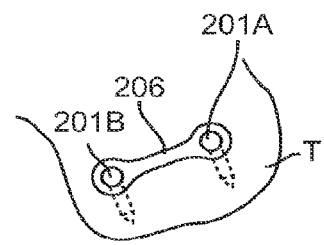

The shaft 105 carries an inner impactor 102 and a suture anchor 101 is releasably coupled with the impactor. The suture anchor 101 has a pointed or sharpened distal tip in order to allow it to penetrate bone 104 or other tissue. Once the suture anchor 101 has been delivered to a desired anchor site, the proximal end of the impactor 102 may be hit with a hammer or other object in order to drive the anchor 101 into the bone 104. Alternatively, the impactor may be energized with other forms of energy, such as ultrasonic energy or other types of oscillating or vibrating energy in order to drive the anchor 101 into the bone 104. The impactor may drive the implant into bone at frequencies between 10 and 20 kHz, preferably between 20 and 1000 Hz, more preferably between 30 and 500 Hz. The amplitude at which the impactor is energized may be at amplitudes of 100 to 1000 microns, preferably 200 to 750 microns, more preferably 300-500 microns. A suture (not illustrated) may be attached to the anchor 101 by tying the suture to aperture 106, or the suture may be attached using other techniques well known in the art including crimping or bonding The embodiment of FIG. 6 allows a single suture anchor to be deployed at a time. In some situations, it may be desirable to deploy multiple suture anchors simultaneously. The exemplary embodiment of FIGS. 7A-7E show the distal end of an endoscopic delivery instrument 200 that drives two anchors 201a and 201b into tissue independently or simultaneously. Any suture anchor disclosed herein may be used, and other anchors disclosed in U.S. patent application Ser. No. 12/605,065, filed Oct. 23, 2009, may also be used, the entire contents of which are incorporated herein by reference. In the exemplary embodiment of FIG. 7A, the endoscopic (or arthroscopic, or laparoscopic, etc.) device performs several functions. It comprises two arms 204a and 204b, each of which holds an anchor 201a, 201b, with a suture (see FIG. 7D) or other connective material (see FIG. 7E) connecting the proximal ends of the two anchors. Once the device is in position, the arms capture the tissue T to be repaired and the anchors are driven through the tissue into the desired bone B using impact drivers 205 operably coupled with the arms 204a, 204b. The impact driver 205 is shown moving at a right angle or perpendicular to the arms, however it could also move translationally along the long axis of the grasper, or the anchor itself could be curved. This device is intended to be introduced through a cannula or small incision. To enable the device to pass through a cannula or small incision and still have an appropriate separation between the two anchors, the device may be fabricated so that the arms can be laterally separated, for example by hinging them apart. Such a device would be introduced through the cannula with the arms close together, to reduce the overall width of the device. Then, once the device has been introduced into the body to the surgical site, the arms are separated from each other, tensioning the suture between the anchors. The anchors can then be driven into the tissue by closing the arms around the tissue, and then the anchors may be driven into the bone B either by direct hammering or by impacting the anchors using impact drivers 205 as described above. FIG. 7B illustrates the arms capturing the tissue T to be repaired. In FIG. 7B, the arms 204a, 204b may comprise teeth or other surface features that allow the tissue T to be more securely grasped. FIG. 7C illustrates the arms closed around the tissue T with an anchor 201a or 201b passing through the tissue T and being secured to the bone. FIG. 7D illustrates an end view of FIG. 7C, showing the tissue T grasped between the arms 204a, 204b and the anchors 201a, 201b penetrating the tissue T about to penetrate the bone B. A suture 203 extends between the two anchors 201a, 201b. By having an anchor with a cinchable/ tensionable suture, the suture tension between the anchors may be adjusted. FIG. 7E shows as alternate to having a suture connect the anchors. A connective member 206 is constructed that spans the gap between the two anchors and distributes the force generated by the anchors to the tissue T. This member may be flexible so that the two halves of the grasper are movable with respect to one another. Multiple sets of anchors could be placed depending on the size of the repair.

There are numerous variations and elaborations on this approach, which may provide added benefits and enhance their applicability to a range of different clinical settings. For instance, each arm might additionally have a grasper near the end of each arm, which is configured to expand and grasp tissue (e.g. the rotator cuff). While holding the tissue, the device can then be repositioned (for example, repositioning the device over the humeral head to apply the appropriate tension to the rotator cuff). Then the anchor can be driven through this tissue into another tissue (such as the bone of the humeral head) to anchor the tissue. The grasper is then released. The grasper and arm may also have appropriate slots to allow the instrument to be removed while leaving the anchors in place with a tight suture connecting them, approximating the tissue to the bone with just the right amount of tension to allow rapid healing of the cuff to the bone.

The anchors may be driven parallel to the axis of the arms, or at a right angle to the axis of the instrument, or at a lesser angle depending on the angle necessary to drive into tissue and bone. For instance, a more linear arrangement may work well for labral reattachment in the shoulder and the hip, and a more right-angled arrangement might work better for reattaching the rotator cuff. The end configuration of the instrument may have the ability to articulate or be actively steered, to facilitate anchor placement while conforming to the various anatomies.

As described above, the suture between the two anchors might be appropriately tensioned simply by adjusting the initial separation of the jaws, and/or by the action of driving the anchors into the tissue. However, this system could also be combined with an anchor that has a suture lock mechanism so that the suture can be discretely tensioned after the anchor has been placed. This feature might be particularly useful in a knotless rotator cuff repair system. It might alternatively be preferable to have separate sutures on each of the anchors, which could then be tied together after the anchors are placed. Several embodiments of a suture locking mechanism are disclosed below and they may be combined with any of the anchor embodiments disclosed herein.

The distance between the anchors may be adjustable depending on the anatomy and amount of repair necessary. The distance can be varied through the grasper controls. One or more sets of anchors may be loaded on the device in a magazine fashion such that the anchors are loaded in a tubular magazine and advanced through the grasper. This would facilitate a complete tissue repair procedure without removing the instrument from the patient.

FIG. 8A illustrates another embodiment of a device for driving multiple anchors through a single conduit. This embodiment includes a delivery instrument 300 that is adapted to drive multiple anchors 301a, 301b through channel 302 of conduit 303. The means of driving one or more anchors is separate from grasping tissue. FIG. 8A shows a cross section of the instrument with two anchors. A suture having ends 304a, 304b extends from each of the anchors. The sutures are preferably pre-connected to the two anchors, although they may be connected during the surgical procedure. The conduit 303 has two distinct lumens 305a, 305b which are used to carry the anchors. A relief between the lumens allows for the passage of the suture from one anchor to the other if necessary. The two lumens 305a, 305b may be separate tubes contained within an external tube that holds all of the elements and allows passage of the device through a cannula for use in arthroscopic or mini-open procedures, such as rotator cuff repair or labral repair in the hip. The lumens and external tube may be steel or a high strength polymer or a combination of materials. The lumens may be round or rectangular in cross section depending on the cross section of the anchors. Impactors, or drivers 306a, 306b for the anchors are shown and may be independently or simultaneously driven from a pneumatic or mechanical driver body (not shown).

This embodiment is useful for positioning multiple anchors simultaneously that are connected by suture or other means. The instrument may be used to re-attach the labrum in the shoulder or the hip or for other procedures. To accomplish this, a pair of anchors is positioned adjacent to one another and driven through the labrum into the bone below. A connection means between the anchors provides positive fixation of the labrum to the bony tissue below. The tissue grasper features of the previous embodiment may also be used with this embodiment. Thus, all of the features and permutations described previously for tissue attachment may be applied to this embodiment as well.

FIGS. 8B-8C illustrate how a multiple anchor system loaded with sutures may be used. In this embodiment instrument 300 is first used to place a first pair of anchors 307a, 307b through tissue T into underlying bone B. Sutures are fixed to anchors at positions 307a and 307b. Instrument 300 is then used to place anchors 308a, 308b into bone B adjacent tissue T. The suture ends attached to anchors 308a, 308b are then tied to sutures attached to anchors 307a, 307b. There may be one or more sutures attached to each of the anchors such that a crisscross pattern may be produced which creates good apposition of tissue T to bone B.

Figure 9A:
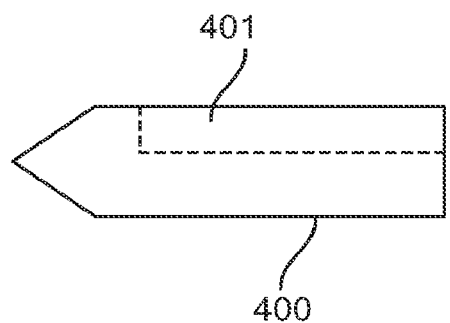
FIG. 9A shows a malleable anchor.
Figure 9B:
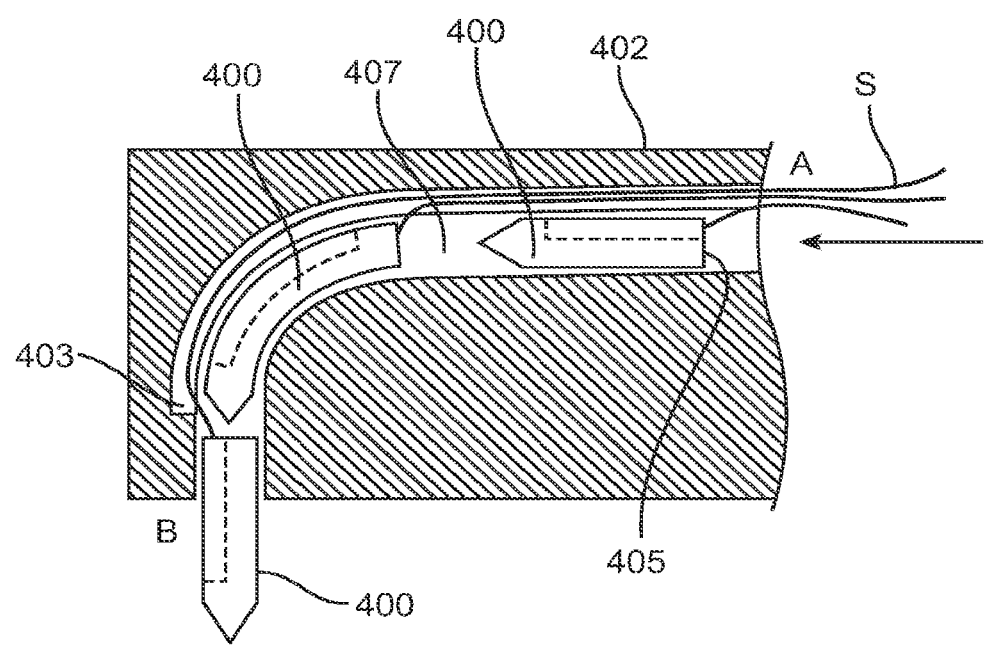
FIG. 9B is a sectional view showing the delivery of a malleable anchor.

In another embodiment shown in FIGS. 9A-9B, a malleable, flexible, or shapeable anchor is disclosed. Multiple anchors 400 may be loaded into a main channel 407 of delivery instrument 402 in a stacked relationship. A proximal land 405 on the anchor 400 engages a flexible internal driving member to drive the anchor into bone. A suture S or other connection means is fixed to anchor 400 within anchor channel 401. An axial passage 403 in delivery instrument 402 receives each length of suture S attached to anchors 400. As the anchor is driven out of the rigid sheath into bony tissue the anchor changes from a curved to a straightened configuration due to the malleable or flexible nature of the anchor material. The anchor may alternatively be made from discrete sections that separate around the bend of the delivery tube and then interlock as they exit the straight portion. In an exemplary embodiment the anchor consists of rigid portions that are connected by articulating elements along the anchor. In another embodiment the anchor is constructed of a shape memory material and is forcibly restrained in a curved configuration prior to deployment of the anchor. One of skill in the art will appreciate that it is not necessary for the anchor to return to or assume a strictly straight shape. In still other embodiments, the anchors are fit together similar to pencil lead cartridges and driven together as a train. Individual anchors are deployed as they exit the instrument. FIG. 9B illustrates deployment of the anchor 400. The anchors curve around from position A to exit at B. The anchors may exit as straight or may maintain a curve depending on the application and the bore at exit B.

Figure 10A:
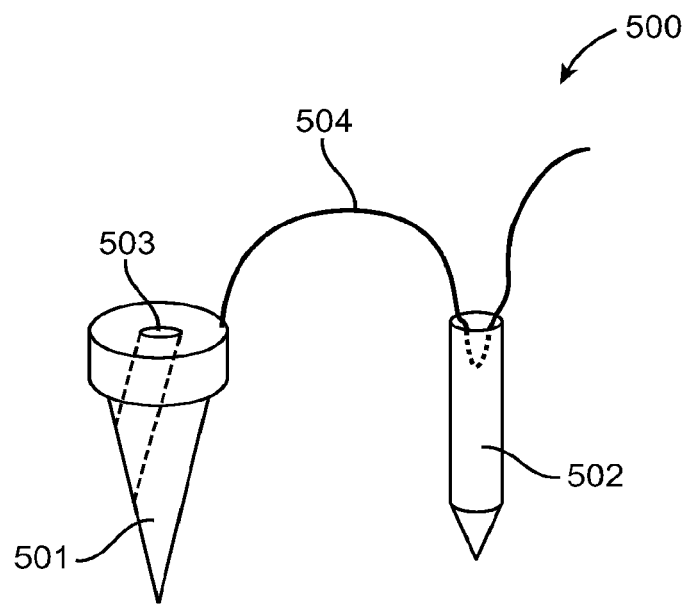
FIGS. 10A-10B show a multiple anchor system.

In another embodiment, anchor systems are disclosed which deliver multiple anchors with proper suture tensioning and locking capabilities. FIG. 10A shows an anchor system 500 with a bone anchor 501 that accepts a smaller anchor 502 passed through tissue for use e.g. in rotator cuff or labral repair in the shoulder or hip. The larger bone anchor has a hole 503 in it to receive the smaller anchor. The hole that accepts the smaller anchor 502 may be along the longitudinal axis of the anchor 501 or at an oblique or right angle (transverse to the longitudinal axis), depending on the desired configuration for the applicable procedure. A suture 504 connects the two anchors.

Figure 10B:
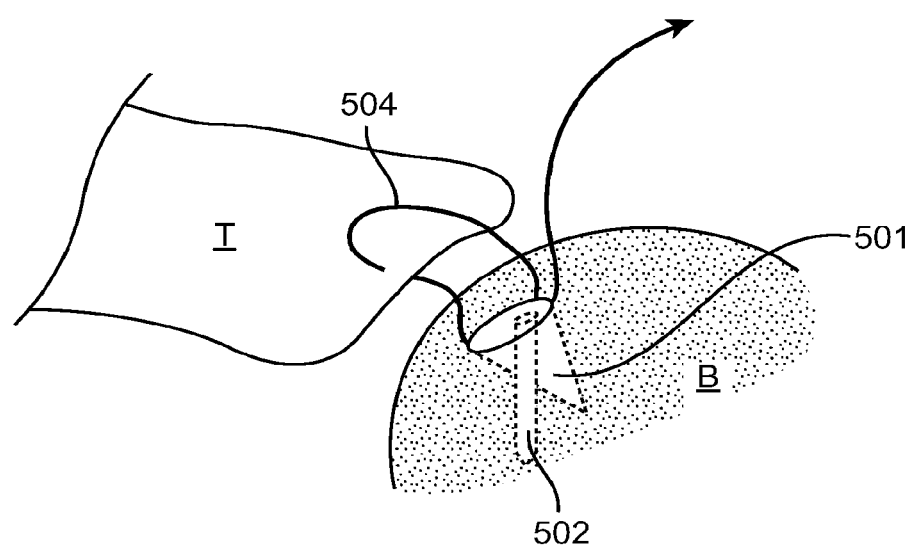

FIG. 10B shows the system with the main anchor in the bone B and the smaller anchor placed through an angled hole in the main anchor. The smaller anchor has been advanced through the tissue T and is small enough to be pushed through tissue much like a needle so as to avoid damaging the tissue. The smaller anchor is then placed in the larger anchor. In this figure the two are shown implanted into bone at an oblique angle relative to each other, thereby optimizing purchase in the bony tissue. A suture 504 is connected between the two anchors. The suture is then tensioned appropriately to provide approximation of the tissue to the bone. Once the appropriate tension in the suture has been achieved the smaller anchor 502 is moved to a final position within the larger anchor 501, and the suture is locked into position by clamping the suture between the two anchors. Other knotless cinching mechanisms may be used in either anchor as described below. Locking of smaller anchor 502 within larger anchor 501 may be achieved with detent mechanisms, a press fit or other means known in the art.

Figure 11A:
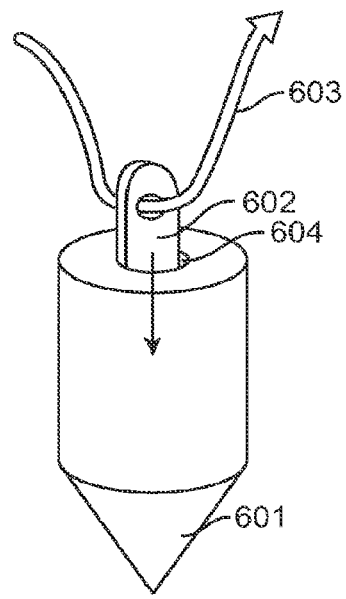
FIGS. 11A-11D show anchors with suture tensioning capabilities.
Figure 11B:
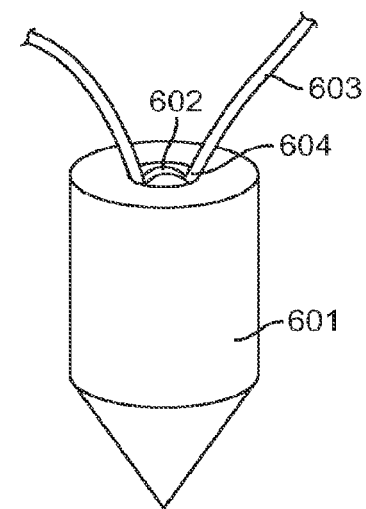

Another embodiment for anchors placed with suture tensioning capabilities is shown in FIGS. 11A-11B. This design has a fixed anchor with a slidable component that locks the suture in place after tensioning appropriately. Anchor 601 has a moveable member 602 that slides into a recess 604 in anchor 601 to lock a suture 603 in place after proper tension is achieved. FIG. 11A shows the mechanism in the unlocked position and in FIG. 11B the mechanism is locked. Moving the sliding component downward into recess 604 wedges the suture between the sliding component and the body of the anchor thereby locking the suture into position.

Figure 11C:
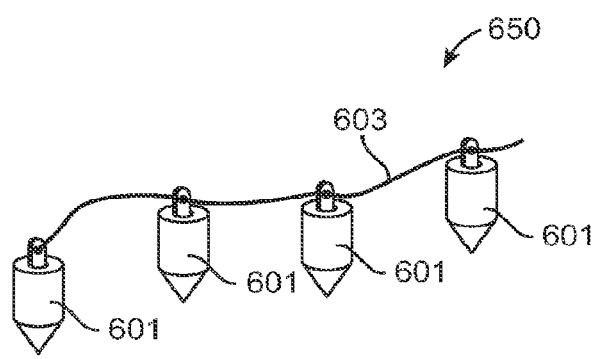
Figure 11D:
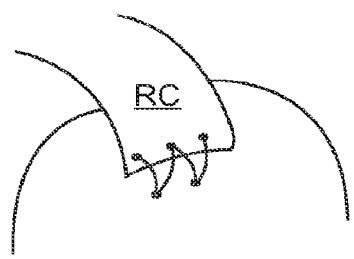

FIG. 11C shows an anchor system 650 where multiple anchors 601 are loaded on a suture with the initial anchor in the string having a fixed suture. As the anchors are placed the suture is tensioned and locked. FIG. 11D shows a rotator cuff RC or other tissue being secured using this series of anchors. A series of anchors is placed as shown and a suture runs through all of the anchors. Once the anchors have been placed appropriately the suture may be locked one by one as the surgeon adjusts tension in the suture.

In another embodiment shown in FIGS. 12A-12C, a device for temporary attachment of tissue to bone allows for locating and holding tissue, such as the rotator cuff, while permanent anchors are placed. This may be necessary for determining how much tension should be applied to the tissue or the amount of tissue to be positioned by the suture prior to permanent placement.

FIGS. 12A-12C show a temporary anchor 701. The temporary anchor may be extremely small, less than 1.5 mm, so that a more permanent anchor of 1.5 mm or greater may be placed in the same hole as the temporary anchor or adjacent the temporary anchor. The temporary anchor may have a flange or tab 704 that extends outside the bone so that it can be easily removed using a set of graspers or hook and then the permanent anchor placed. The temporary anchor includes a pre-loaded suture 702 that runs freely through a U-shaped passage 705 in the anchor, and a removable stake 703 that slides through an axial channel 706 to engage suture 702 in passage 705 to secure the suture in place after appropriate tensioning. FIGS. 12A and 12B show a simple suture and stake placement. FIG. 12C shows a cross section of the device with the stake compressing and securing the suture in place. The stake may be a press fit into the anchor body or housing, compressing or wedging the suture against the body, or the stake may have ribbed features to create a locking means against the suture and shell. After forcing the stake into the body, the exposed end of the stake also may be used to remove the assembly from the bone.

Figure 13A:
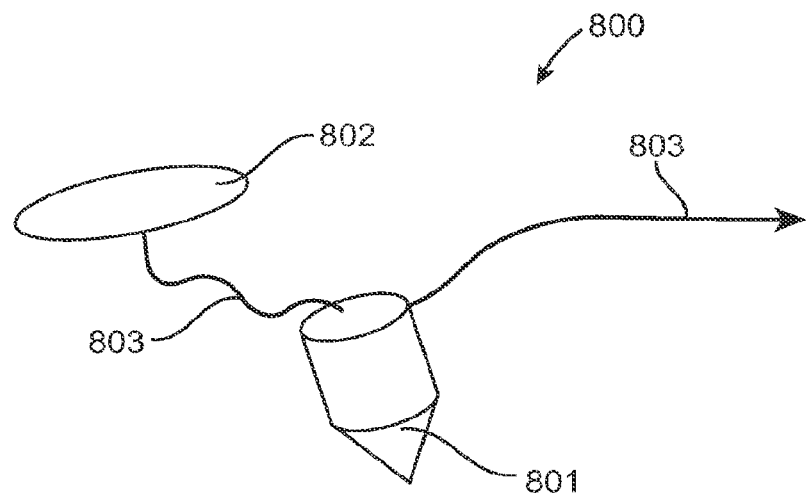
FIGS. 13A-13B show an anchor and suture tensioning system.
Figure 13B:
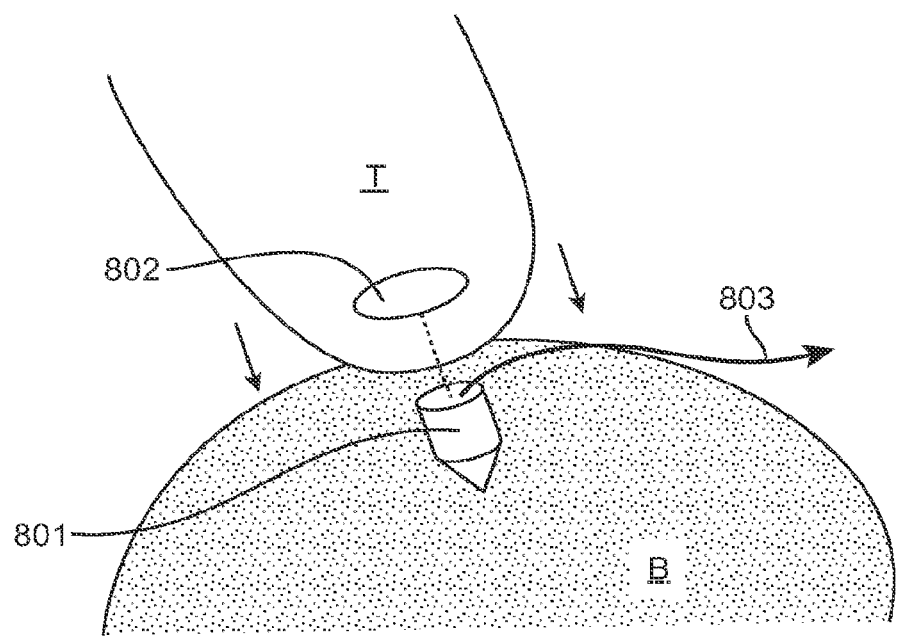

In another embodiment, FIG. 13A and FIG. 13B show an anchor and suture tensioning system 800 for approximating tissue. FIG. 13A shows an anchor system that is driven through tissue (such as the rotator cuff) into the underlying bone. The device also has a suture 803 attached with the small pad 802 attached to the end of the suture. In this embodiment the anchor 801 is placed through tissue T into bone B with a large surface area pad 802 remaining on the tissue attached to a tensioning suture 803. The small pad resides on the top of the cuff of tissue while the suture pulls the pad down towards the anchor, compressing the tissue against the bone. FIG. 13B shows a representation of this embodiment where the anchor is shown embedded in bone B and the suture extends through the tissue T to the pad positioned on the surface of the cuff. This system may also comprise a suture tensioning/locking, clamping, or cinching mechanism, such as those disclosed hereinbelow. The suture tensioning element could be located in either the anchor or in the pad.

Figure 14A:
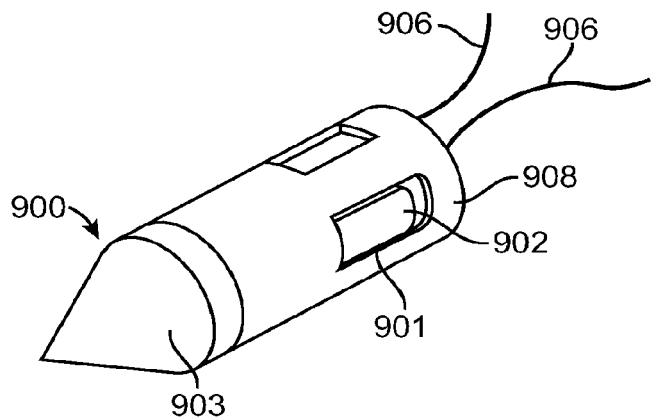
FIGS. 14A-14C show an anchor and suture tensioning and locking system.
Figure 14B:
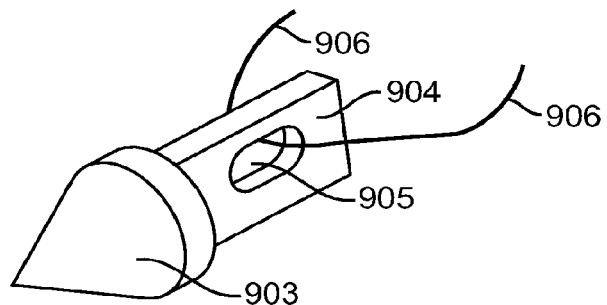
Figure 14C:
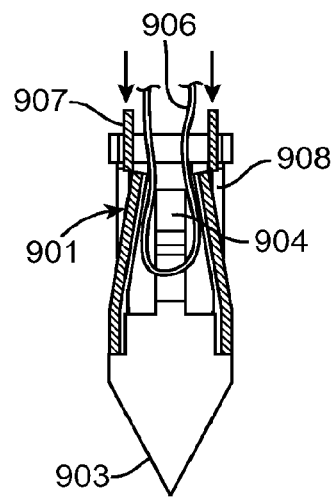

FIGS. 14A-14C illustrate a penetrating bone anchor 900 with suture tensioning and locking capability. Anchor 900 has an outer tubular member 908 which receives a penetrating anchor member 903. Referring to FIG. 14A, a pair of radially deflectable fingers 901 which are illustrated deformed radially inward 902, are integrally attached to outer tubular member 908. In FIG. 14B the penetrating anchor member 903 is shown having a stem 904 with a hole 905 to accept a suture 906 or wire. FIG. 14C is a cross section of the assembly showing a suture 906 loaded through the anchor member. As a driver 907 is forced down into the outer member 908, the driver deforms the fingers 901 inward to clamp the suture between the fingers 901 and the anchor stem 904, thereby preventing suture movement and maintaining adequate suture tension.

Figure 15A:
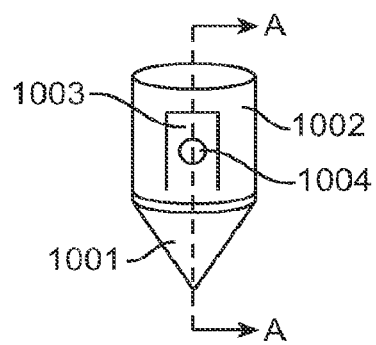
FIGS. 15A-15D show a suture wedge lock system for securing sutures in an anchor system.
Figure 15B:
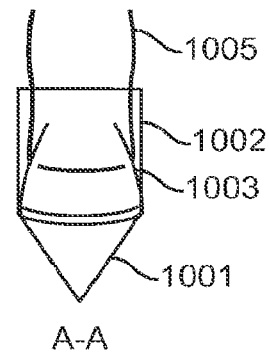
Figure 15C:
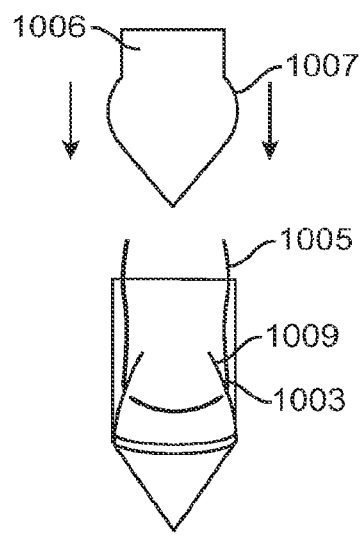
Figure 15D:
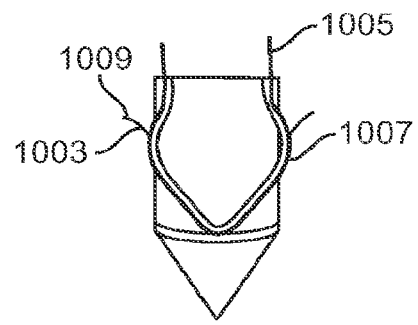

In another embodiment a suture wedge lock system has an additional function for locking the anchor under the cortical shelf within a cancellous region of bone, such as in the head of the humerus. FIG. 15A shows a penetrating anchor 1001 and an outer member 1002 with deformable cutouts 1003. The cutouts have holes 1004 to accept a suture or wire 1005 shown in FIG. 15B. FIG. 15C shows a wedge-like member 1006 with the ability to wedge itself into the outer member 1002 as shown in FIG. 15D. In FIG. 15D the wedge 1006 locks the suture in place against the cutouts 1003 and because of the bulbous shape of the lateral edges 1007 of the wedge 1006, the deformable cutouts 1003 move radially outward so that their proximal ends 1009 extend beyond the outer wall of the anchor. This locks the suture in position, and also helps secure the anchor to the bone. When this anchor system is placed below the cortical shell of a bone and within the cancellous region of the bone, the cutouts 1003 engage the cortical shell, preventing the anchor from pulling out of the bone.

Figure 16A:
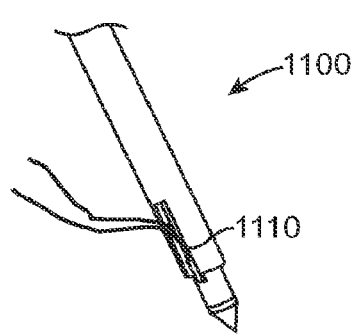
FIGS. 16A-16G show a suture locking anchor.
Figure 16B:
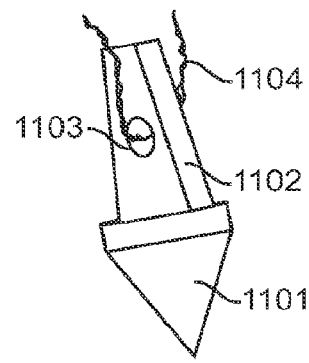
Figure 16C:
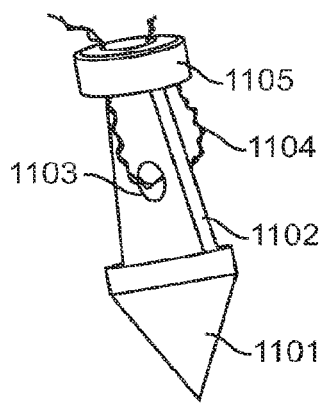
Figure 16D:
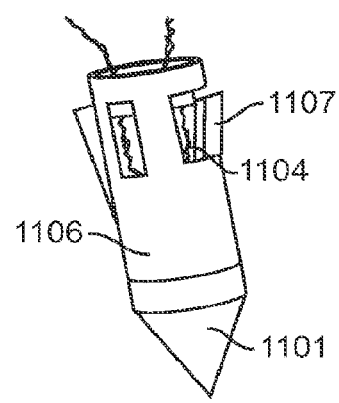

FIGS. 16A-11G illustrate a suture anchor having a locking mechanism for securing the suture. In this embodiment, the suture anchor has an inner member 1101 with a tapered shaft 1102 having a through hole 1103 transverse to the shaft's longitudinal axis. The through hole is sized to accept a length of suture 1104. The suture may be pre-loaded or it may be loaded during a surgical procedure using a wire or other means to thread the suture through the hole 1103. In use, the suture 1104 is threaded through a donut shaped member 1105 that is welded or otherwise attached to the outer member 1106 of the assembly (removed for clarity in FIG. 16C). When the anchor is placed, the operator will tension the suture appropriately, and then lock the suture in place by advancing a pusher tube against the donut, breaking the weld or other attachment. As the pusher tube continues to be advanced, the donut is forced further toward the tip of the anchor and the suture becomes locked between the tapered shaft 1102 of the inner member 1101 and the donut 1105. FIG. 16A shows the anchor system 1100 loaded into a delivery device. FIG. 16B shows the anchor 1101 with a tapered shaft 1102 and a central hole 1103 through which the suture 1104 passes. FIG. 16C shows a donut 1105 being placed over the tapered shaft of the anchor. The suture runs between the donut and the tapered shaft. FIG. 16D shows the outer anchor body 1106 placed over the donut and the tapered anchor 1101. Wings 1107 on the outer member 1106 protrude radially outward, and may be forced outward as the donut 1105 is advanced along the tapered anchor shaft 1103. The wings may be used to help engage the anchor with the cortical shell of bone, as described above. The donut 1105 is welded by heat, adhesives or the like to the outer anchor body 1106.

Figure 16E:
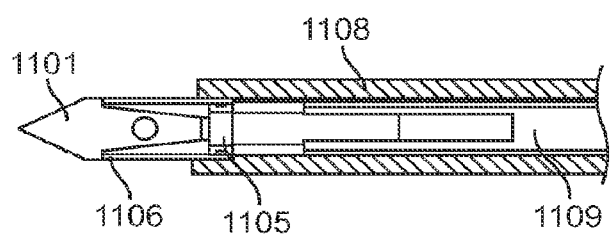
Figure 16F:
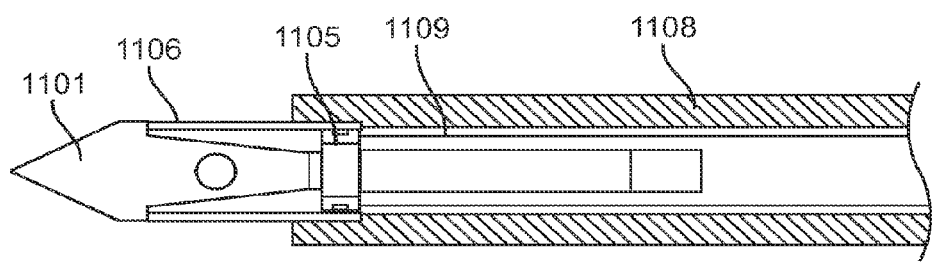
Figure 16G:
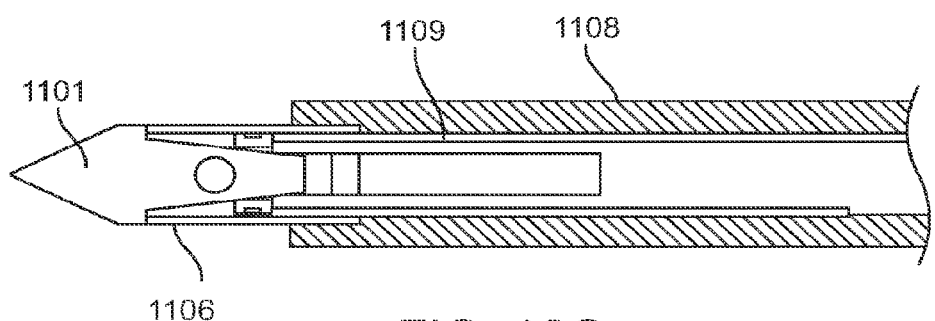

FIGS. 16E through FIG. 16G show a cross section of the final assembly and the operation of the delivery instrument. FIG. 16E illustrates a cross section of the delivery instrument used to place the suture anchor, often in bone. An external shaft 1108 holds the anchor 1101 and a driver tube 1109 may be advanced against the donut. The suture runs through the cutout 1110 (FIG. 16A) on the external shaft 1108. When the suture is tensioned appropriately, the internal driver tube 1109 will force donut 1105 distally, breaking the weld as shown in FIG. 16F and capturing and locking the suture as the donut locks on the shaft as shown in FIG. 16G.

Figure 17A:
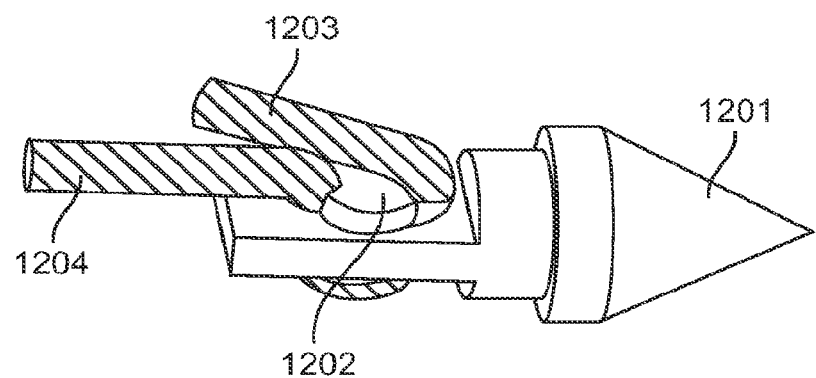
FIGS. 17A-17B show a suture locking mechanism.
Figure 17B:
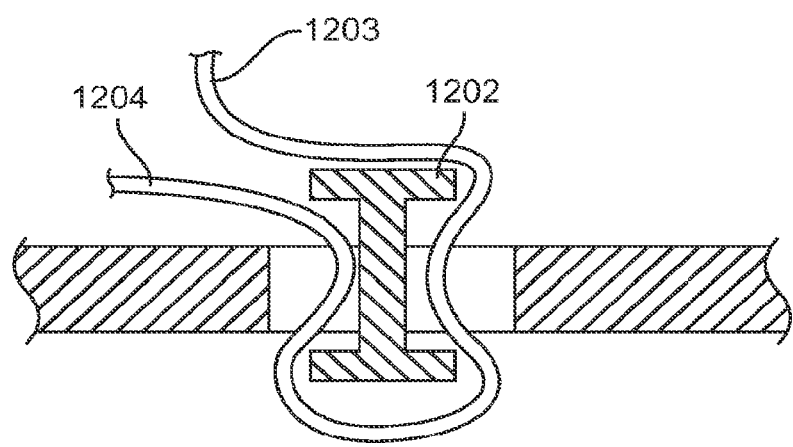

FIGS. 17A-17B illustrate another embodiment of a suture anchor having a suture locking mechanism. FIG. 17A is a perspective view of the suture anchor and FIG. 17B shows a cross section of the locking mechanism. In this embodiment, the locking mechanism uses a floating suture locking mechanism within the anchor body. The suture 1203, 1204 is threaded through the floating locking bar 1202 such that it is activated by pulling one end of the suture to engage the lock. When the other end is tensioned, the lock can release providing adjustable tensioning capabilities. The main body of the anchor 1201 is configured to receive a sliding locking bar 1202. As tension on the suture thread end 1203 is increased the sliding member is pulled proximally locking the suture in position. When tension is exerted on thread end 1204 the system remains free to move and the suture slides. The floating member 1202 can be constructed of a different material than the anchor, such as a compressible material like a soft durometer polymer such as silicone or urethane. With a softer, compressible material the suture could become locked as the material compresses around it during tensioning. In addition, the floating lock could be molded with a variety of surface features to cause a more secure lock, similar to a cleat found on sailboats.

Figure 18:
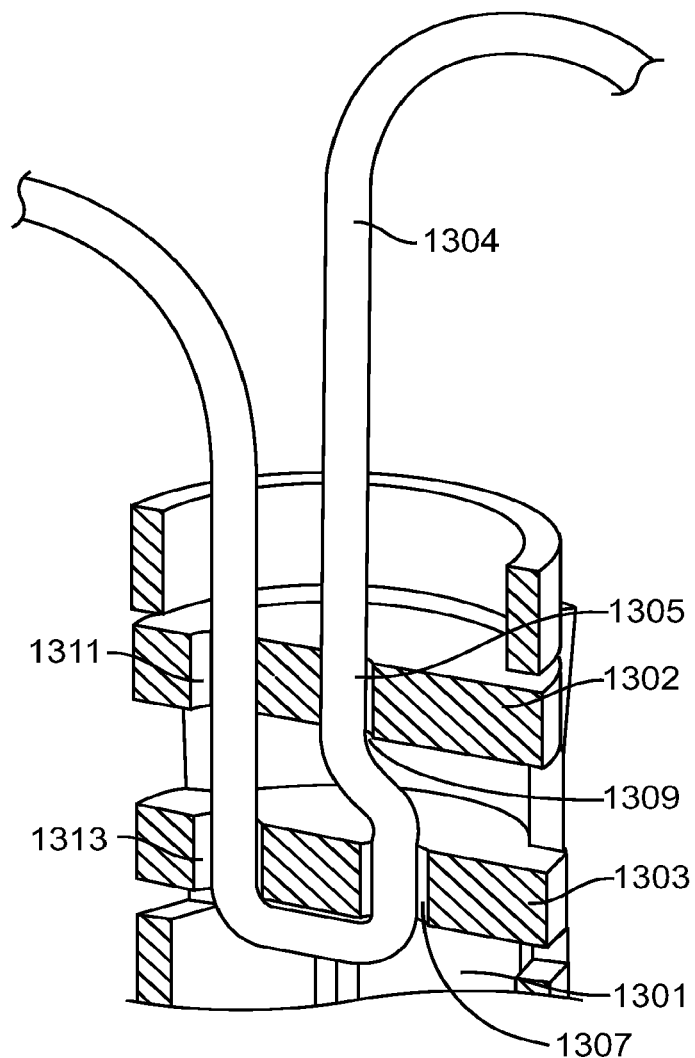
FIG. 18 shows an additional suture locking mechanism.

FIG. 18 illustrates still another embodiment of a suture anchor with locking mechanism, shown in cross section. In FIG. 18, an outer tube 1301 contains a fixed element 1302 with a pair of holes 1305, 1311 and an axially slidable member 1303 with a pair of holes 1307, 1313 that lock against the fixed member when one end of a suture 1304 is tensioned. Because hole 1305 in the fixed element 1302 is radially offset from hole 1307 in sliding member 1303, a portion of suture 1309 is trapped between the fixed element and slidable member when suture end 1304 is tensioned, locking the suture. If the opposite end of the suture is pulled, because hole 1311 is axially aligned with hole 1313, the suture will slide through the slidable member and fixed element without trapping the portion of suture 1309 against the fixed element. In some embodiments, the slidable member 1303 may also be positioned on a helix-like track so that more positive locking occurs as the slidable member moves axially and rotationally along the tube axis.

Figure 19A:
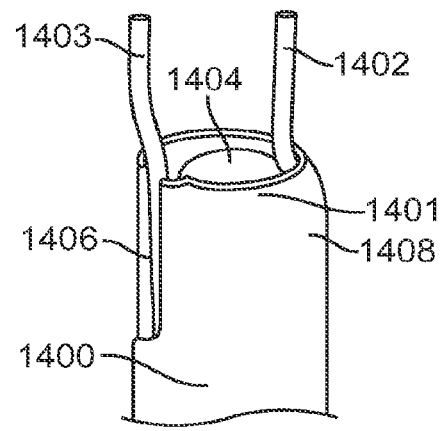
FIGS. 19A-19B show an additional suture locking mechanism.
Figure 19B:
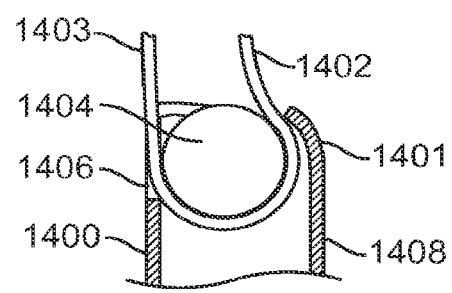

FIGS. 19A-19B illustrate another embodiment of a suture anchor having a locking mechanism. Suture anchor 1400 includes a ball 1404 that is axially movable within a tubular body 1408 and captured by a swaged head 1401. Suture 1402, 1403 is wrapped under the ball and the ball 1404 allows the suture to move in the direction of suture end 1403, while locking the suture when pulled in the direction of suture end 1402. When suture end 1402 is pulled, the ball is pulled up against the swaged end 1401 trapping the suture between ball 1404 and body 1408 and preventing further movement. When the opposite suture end 1403 is pulled, a cutout 1406 in the sidewall of body 1408 near swaged end 1401 allows the suture to be advanced without pinching it between the ball and the swaged end of the anchor, thus the suture may be tensioned. A groove in the ball may be provided to maintain the suture position relative to the cutout 1406.

Figure 20A:
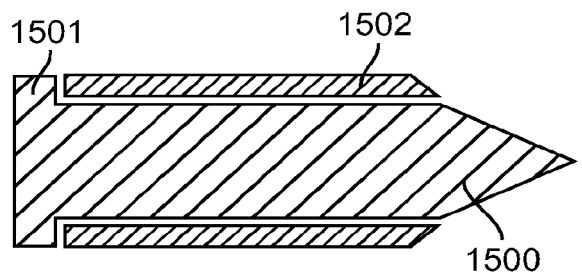
FIG. 20A shows an exemplary embodiment of a suture anchor.
Figure 20B:
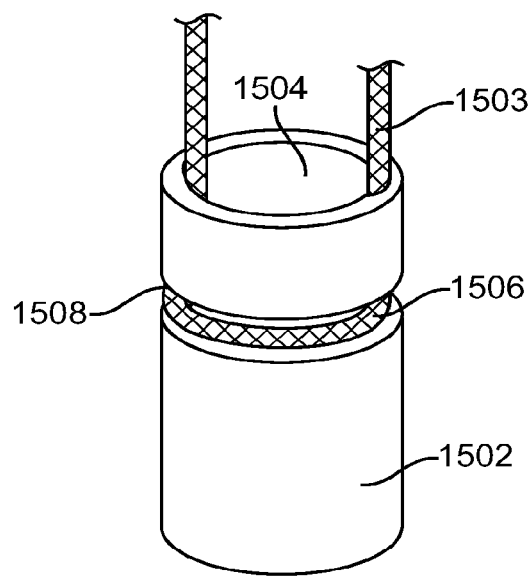
FIG. 20B illustrates a suture locking mechanism.
Figure 20C:
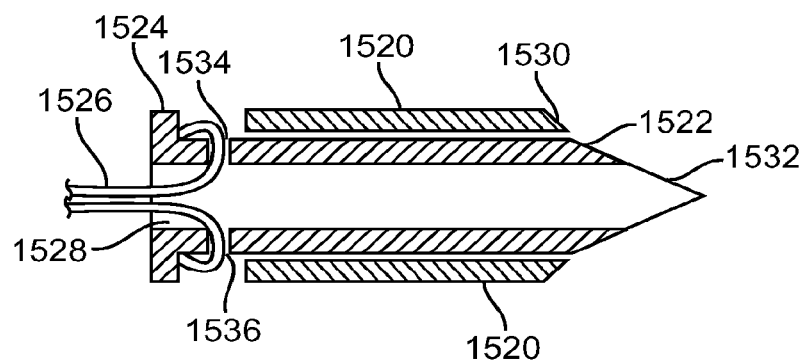
FIG. 20C illustrates another embodiment of a suture anchor and locking mechanism.

FIGS. 20A-20B illustrate an alternative embodiment with a core 1500 with a flange 1501 on its proximal end. Core 1500 is positionable in an anchor sleeve 1502 adapted to be driven into bone or tissue. Core 1500 may have a friction fit in sleeve 1502 or a locking mechanism may be provided to retain the core 1500 in sleeve 1502. Additionally, the flanged region 1501 may be used to help drive the anchor 1502 into the bone. Core 1500 and sleeve 1502 may be driven in to bone together, or sleeve 1502 may be driven in first separately. FIG. 20B illustrates securing the suture to the anchor. The ends of suture 1503 extend through a central channel 1504 of the anchor sleeve and then pass through apertures 1506, 1508 in the sidewall of the anchor sleeve such that the suture forms an outer loop around the outer surface of the anchor sleeve 1502. Suture 1503 is locked by being trapped between the proximal end of sleeve 1502 and core 1500 when the core 1500 is pressed distally into central channel 1504. FIG. 20C illustrates an alternative embodiment of a suture anchor having an inner core 1522, and outer anchor sleeve 1520 and suture 1526 Inner core 1522 has a pointed distal tip 1532 that can penetrate bone and a flanged region 1524 and apertures 1534, 1536. Outer sleeve 1520 also has a pointed distal tip 1530 that is adapted to penetrate bone. The inner core 1522 is sized to fit in the outer core 1520. Either the inner core 1522 or the outer sleeve 1520 may be driven into bone individually or simultaneously. Flange 1524 provides a shoulder which may be used to help drive the outer sleeve 1520 into the bone. A locking mechanism (e.g. detents, press fit, snap fit, etc.) may be used to lock the inner core 1522 with the outer sleeve 1520. The suture 1526 is secured to the inner core 1522 by passing through a central channel 1528 in the inner core 1522 and then exiting the inner core through apertures 1534, 1536 in the wall of the inner core 1522. The suture 1526 then is partially looped around the outer surface of inner core 1522. When the inner core 1522 and the outer sleeve 1520 are locked together, the suture 1526 will be trapped between the flange 1524 and the proximal end of the outer sleeve 1520, securing it in position.

Any of the embodiments disclosed herein may also be used for drug delivery. The suture and/or the suture anchor may be coated with or carry a therapeutic agent that can be released in a controlled manner. For example, the therapeutic agent may be time released and eluted into the bone or affected tissue in order to enhance healing. Multiple medicaments may be impregnated into or coated onto the anchors in a similar fashion as stents. Examples of coatings that produce a sustained-release are those made by SurModics Corporation and Angiotech. Examples of medicaments that could be eluted are anti-inflammatory medicaments, NSAIDs (non-steroidal anti-inflammatories), and hyaluronic acid. Stem cells or other bone or cell growth promoters may also be used in such coatings.

Some of the suture anchors may be fabricated from durable metals such as stainless steel, titanium or nitinol. Alternatively, a variety of polymers may be used. It would also be desirable to provide anchors that bioerode away after some period of time. Thus, any of the embodiments disclosed herein may be fabricated from bioerodable polymeric materials. Combinations of durable metals or polymers and bioerodable polymers may also be used and similarly bioerodable sutures and durable sutures may also be used. In an exemplary embodiment, a bioerodable anchor may be loaded onto a delivery core made from stainless steel or titanium. The anchor is driven into the bone and then the core is removed, leaving the anchor permanently implanted. The anchor has a suture attached and can be tensioned using any of the locking mechanisms described herein. The anchor may be fabricated from polymers such as PEEK or PMMA and polymers that are well known for bioerosion include PGA, PLGA, and PLA.

Figure 21:
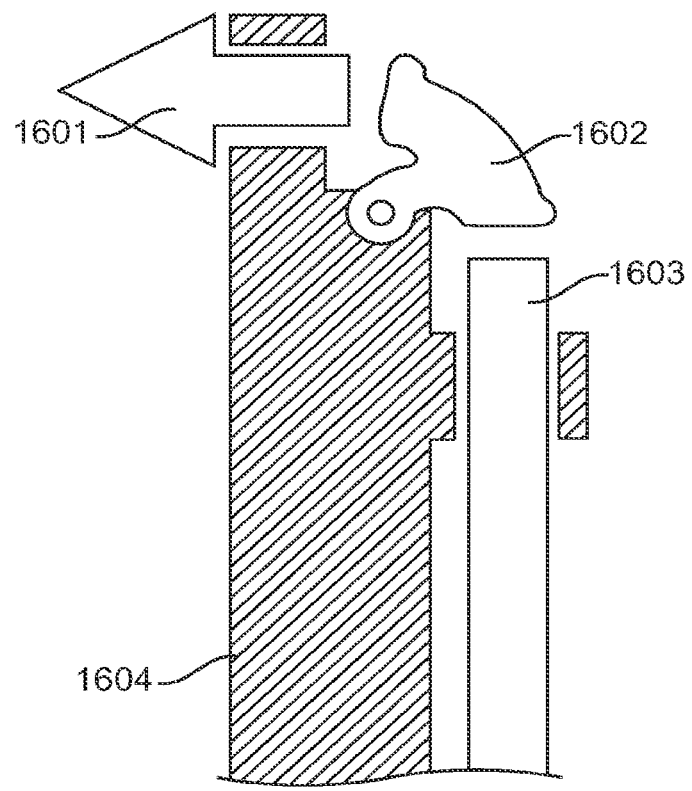
FIG. 21 shows a right angle driver for driving bone anchors.

FIGS. 21-22, 23A-23B, 24, and 25A-25B schematically illustrate several exemplary embodiments of instruments for delivering the suture anchor and driving the anchor into tissue such as bone. The anchors delivered using such instruments may be any of the embodiments illustrated herein or other commercially available anchors. FIG. 21 illustrates an embodiment with a low profile right angle driver for driving one or more suture anchors into bone. The need for a right angle driver occurs when the angle of attack for placing an anchor arthoscopically prohibits a straight approach as is often the case with labral repair in the hip. In FIG. 21, an anchor 1601 is held at a perpendicular angle relative to the longitudinal axis of the delivery instrument 1604. A hammer or striker 1602 pivotably connected to the instrument shaft 1604 is used to transfer energy to anchor 1601 from an axially movable impacting member 1603 that can be driven manually or by a pneumatic or hydraulic cylinder or other known means. This embodiment may be used to drive a single anchor or it may be easily adapted to include multiple strikers so that two or more anchors may be driven individually or simultaneously into the bone. In order to reduce profile of the instrument, when driving multiple anchors the instrument preferably has a hinge or other articulation that allows the two drivers to move closer together for access and then spread apart within the body prior to impaction of the anchors. While a 90 degree driver is shown, various other angles transverse to the longitudinal axis of the delivery instrument 1604 are also possible.

Figure 22:
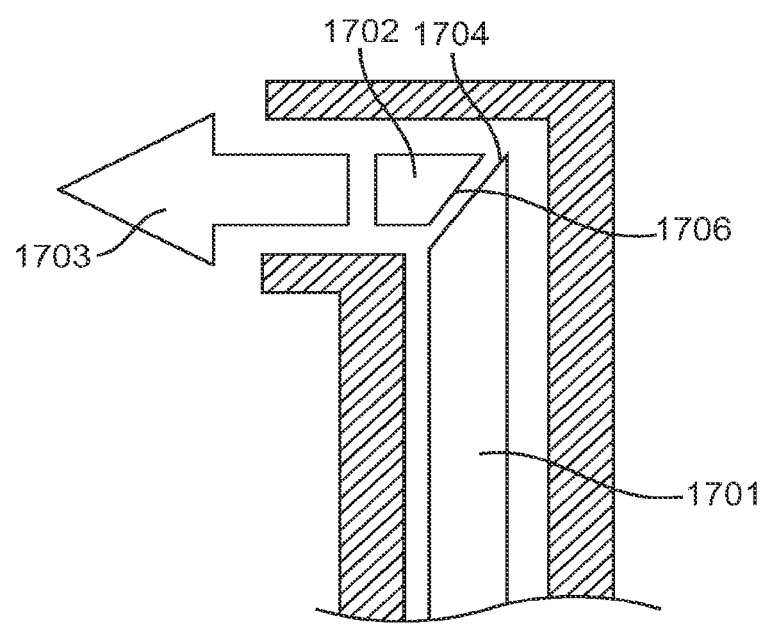
FIG. 22 shows an angled driver for driving bone anchors.

FIG. 22 illustrates another embodiment of an angled anchor driver. In this embodiment the distal end 1704 of the hammer or impacting member 1701 is angled to form a wedge that impacts striker 1702, which has the corresponding angle on its proximal end 1706 to interface with impacting member 1701. Thus, as impact member 1701 moves axially, it drives the striker 1702 down at a right angle to impact member 1701 and into anchor 1703. In the embodiments of FIGS. 21-22, the instrument is adapted to drive an anchor into bone or other tissue at a 90 degree angle relative to the longitudinal axis of the delivery instrument. One of skill in the art will of course appreciate that this angle may be varied depending on the anatomy. Thus in still other embodiments, the distal region of the delivery instrument may be articulated so that the delivery angle can be varied. In still other embodiments, interchangeable tips may be used having predetermined angles ranging from 0 degrees to 90 degrees. Still other embodiments may have actively steerable tips that may be controlled from the proximal end of the device outside of the patient.

FIGS. 23A-23B illustrate still another embodiment of a delivery instrument 1800. FIG. 23A shows a front view of a rotating shaft 1801 that is operably coupled with a head 1802. The head is eccentrically attached to the rotating shaft

1801. Thus, as the shaft 1801 rotates and spins the head 1802, the head contacts a driver 1803 that moves linearly in a direction transverse to shaft 1801 to impact an anchor 1804. The driver may be spring loaded or may simply be forced back after impacting the anchor to the original position for the next impact from the mass. The instrument 1800 will usually include an outer housing or tubular shaft (removed for clarity) enclosing shaft 1801 and operatively coupled to driver 1803 and anchor 1804.

FIG. 24 schematically illustrates a pneumatically driven impactor. One advantage of this embodiment over conventional pneumatically driven tools is that it has much lower vibration as compared with standard air tools. The impactor contains two pistons 1901 and 1902 that move axially in opposite directions as air is introduced into the chamber 1903. The pistons move at equal velocities in opposite directions. Piston 1901 drives the anchor 1906 via a driver 1904 while the piston 1902 simultaneously impacts the opposite end of the chamber, thereby providing a counter force to the force required to drive in the anchor. After impact the pistons are pushed by springs (not shown) or vacuum back to the center of the chamber 1903 and the process is repeated. Dampening springs or materials may be placed at one or both ends of the chamber to further decrease excessive or extraneous vibrations. In addition, size, weight, or materials of the pistons may be the same or different depending on the amount of vibration that must be eliminated. In preferred embodiments, the pistons are identical, however, different driving forces may necessitate different masses as well as different dampening materials. Pistons of different masses traveling at different distances and different speeds may be used to dampen each other as well. Any of these pneumatic embodiments may be operated at different frequencies for different applications, e.g., hip labrum repair versus rotator cuff repair in the shoulder. In addition, this dual piston driver arrangement may be used in the right angle instruments disclosed elsewhere herein.

Figure 25A:
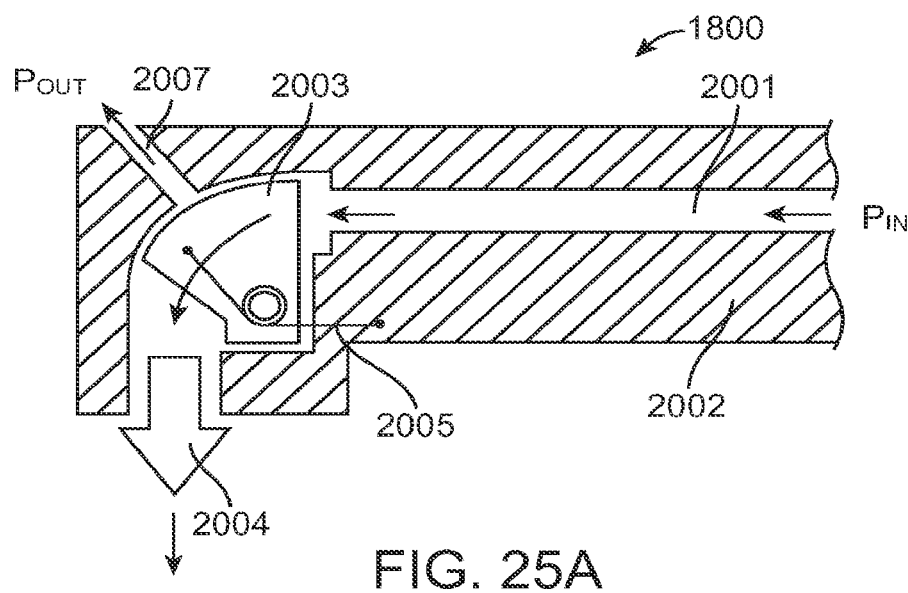
FIG. 25A-25B show alternative embodiments of a pressure driven impactor for driving bone anchors.
Figure 25B:
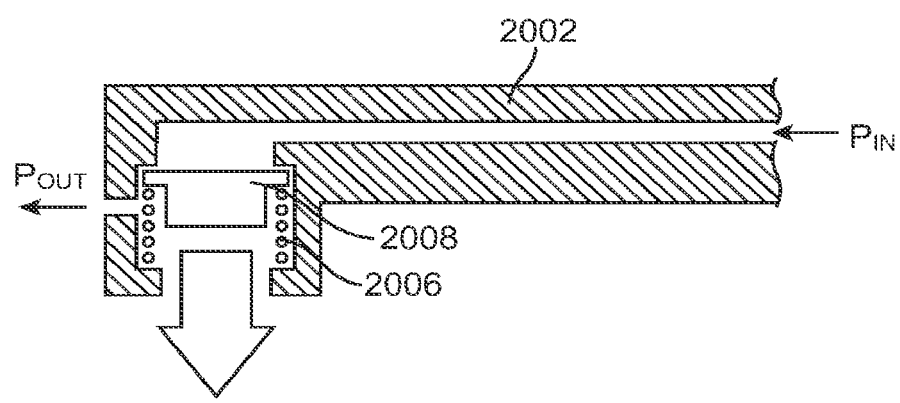

FIG. 25A illustrates another pressure driven impactor. FIG. 25A is a cross section of the impactor device 2000, which may be actuated using high pressure gas such as nitrogen. The gas flows through a channel 2001 contained within shaft 2002 shown as Pm in FIG. 25A. The pressure in channel 2001 moves a driver 2003 pivotably coupled to shaft 2002 to impact the anchor 2004 at an angle transverse to shaft 2002. When driver 2003 travels the full distance, it moves past an exhaust orifice 2007 and gas is exhausted through Pout. Torsion spring 2005 forces the driver 2003 back to the initial position. By varying the dimensions of the driver, the velocity of the driver can change creating different forces on the anchor. Additional porting and/or use of vacuum can create different frequencies and dampening within the driver chamber which would eliminate the need for or enhance the spring function. FIG. 25B is a cross section of an alternative gas pressure-driven embodiment in which a linearly movable driver 2008 transverse to shaft 2002 is used instead of pivotable driver 2003. A compression spring 2006 is used to return the driver 2008 to the original position.

Figure 26A:
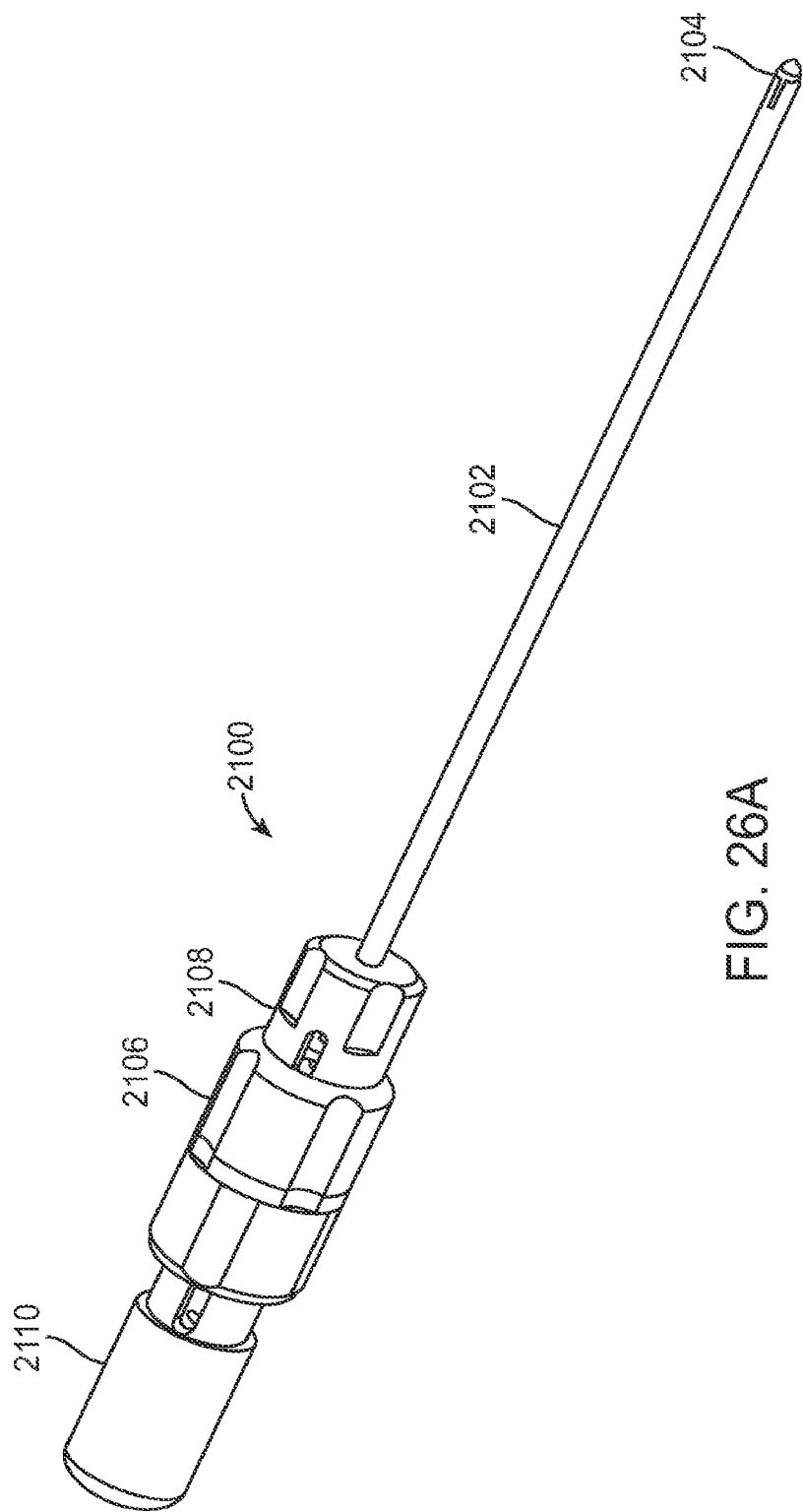
FIGS. 26A-26O illustrate an exemplary embodiment of a suture anchor system having a cinching mechanism.
Figure 26B:
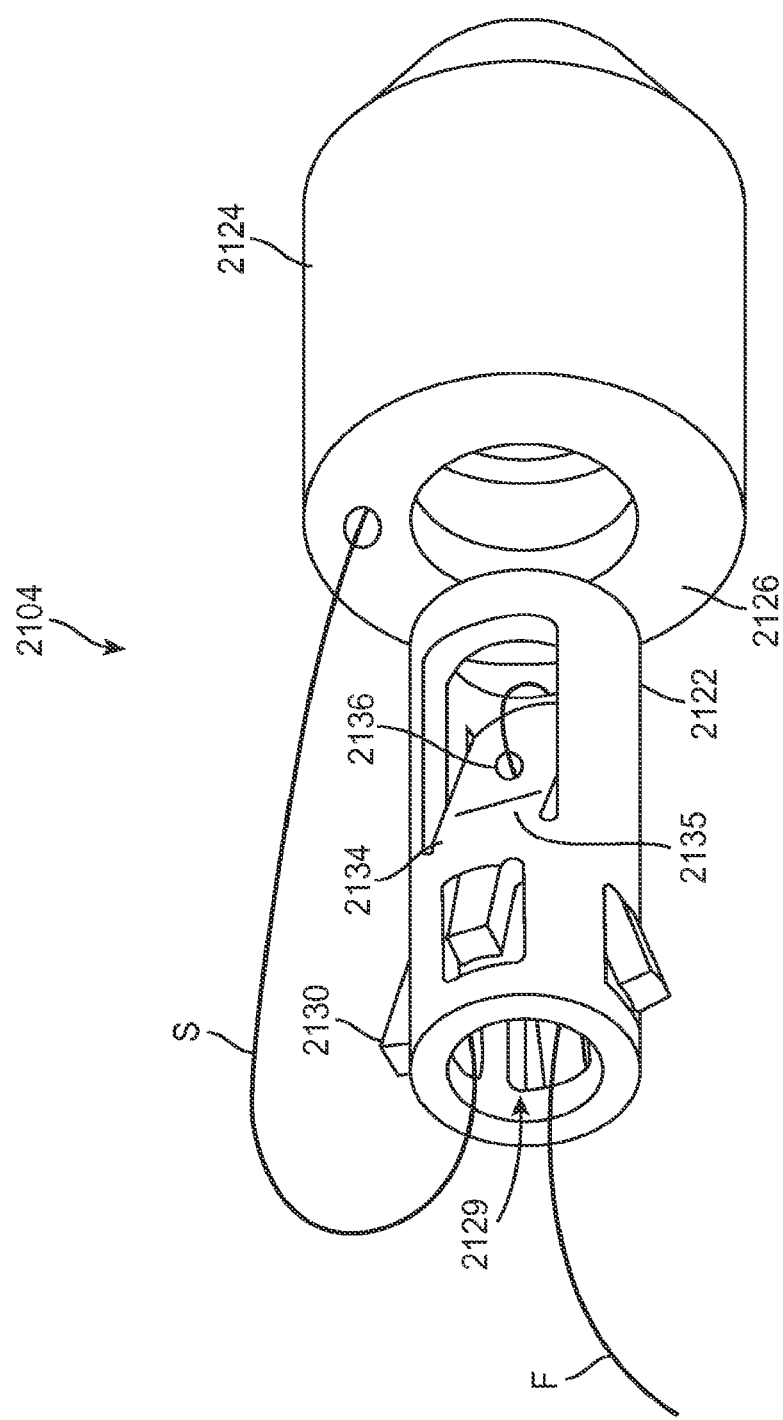
Figure 26E:
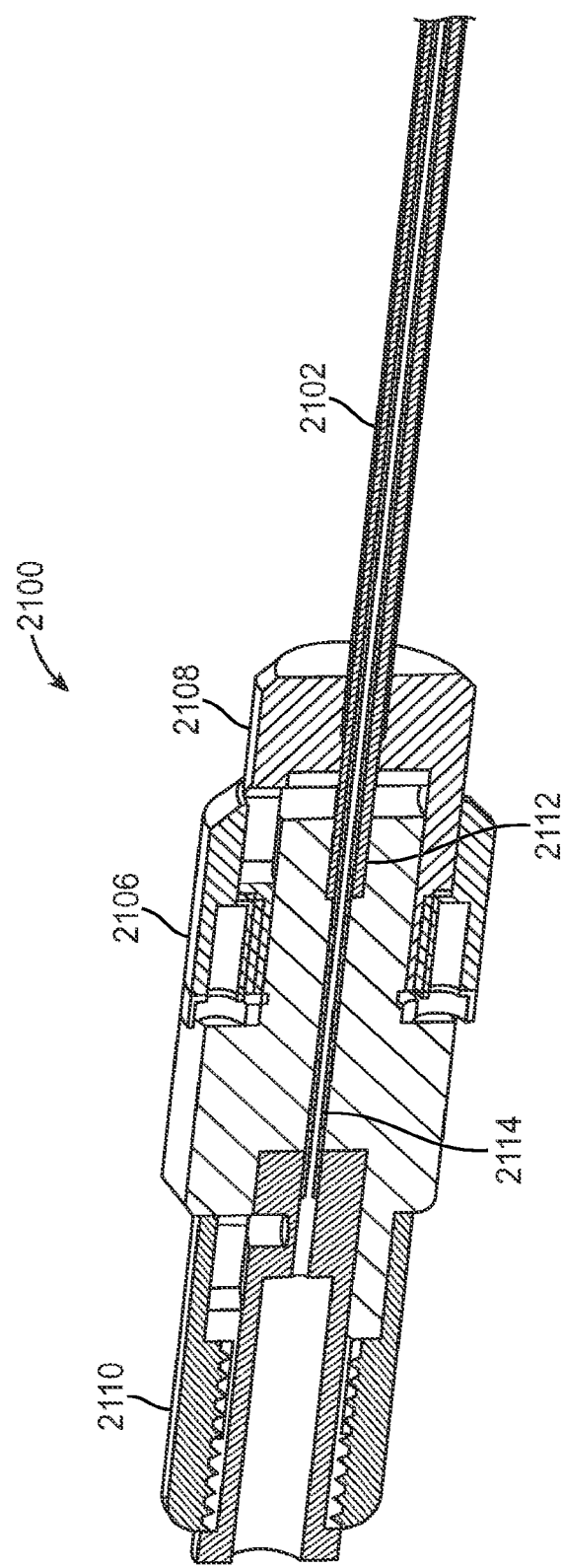
Figure 26G:
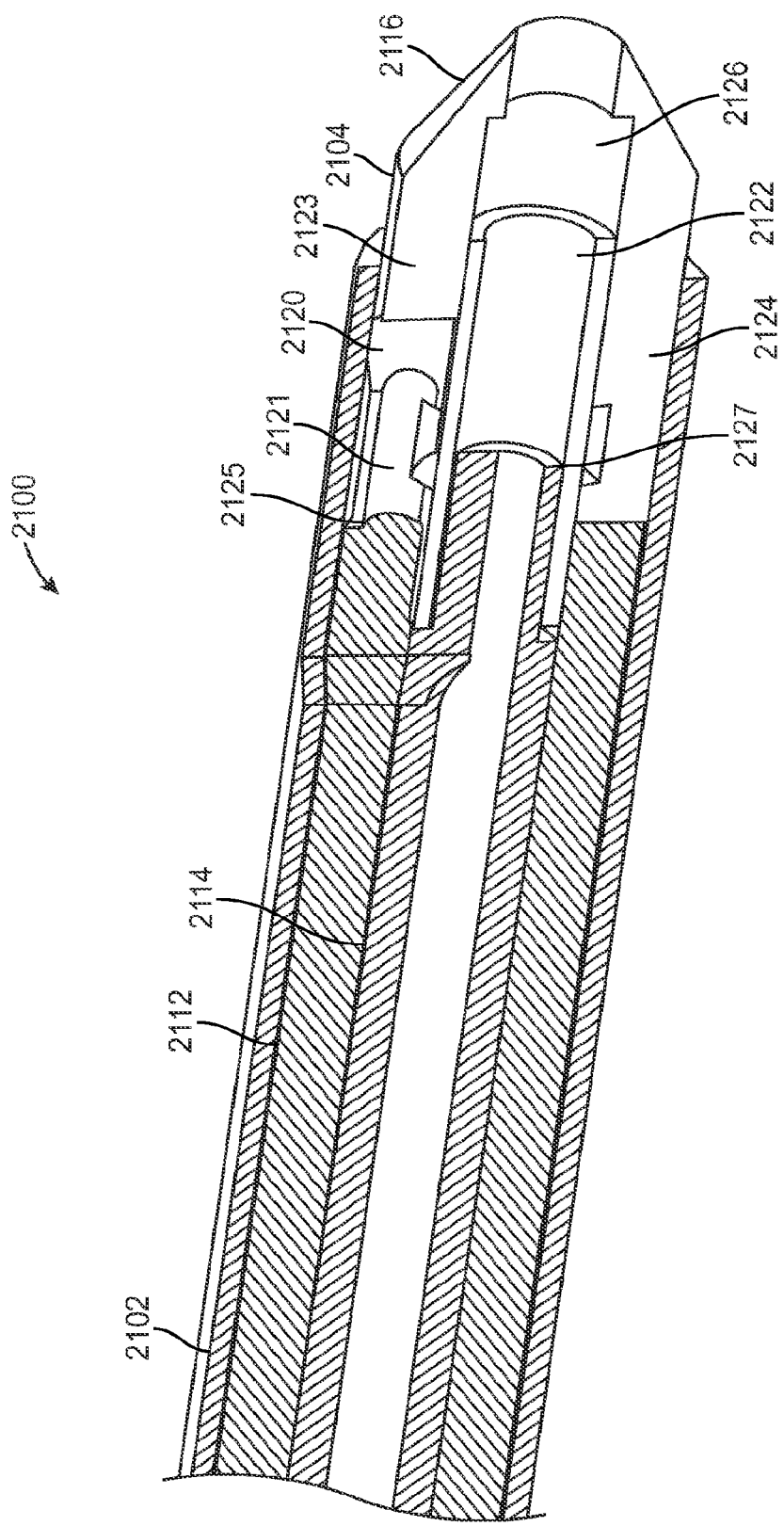
Figure 26H:
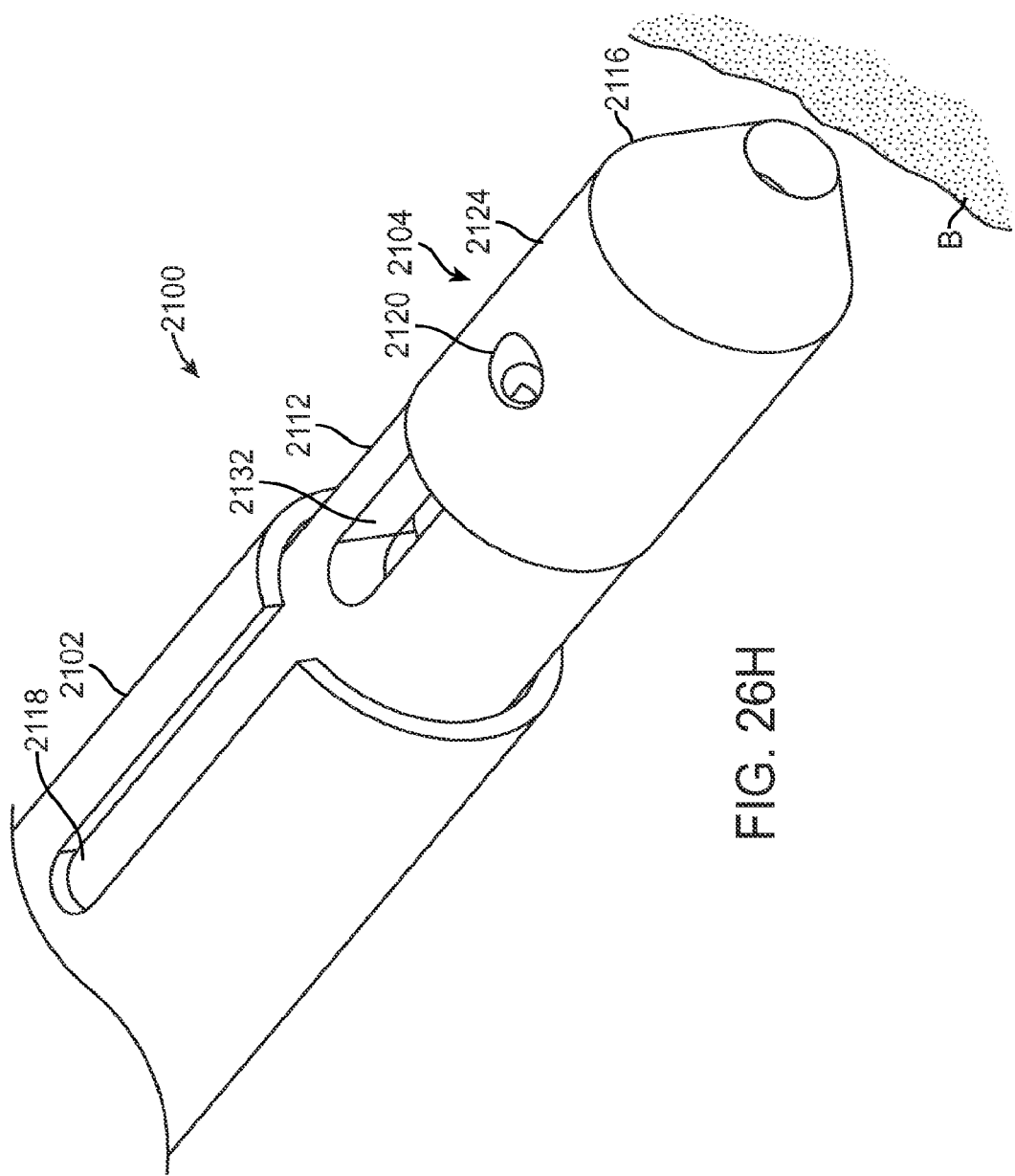
Figure 26I:
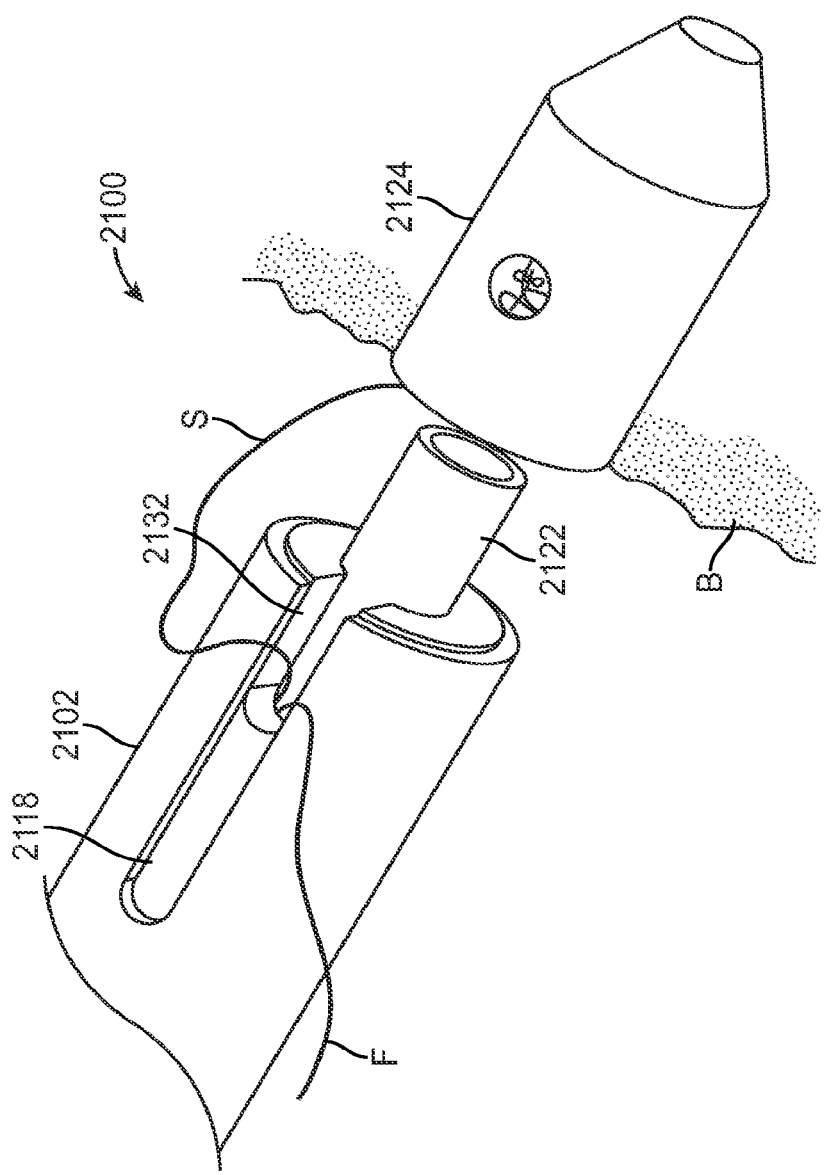
Figure 26J:
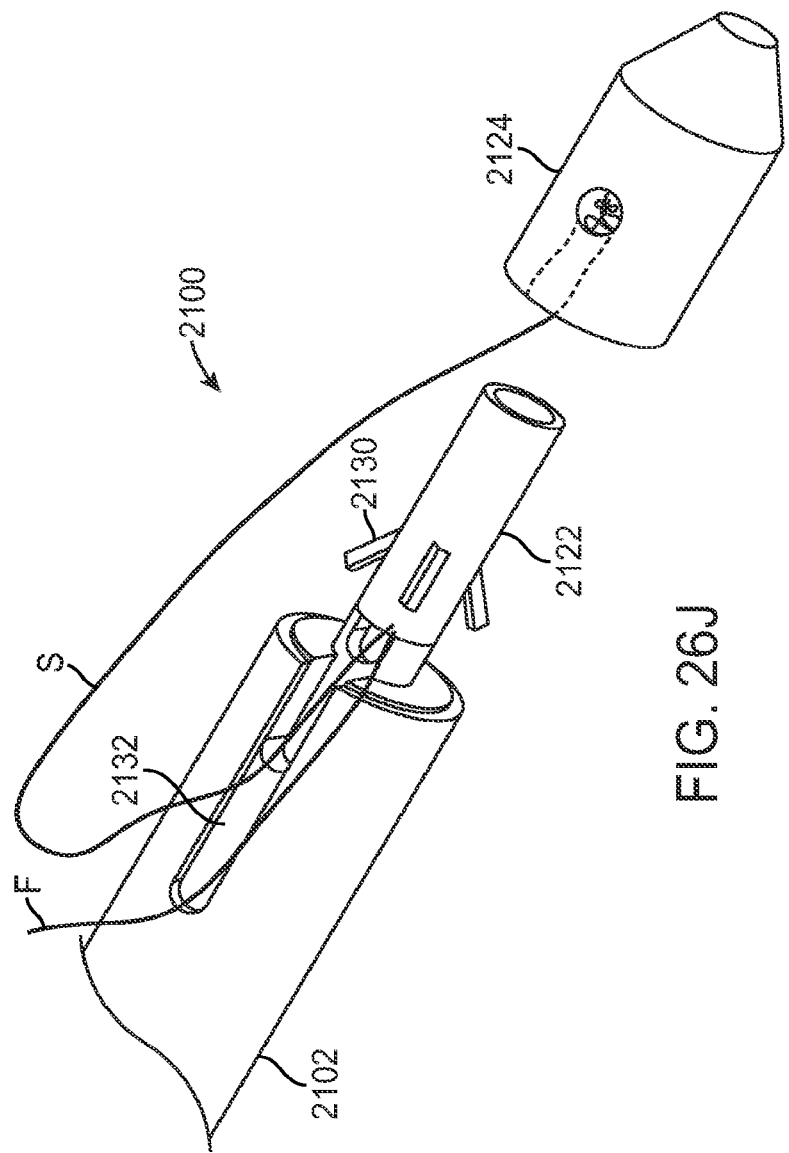
Figure 26L:
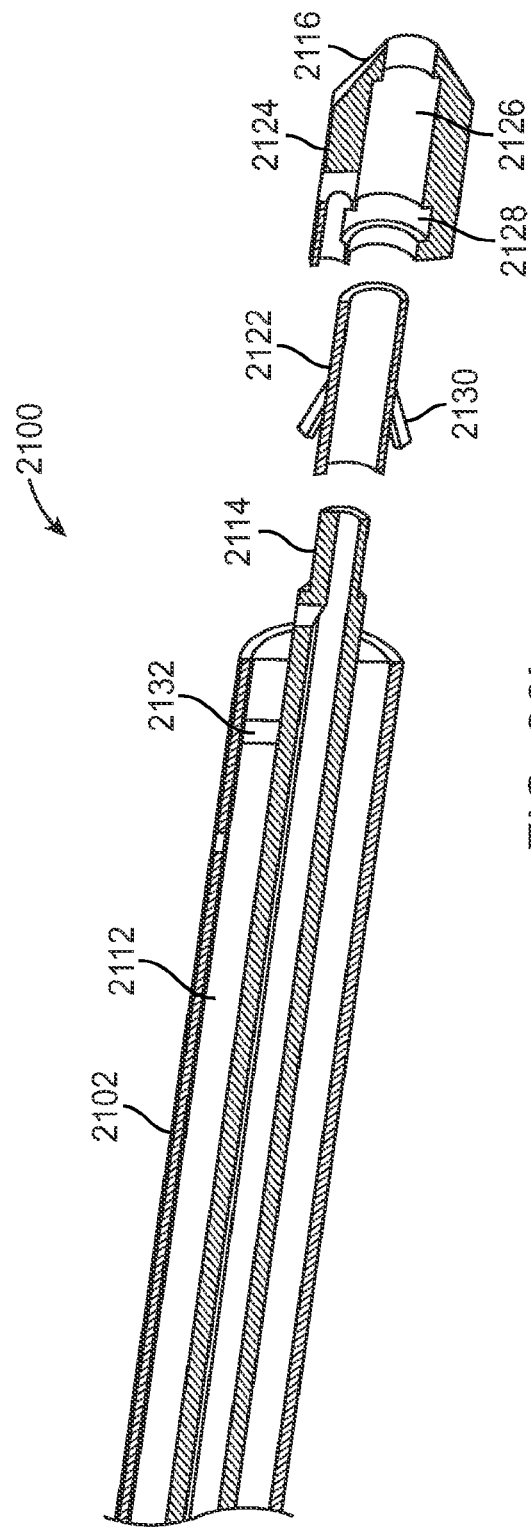
Figure 26M:
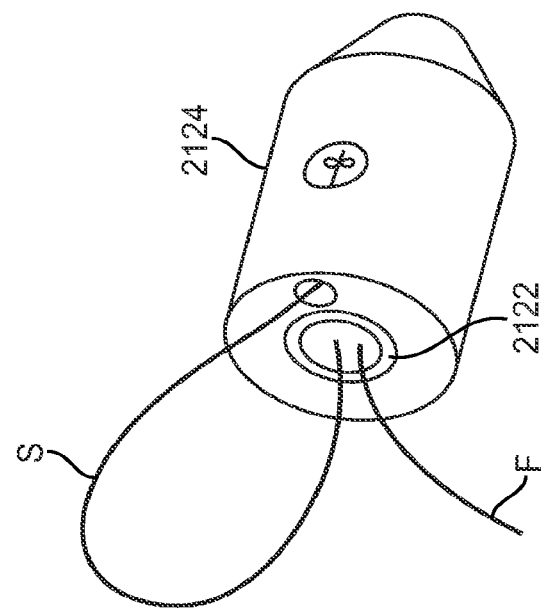
Figure 26M:
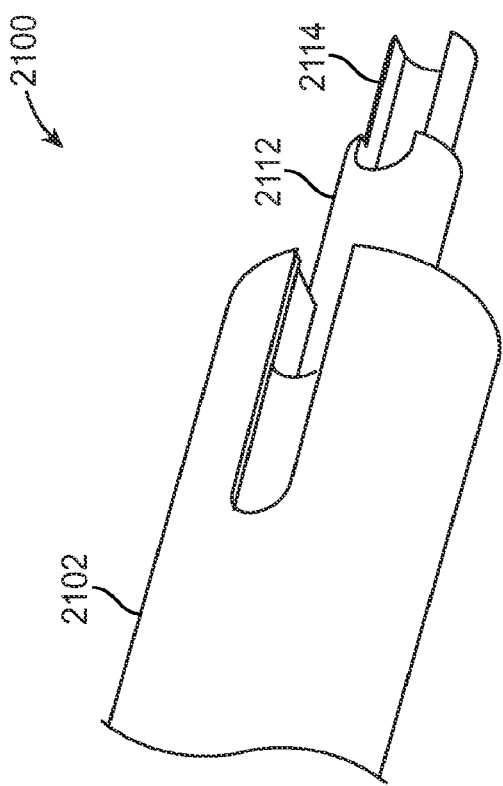
Figure 26N:
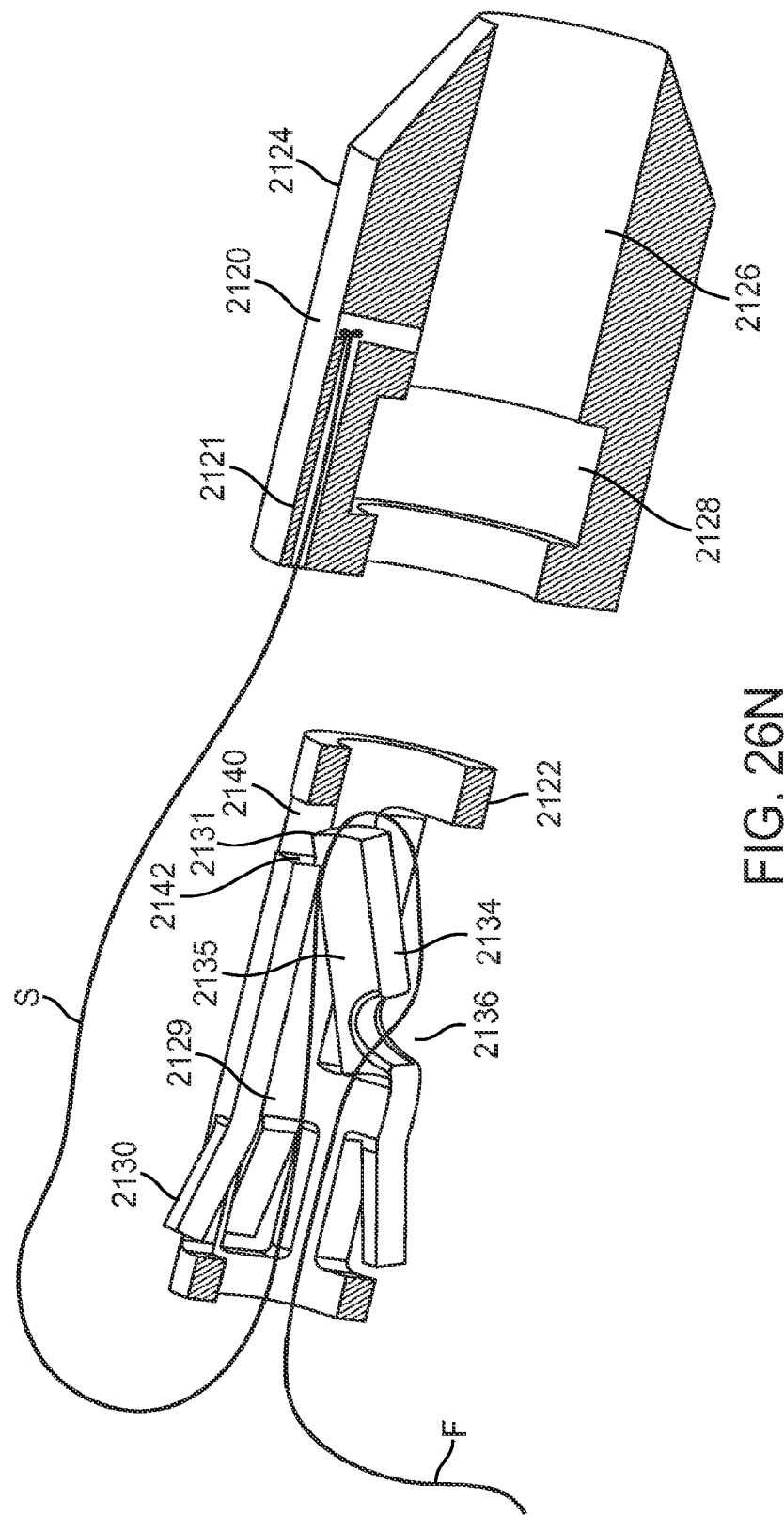
Figure 26O:
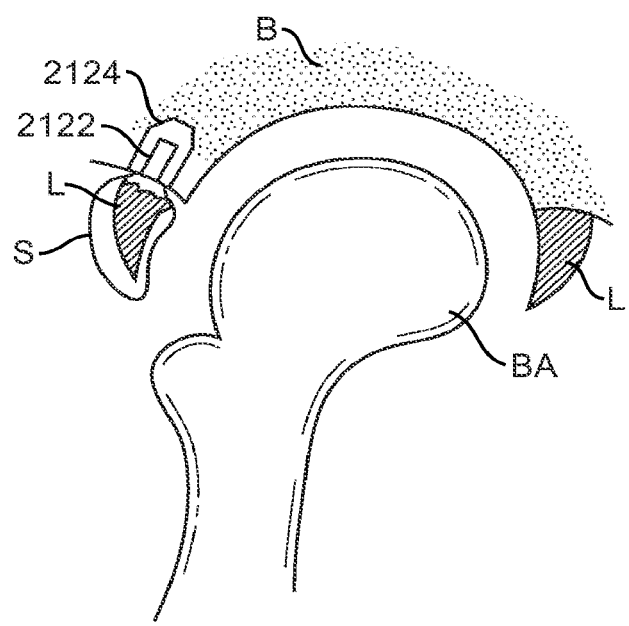

FIGS. 26A-26O illustrate another embodiment of a knotless suture anchor delivery system used to attach tissue to bone, especially useful for reattaching a torn labrum to the acetabulum. FIG. 26A illustrates a perspective view of an anchor delivery system 2100 which includes a suture anchor 2104 having an inner and outer anchor carried in a distal portion of outer shaft 2102.

Still referring to FIG. 26A, the suture may be carried inside the shaft or outside of the shaft and is not illustrated in this view. Outer shaft 2102 is sized to fit in an arthroscopic cannula for delivery through a portal into a joint space. Thus, as discussed above with respect to FIG. 6, the outer shaft preferably has a diameter of 5.4 mm or less so that it may easily fit in a typical arthroscopic cannula having an inner diameter of approximately 5.5 mm. Additionally, the working length of the outer shaft 2102 preferably is long enough to extend into a treatment region such as the acetabular socket and is preferably at least about 16.5 cm (6.5 inches) long. These dimensions may be applied to any of the delivery instruments disclosed in this specification when adapted for use in arthroscopic treatment of the hip. The proximal portion of the outer shaft 2102 includes a handle 2106 having an actuator mechanism 2108, 2110 for controlling the delivery system during various stages of anchor deployment.

FIG. 26B illustrates the inner 2122 and outer 2124 suture anchors in greater detail. Suture S is attached to outer anchor 2124 in a manner described more fully below. The suture is sized to be large enough to minimize the possibility of pulling through or tearing tissue and small enough to be secured to the inner and outer suture anchors. The suture then enters a central channel 2129 in inner anchor 2122 and is wrapped around a cinching mechanism 2135 and then a free end F exits the inner anchor. The cinching mechanism includes a radially deflectable arm 2134 that is integral with the inner suture anchor 2122. The arm 2134 has a hole 2136 to allow the suture to pass through the arm so that the suture is disposed on either side of the arm. Additional details on the suture anchor are disclosed below.

FIG. 26C is a cross sectional exploded view of a distal portion of the delivery instrument 2100 and anchor 2104 illustrating the inner shaft 2114, the intermediate shaft 2112 and the outer shaft 2102 of the delivery system as well as the inner anchor 2122 and the outer anchor 2124. The outer anchor 2124 has a tapered distal point 2116 adapted for penetrating bone. Outer anchor 2124 further includes a central channel 2126 for receiving the inner anchor 2122 and an annular recess 2128 acts as a locking mechanism for locking the inner anchor 2122 in the channel 2126. Resilient deflectable fingers or arms 2130 extend radially outward from the inner anchor and lock into the annular recess 2128. Other features such as slot 2132, and bore holes or channels 2120, 2121 are described in greater detail below.

FIG. 26D shows a cross section of the proximal region of the delivery system. In FIG. 26D, an inner shaft 2114 and an intermediate shaft 2112 are slidably disposed in outer shaft 2102. Handle 2106 includes a distal knob 2108 that is threadably engaged with the handle body 2106 and also operably coupled with outer shaft 2102. Thus, rotation of knob 2108 relative to the handle body 2106 will either advance or retract outer shaft 2102 relative to the inner shaft 2114 and the intermediate shaft 2112. Handle 2106 also includes a proximal knob 2110 that is threadably engaged with the handle body 2106 and also operably coupled with the inner shaft 2114. Rotation of knob 2110 relative to handle body 2106 will either advance or retract inner shaft 2114 relative to the intermediate shaft 2112 or the outer shaft 2108. One of skill in the art will appreciate that motion is relative, therefore either knob may be rotated relative to the handle or the handle may be rotated relative to a knob. Moreover, it will also be appreciated that other actuator mechanism known to those skilled in the art may be substituted for the rotating knobs, such as slider mechanisms or levers. FIG. 26E illustrates another cross sectional view of the proximal portion of the delivery system 2100 highlighting the handle and actuator mechanism. In FIG. 26E, actuation of knob 2110 has retracted the inner shaft 2114 relative to the intermediate shaft 2112 and the outer shaft 2102.

FIG. 26F illustrates a perspective view of a distal portion of delivery system 2100. Normally, during delivery anchor 2104 is enclosed entirely or almost entirely within shaft 2102 except with its distal point 2116 exposed. Once the delivery instrument has been advanced to a desired treatment site, the outer shaft 2102 is retracted, exposing the suture anchor 2104. The distal end of the anchor includes a tapered or pointed tip 2116 adapted to penetrate tissue such as bone. An elongate slot 2118 near the distal end of outer shaft 2102 allows the suture (not illustrated), which is attached to anchor 2104 as described below, to exit the shaft 2102 without tangling. The anchors are deployed in a direction parallel with the longitudinal axis of the delivery instrument. In some embodiments, the delivery instrument may be flexible, bendable, angled or articulated or it may be actively steerable in order to deliver the anchors at angles transverse to the longitudinal axis of the shaft 2102.

FIG. 26G illustrates a cross section of FIG. 26F and highlights the suture anchor which includes an outer anchor 2124 and an inner anchor 2122 partially disposed in a central channel 2126 of the outer anchor 2124. Additionally, the outer anchor 2124 includes a longitudinal bore hole 2121 and a transverse bore 2120 in its wall 2123 through which a suture may pass to allow a suture (not shown) to be fastened to the outer anchor. A plug may be used to create an interference fit locking the suture into the bore hole, or the suture may be bonded, tied, or otherwise fixed to the outer anchor. In a preferred embodiment, the suture is knotted at its end creating a ball that is larger than the longitudinal bore diameter, thereby securing the suture to the anchor. The distal end 2125 of intermediate shaft 2112 engages the outer anchor 2124 while the distal end of the inner shaft 2114 has a reduced diameter tip 2127 that fits within the central channel of inner anchor 2122.

FIG. 26H illustrates the outer anchor 2124 fully exposed from the outer shaft 2102. Once exposed, the outer anchor 2124 may be driven into the bone B or other tissue by exerting force on the handle 2106 or using any of the techniques previously described. Slot 2132 in intermediate shaft 2112 allows the suture (not shown), which is coupled to the inner and outer anchors, to exit the shaft 2112 without tangling or binding with other components. After deployment of outer anchor 2124 the inner anchor 2122 remains in shaft 2102, separated from outer anchor 2124 with a suture (not shown) coupled therebetween.

In some embodiments, the delivery instrument and anchors may have a central channel that extends the entire length of the device. This central channel is used to accommodate a drill bit or other drilling device (e.g. water jet or laser) which can be used to drill a pilot hole in the bone and facilitates placement of the anchor into the bone. Thus, the system may further include a drilling system such as a mechanical drill, a laser drill, water jet drill or other drilling mechanisms for creating the pilot hole. In some embodiments, the inner and intermediate shafts of the delivery instrument along with anchor 2104 may be removed and replaced with the drilling system and thus the outer shaft serves as a guide for drilling. Once the pilot hole has been created, keeping the outer shaft in place against the bone, the drill is removed and the interior shafts and suture anchor are replaced in the outer shaft to deliver the suture anchor into the drilled hole.

In FIG. 26I, once the outer anchor 2124 has been driven into bone B, the suture S may be looped around target tissue to be captured (e.g. a torn labrum in the hip or shoulder joint) and the inner anchor advanced relative to the outer shaft 2102. One end of the suture S is attached to the outer anchor 2124 and another portion of the suture is coupled with the inner anchor 2122 (as described below). A free end F may be pulled to adjust the length of suture between the inner and outer anchors, as well as allowing adjustment of suture tension. The suture may run freely alongside the outer shaft or in some embodiments the outer shaft may include suture management features on its exterior such as grooves, channels, eyelets, clips or other features which hold the suture temporarily to keep the suture from tangling or knotting. In still other embodiments, the suture may remain inside the outer shaft of the delivery instrument and the suture may be threaded through one or more lumens therein.

FIG. 26J illustrates the inner anchor 2122 fully exposed from the outer shaft 2102. In this exemplary embodiment, the inner anchor 2122 has a blunt distal end and is inserted into and locked with outer anchor 2124. However, inner anchor 2122 may also have a tapered or pointed tip similar to outer anchor 2124 thereby inner anchor 2122 may be adapted to penetrate tissue such as bone or soft tissue. Thus the inner anchor may be adapted to be driven directly into bone at a location apart from the outer anchor. Advantageously, in such embodiments, the operator has the option of either coupling the inner anchor 2122 to the outer anchor 2124 or driving the inner anchor into bone at another location prior to cinching the suture to the appropriate level of tension.

FIG. 26K shows the inner anchor 2122 released from the inner shaft 2114, although in use, the inner anchor 2122 would not be detached from the inner shaft 2114 until it is either locked with the outer anchor 2124 or driven into bone. FIG. 26L is a cross section similar to that of FIG. 26C, except the inner, intermediate and outer shafts 2102, 2112, 2114 have been shaded for ease of viewing. FIG. 26M shows both the inner 2122 and the outer 2124 anchors released from the delivery instrument 2100 and the inner anchor 2122 is locked in the central channel of the outer anchor 2124.

Referring back to FIG. 26B, the inner 2122 and outer 2124 suture anchors are illustrated in greater detail. Suture S is attached to outer anchor 2124. The suture then enters a central channel in inner anchor 2122 and is wrapped around the cinching mechanism and then a free end F exits the inner anchor. The cinching mechanism includes a radially deflectable arm 2134 that is integral with the inner suture anchor 2122. The arm 2134 has a hole 2136 to allow the suture to pass through the arm so that the suture is disposed on either side of the arm. Additionally, a plurality of resilient fingers 2130 are disposed circumferentially around the inner anchor and are adapted to snap into the annular recess 2128 in outer anchor 2124 (seen in FIG. 26N) to lock the inner and outer anchors together. In some embodiments, the proximal end of the central channel 2126 in outer anchor 2124 may be chamfered or have a bevel to facilitate receipt of the inner anchor. The outer diameter of the outer suture anchor is preferably less than 4 mm, more preferably less than about 3.5 mm so that it is not excessively large as compared to the area typically available on the acetabular rim. Of course, other diameters may also be used depending on where the anchor is to be placed. Additionally, the length of the outer anchor is also sized so that it will not penetrate through the acetabular rim into the articular surface of the joint, preferably being at least about 5 mm and no more than about 14 mm. The central channel is sized to receive the inner anchor, which may be about 1-3 mm in diameter in exemplary embodiments. These dimensions are extremely small and difficult to machine thus it is only recently with the advent of laser cutting and electrical discharge machining (EDM) as well as the construction of each of the inner and outer anchors as a single integral structure that such small components could be reliably manufactured to acceptable engineering tolerances. Moreover, such small scale components have not traditionally been used due to the risk of failure in service, but is now possible due to better biocompatible engineering materials and improved manufacturing capabilities.

Outer anchor 2124 optionally may also have outer surface features that help secure it to tissue such as bone. For example, anchor 2124 may have wings similar to cutouts 1003 in FIGS. 15A-15D or similar to the resilient deflectable arms 2130 on the inner anchor, which help secure the anchor when placed below the cortical shell of bone. The wings deflect radially inward as the anchor is being placed into bone, and then the wings have sufficient resilience to radially expand outward once the anchor is positioned. In alternative embodiments, the wings may be forced radially outward by engagement with the inner anchor as the inner anchor is inserted into the outer anchor. In still other embodiments, ribs, barbs, bumps, ridges, grooves, channels or other surface features may also be machined or added to the outer surface to help mechanically secure the anchor to bone or to promote tissue ingrowth. The outer anchor is capable of resisting a pullout force at least as large as the force required to tear tissue such as the labrum. In preferred embodiments, the outer anchor pullout force has a safety margin and thus it can resist a pullout force at least 1.5 times greater than the force required to tear tissue such as the labrum. In exemplary embodiments the pull out force of the anchor is about 20-80 lbs.

FIG. 26N is a cross section of FIG. 26B showing how the cinching mechanism works. The suture S may be any commercially available suture of suitable size and strength, either braided or not, and may be free of knots, or other features to interact with arm 2134 and be effectively clamped thereby. In FIG. 26N, suture is attached to outer anchor 2124 by disposing the suture in bore holes 2121 and 2120. The suture may then be tied, bonded, plugged or otherwise attached to the outer anchor within transverse hole 2120. The suture extends into the central channel 2129 in inner anchor 2122 and around the distal end 2131 of deflectable arm 2134, through aperture 2136 and the free end F exits the inner anchor. An aperture 2140 in the sidewall of inner anchor 2122 creates an edge 2142 in the sidewall, the suture is pinched between arm 2134 and the edge 2142 on the inner wall of the inner anchor. In some embodiments, the distal end of arm 2134 may have a groove, a curved tip or a forked tip to help keep the suture centered on the arm 2134. In embodiments having this feature, the aperture 2140 will be fabricated to have a complementary shape to maintain a sharp edge for pinching the suture against the grooved, curved or forked region of the arm 2134.

Thus, once both anchors have been secured and the target tissue captured by the suture, the free end F may be pulled through the cinching mechanism. As the free end F of the suture is pulled, the arm 2134 deflects outward (toward the sidewall of channel 2129 to which arm 2134 is attached), allowing the suture to pass through the cinching mechanism without being constrained. On the other hand, when the suture is pulled in the opposite direction, the suture will deflect arm 2134 radially toward the opposite sidewall of channel 2129, pinching the suture between the distal end 2131 of arm 2134 and the inner wall of the inner anchor, locking the suture in tension between the inner and outer anchors. Thus, the cinching mechanism allows the suture to move through the inner anchor in one direction without slipping in the opposite direction. Advantageously, the suture is locked without need for the operator to manually actuate a locking mechanism on the anchor. The cinching mechanism is capable of holding the suture and resisting a pullout force at least as large as the force required to tear tissue such as the labrum. In preferred embodiments, the cinching mechanism has a safety margin built into it and thus it can resist a suture pullout force at least 1.5 times greater than the force required to tear tissue such as the labrum. In exemplary embodiments, the cinching mechanism 2135 in the inner anchor is preferably capable of withstanding tension of 20-80 lbs on the suture S without allowing the suture to slip.

It should be noted that the cinching mechanism may alternatively be provided on the outer anchor 2124 with the suture being fixed to the inner anchor 2122, or cinching mechanisms may be provided on both anchors. For example, a cinching mechanism like that described above may be provided in channel 2121 of outer anchor 2124.

The delivery system 2100 may be used to secure torn tissue to a bone. For example, in FIG. 26O, a torn labrum L is reattached to the glenoid or acetabular rim in a shoulder or hip joint Inner and outer suture anchors 2122, 2124 are driven into the bone B and suture coupled with the anchors captures the torn labrum L. This helps to ensure that the mating bone BA (e.g. femoral or humeral head) will not disengage from the socket during movement of the joint.

Figure 27A:
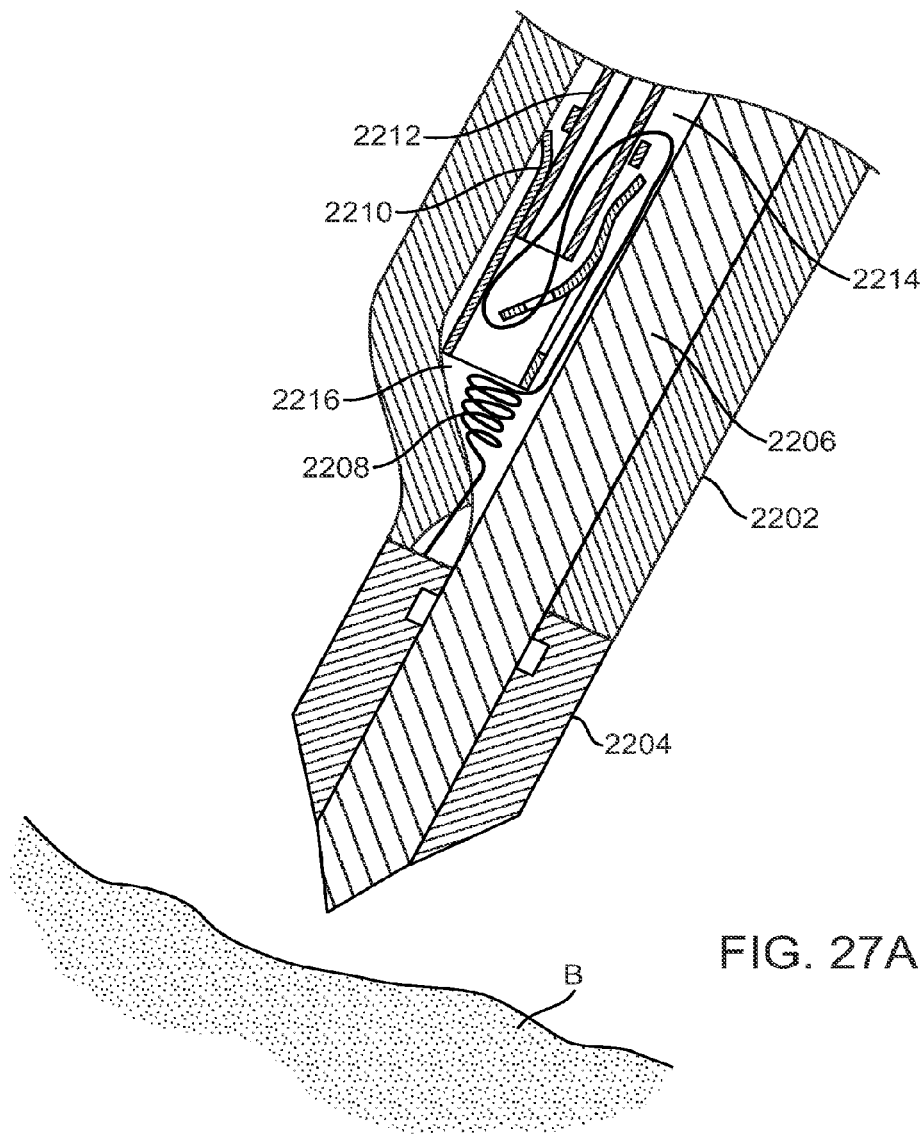
FIGS. 27A-27D illustrate another embodiment of a suture anchor system.
Figure 27B:
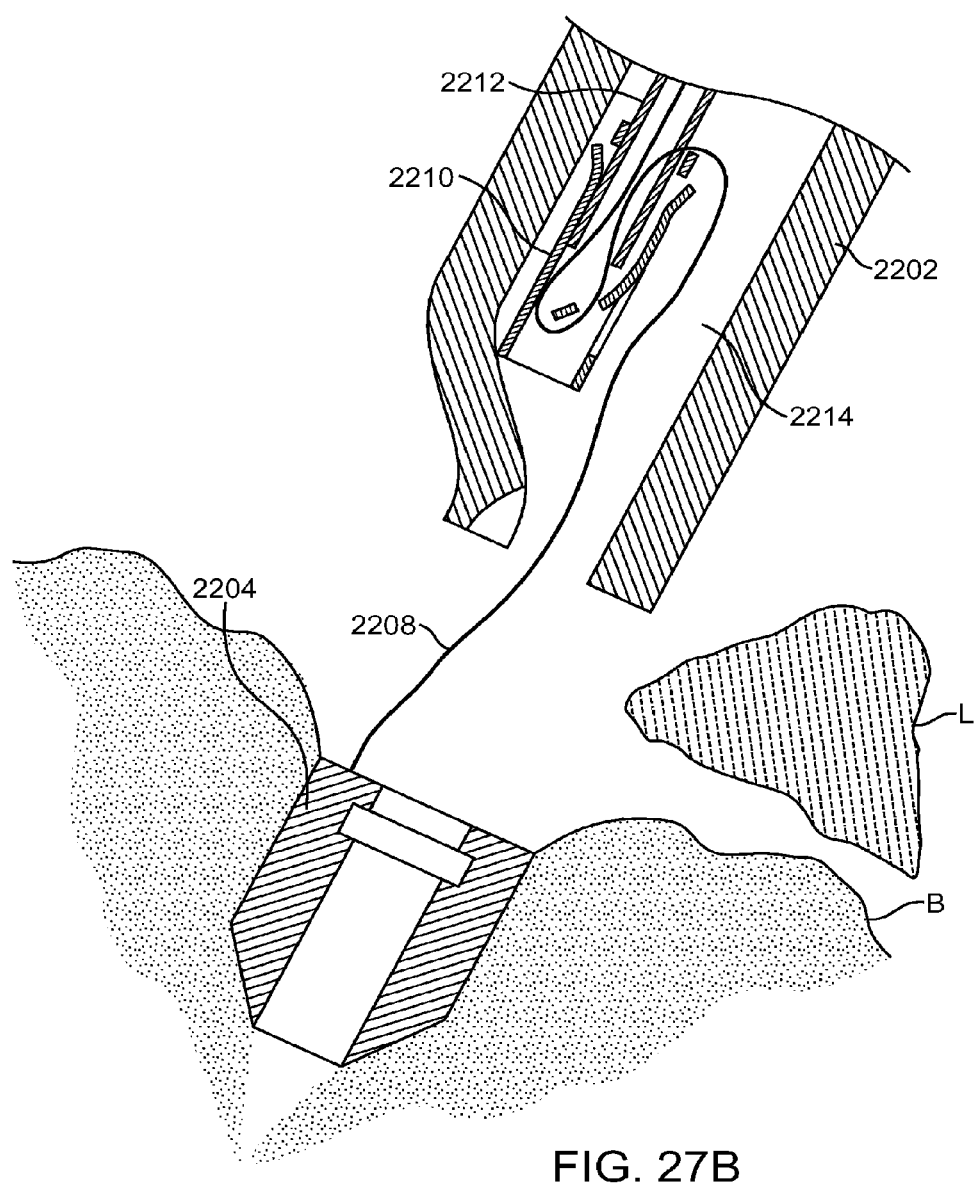
Figure 27C:
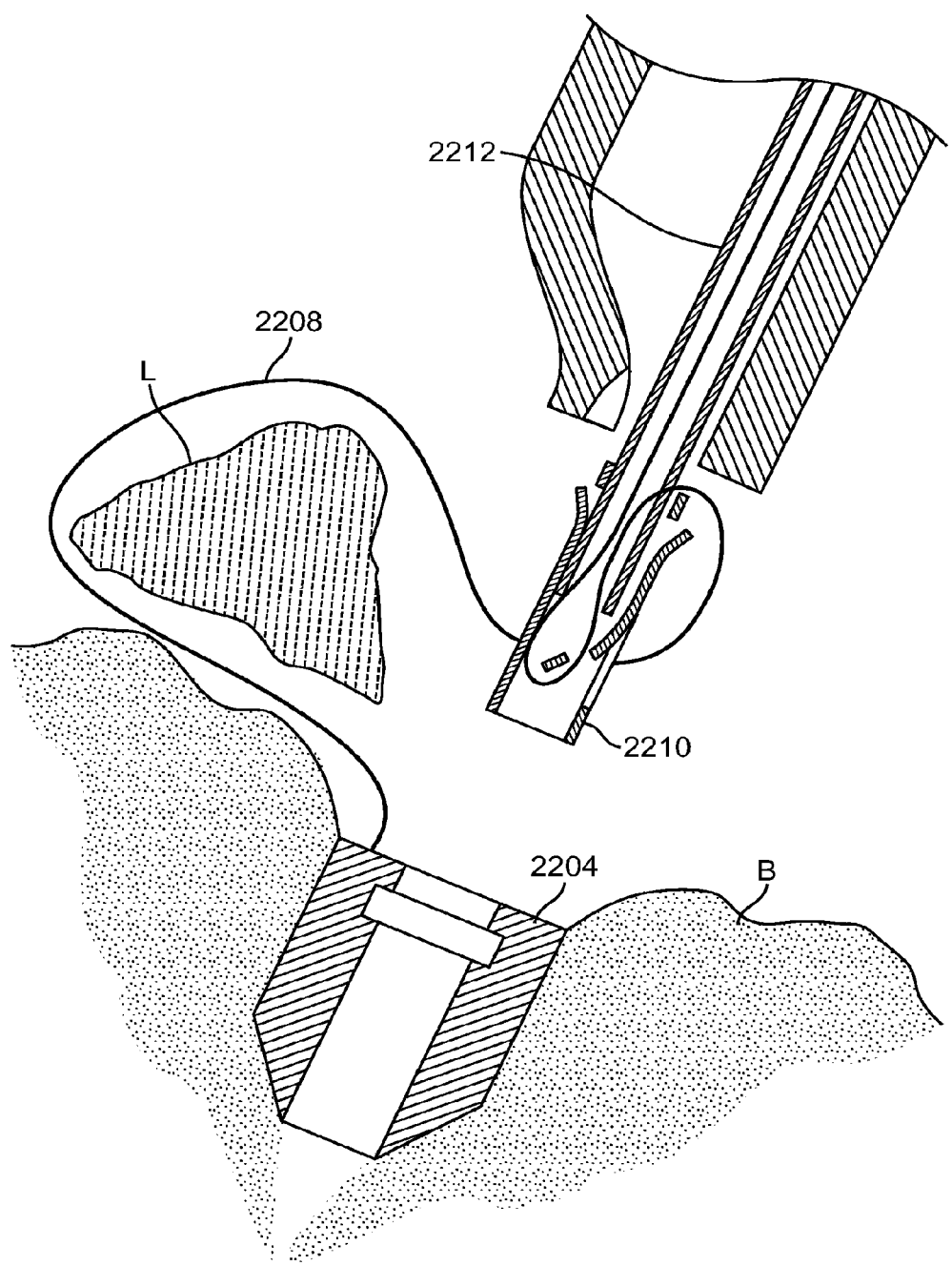
Figure 27D:
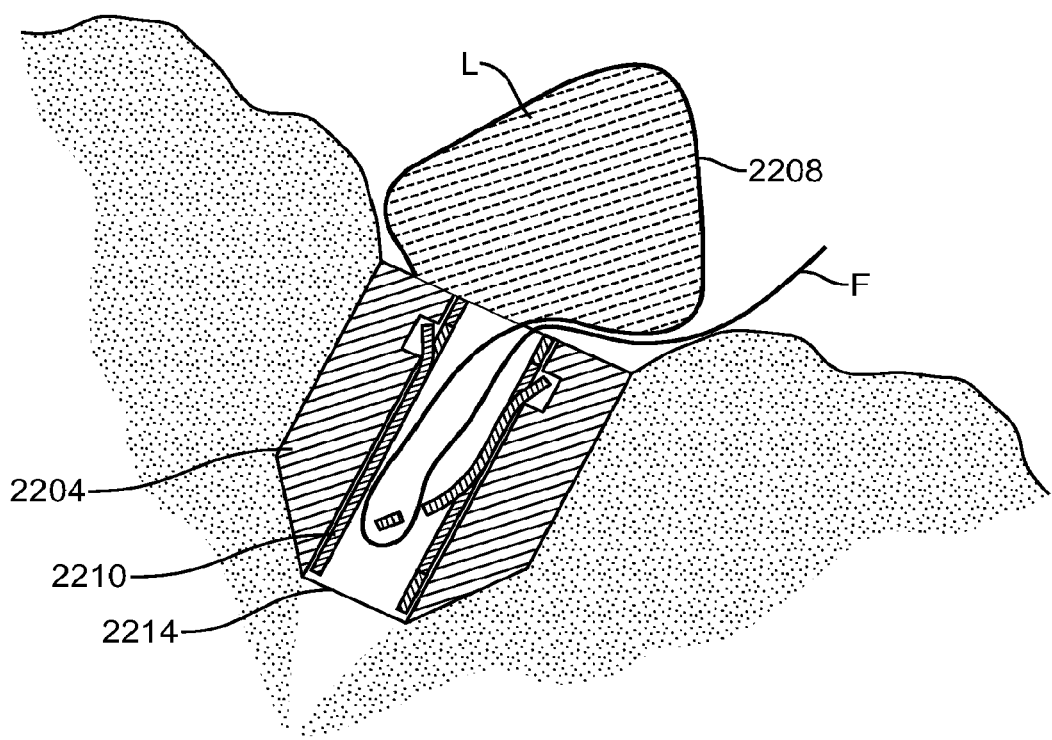

FIGS. 27A-27D illustrate another embodiment of an anchor delivery system. The anchor of this embodiment is similar to the previous embodiment, except that the inner anchor and the outer anchor are held side by side in the same or separate channels in the delivery instrument, whereas in the previous embodiment the two anchors are held end to end. In FIG. 27A, an outer shaft 2202 houses an outer suture anchor 2204 in a main channel 2214, an inner suture anchor 2210 and a length of suture 2208 in a side channel 2216. The suture 2208 is coupled with both inner and outer anchors. The outer anchor 2204 is held near the distal end of the main channel 2214 and a first driving mandrel 2206 can be used to drive the outer anchor 2204 into the bone B. The driving mandrel may be actuated using any of the techniques disclosed herein, including direct mechanical impaction, or by pneumatic, hydraulic, ultrasonic or other means. Once the outer anchor has been driven into the bone, the first driving mandrel 2206 is retracted as illustrated in FIG. 27B. A flexible second driving mandrel 2212 is then advanced either actively or by a spring in order to move the inner suture anchor 2210 distally into the main channel 2214. A curved portion near the distal end of the side channel moves the inner suture anchor 2210 into the main channel 2214. Target tissue such as a torn labrum L may be captured by looping the suture 2208 around the tissue as seen in FIG. 27C. FIG. 27D shows that the inner suture anchor 2210 is then driven by the second driving mandrel 2212 into the first suture anchor 2204 where the two anchors lock together using a locking mechanism similar to that previously described, or using detent mechanisms or other locking mechanisms known in the art. The free end F of the suture is then pulled in order to tension the suture so that that the torn tissue properly engages the bone. This allows the torn tissue to heal and reattach to the bone. Any of the clamping, locking or cinching mechanisms described above may be used to tension the suture in this embodiment.

Figure 28A:
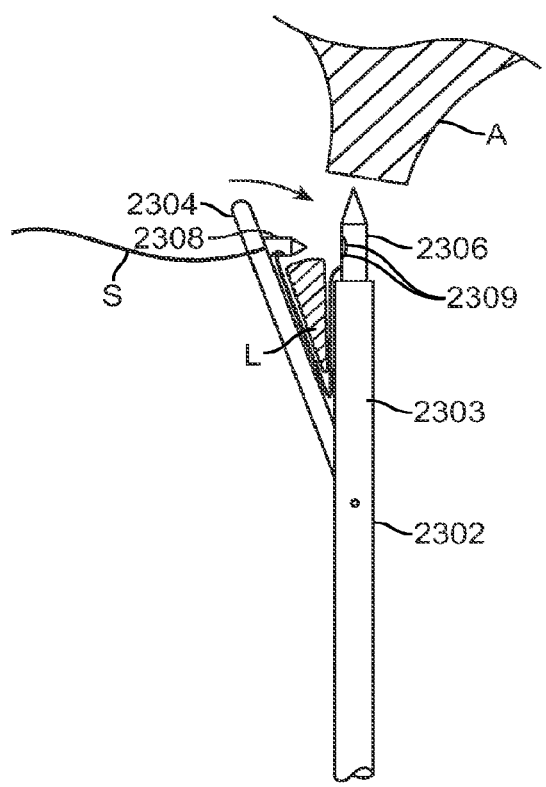
FIGS. 28A-28C illustrate still another embodiment of a suture anchor system.
Figure 28B:
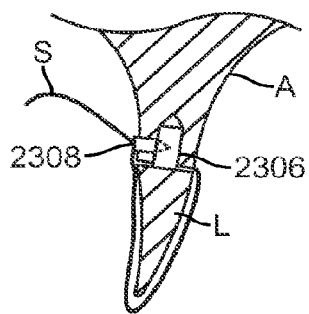
Figure 28C:
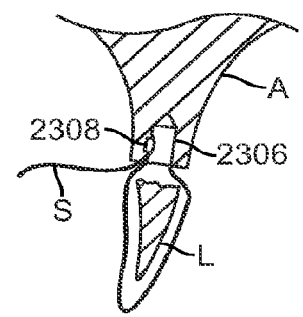

FIGS. 28A-28C illustrate another embodiment of a suture anchor delivery system. This embodiment uses jaws to help capture the damaged tissue and also to help insert an inner suture anchor into an outer suture anchor. In FIG. 28A, the delivery instrument 2302 includes an arm 2304 that is pivotably connected with the main shaft 2303 of the delivery instrument, thereby forming a jaw. The arm 2304 holds the inner suture anchor 2308 and the main shaft holds the outer anchor 2306 such that the inner anchor 2306 is aligned with aperture 2309 in the sidewall of outer anchor 2306 thereby being moved transverse to the longitudinal axis of outer anchor 2306. A suture S is coupled to both anchors. In FIG. 28A, the delivery instrument is advanced to the treatment site and the jaw captures the damaged tissue, here a torn labrum L. The suture is disposed between the torn tissue and the jaw. Once the damaged tissue is captured, the outer anchor 2306 may be driven into the bone, here the rim of the acetabulum A in a hip joint. Then the inner anchor 2308 is driven through a lateral wall of the bone A into the receiving aperture 2309 in the outer anchor where the two anchors lock together as shown in FIG. 28B. The tension in the suture is then adjusted using any of the cinching mechanisms described above. In alternative embodiments, the inner anchor 2308 is snapped and locked into a receiving aperture of the outer anchor 2306 first, then the combined anchor is driven into the acetabular rim A as shown in FIG. 28C. The suture is then tensioned as before. In both embodiments, both the inner and outer suture anchors are driven into the bone or into one another so that they are flush with the outer surface of the bone.

Figure 29A:
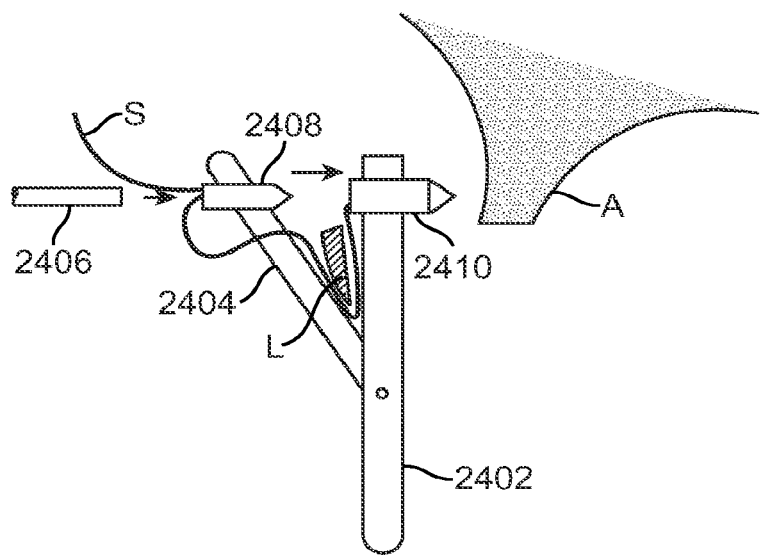
FIGS. 29A-29E illustrate yet another embodiment of a suture anchor system.
Figure 29B:
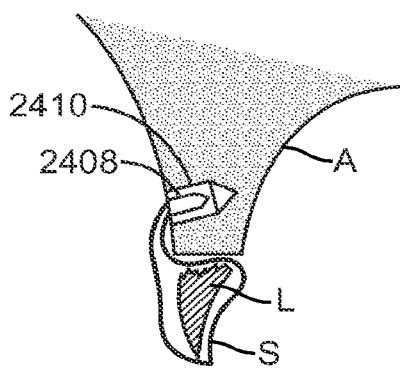
Figure 29C:
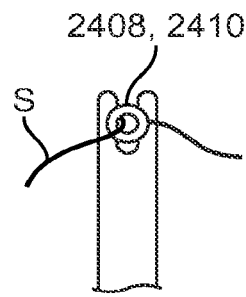
Figure 29D:
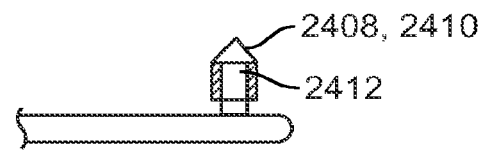
Figure 29E:
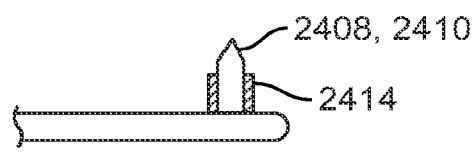

FIGS. 29A-29B illustrate an embodiment similar to the previous embodiment with the major difference being that the inner anchor is inserted substantially parallel into the outer anchor, unlike the previous embodiment where insertion of the inner anchor is transverse to the outer anchor. In FIG. 29A, a delivery instrument 2402 has a main shaft and an arm 2404 pivotably coupled to the main shaft, forming a jaw. The arm 2404 carries the inner anchor 2408 and the main shaft carries the outer anchor 2410. The instrument is advanced to the treatment site and the tissue to be repaired, here labral tissue L, is captured within the jaw. Suture is coupled to both anchors and is disposed between the labrum L and the jaw. The inner anchor 2408 is coupled to the outer anchor 2410 by moving jaw 2404. Then the combined inner and outer anchors are driven into the bone using a separate driver 2406 inserted through a separate portion in a direction substantially parallel to the longitudinal axis of the anchors. In FIG. 29B, the suture is tensioned using any of the cinching mechanisms described above, thereby apposing the labrum with the acetabular rim A. FIG. 29C shows that in some embodiments, either the jaw or the main shaft may be forked in order to hold the inner 2408 or the outer 2410 anchor while allowing the anchor to be easily slipped off after placement. Alternatively, either arm of the jaw may have a gripping feature that frictionally engages either the inner diameter or the outer diameter of the anchor. For example, in FIG. 29D a central post 2412 holds the anchor, while in FIG. 29E, a tube 2414 grasps the outer surface of an anchor.

Figure 30:
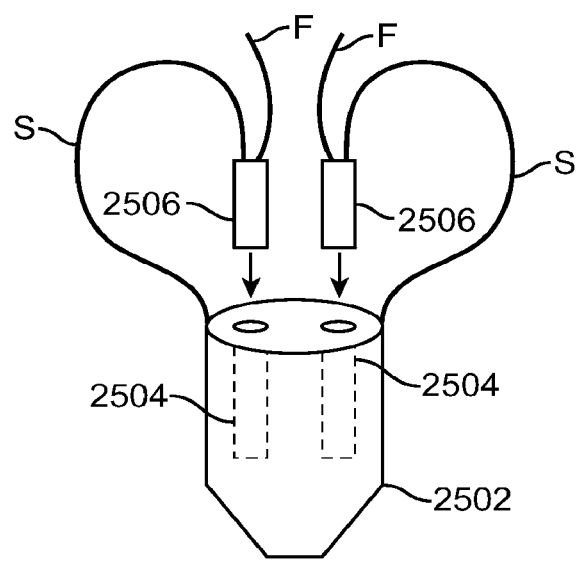
FIG. 30 illustrates an embodiment of a suture anchor having two sutures.

The embodiments disclosed above may easily be modified in order to accommodate more than one suture and/or more than one anchor. For example, in FIG. 30, an outer suture anchor 2502 has two channels 2504 that are sized to receive two inner anchors 2506. Thus, in this embodiment, two sutures S, each having a free end F, may be anchored to a single outer anchor. The same anchor may also be used for three, four, five, six, or more sutures. The inner anchors may be configured much like those described above with suture cinching or locking mechanisms.

Figure 31:
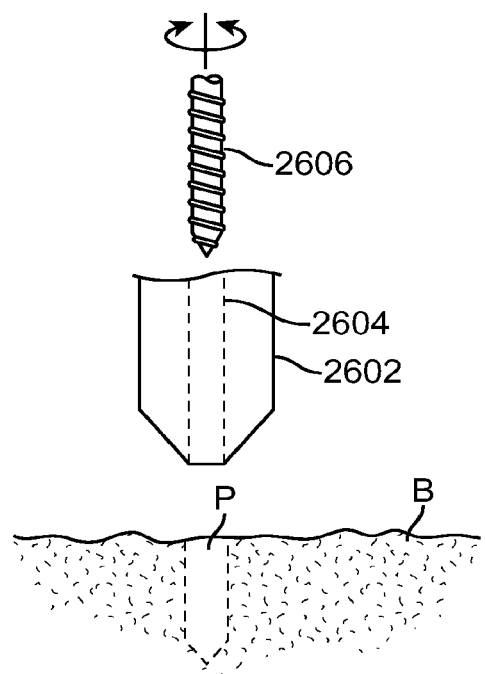
FIG. 31 illustrates an embodiment of a suture anchor that accommodates a pilot hole drill.

The suture anchors may be driven directly into bone or in some situations, it may be desirable to drill a pilot hole to help receive the anchor. For example, in FIG. 31, the central channel 2604 in the outer anchor 2602 that receives the inner anchor may extend all the way through the outer anchor. Thus, the central channel may also allow a pilot hole drill 2606 to pass through the outer anchor and drill a pilot hole P in the bone. The pilot hole allows the outer anchor to more easily be driven into the bone. As described above, the pilot hole drill may be a mechanical drill, laser, or water jet, and may be adapted for placement through the instrument that delivers the anchor.

Figure 32A:
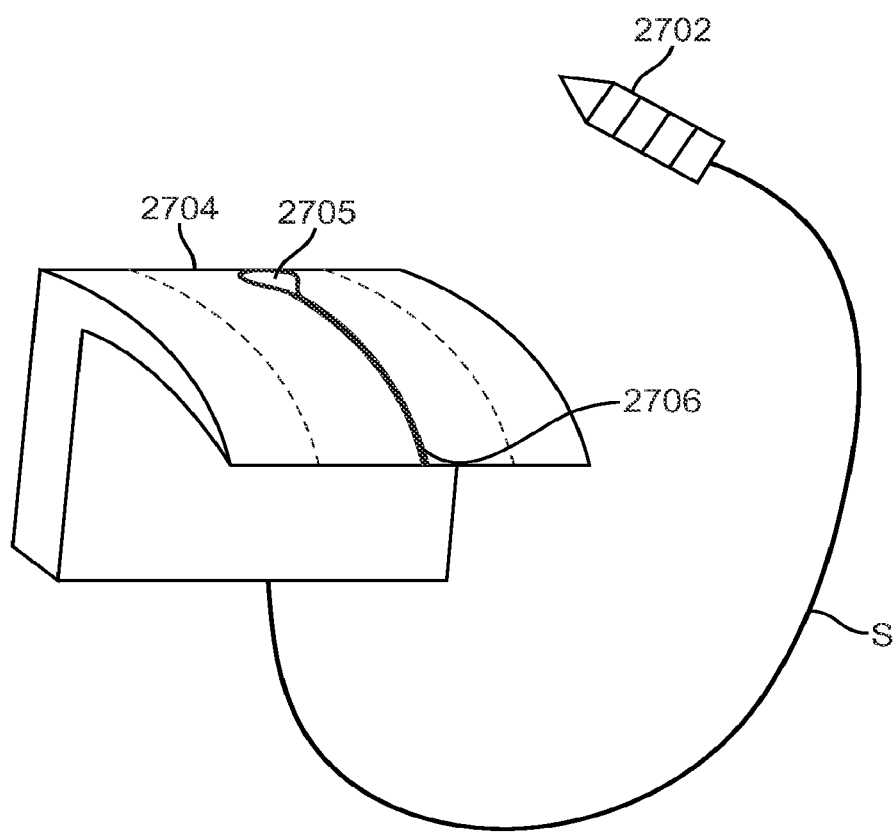
FIGS. 32A-32C illustrate another embodiment of a suture anchor system.
Figure 32B:
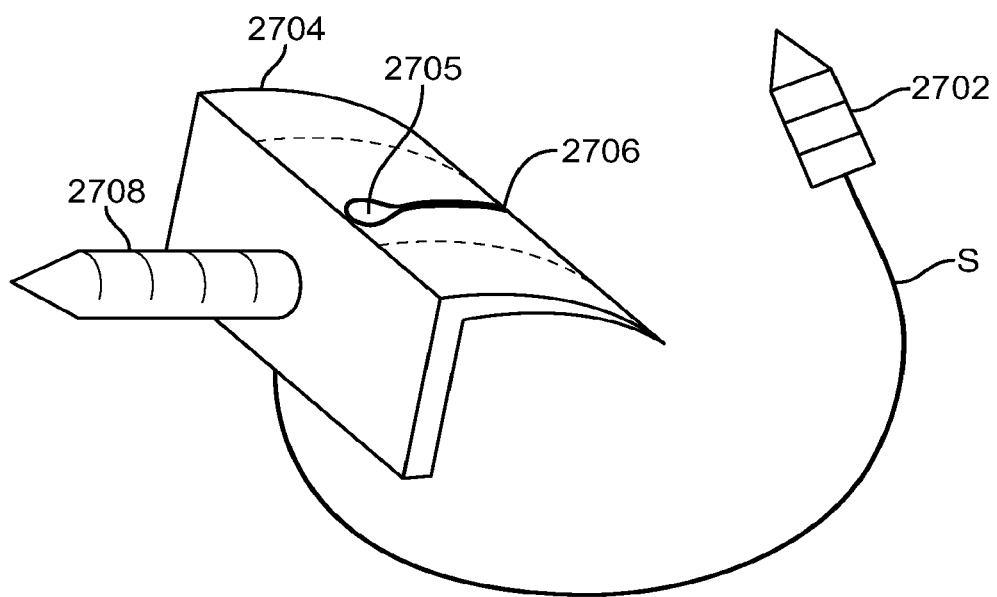
Figure 32C:
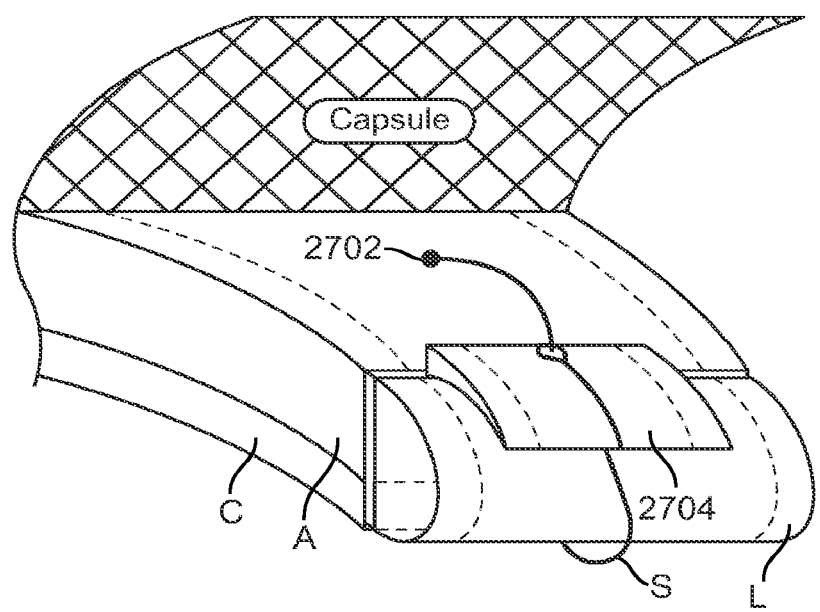

FIGS. 32A-32C illustrate another embodiment of a suture anchor system that may be used to help reattach a torn labrum to the acetabular or glenoid rim. In FIG. 32A, the anchor system includes a first pin 2702 or screw, adapted for penetrating tissue and anchoring in bone, and an L-shaped flexible anchor bracket 2704 having a curvature that conforms to the anatomy of the acetabular rim and also to a torn labrum. A suture S is coupled to both the pin 2702 and the bracket 2704. The bracket has a slit 2706 sized to receive the suture preferably with an enlarged opening 2705 at its inner closed end. FIG. 32B illustrates the back end of the bracket 2704 which has an anchoring pin 2708 or screw for attachment to bone or other tissue. FIG. 32C illustrates use of the system where the bracket 2704 is fixed to the acetabular or glenoid rim A and extends around an edge of the torn tissue, here the labrum L. After attachment of bracket 2704 to rim A, the suture S is wrapped under the torn tissue capturing it in a loop and the suture is then inserted into the slit 2706 closing the suture loop. The pin 2702 is then attached to the bone, here the actetabular rim A of a hip joint having a surface of cartilage. Pin 2702 or bracket 2704 may include any of the cinching mechanisms described above such that the suture may be tensioned and locked. The bracket helps support the torn tissue and also helps to prevent it from everting. Any part of the system may include therapeutic agents to help the labrum reattach to the bone and also the surface of the bracket may be coated or modified to encourage tissue ingrowth. Bracket 2704 is preferably a porous flexible material such as Dacron mesh, PTFE or other polymer to encourage ingrowth of tissue but having sufficient rigidity and resilience to support the labrum and allow some movement thereof. In some embodiments, the bracket may be reinforced with wires, fibers or other materials to give it additional strength or shape. In addition, bracket 2704 or anchoring pin 2708 may be adapted to couple with first pin 2702 in a coupling mechanism similar to those described above.

Figure 33:
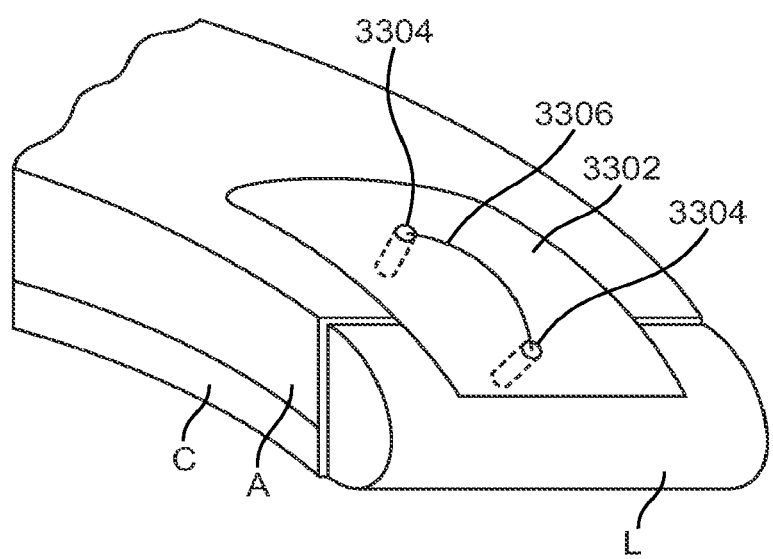
FIG. 33 illustrates another embodiment of a suture anchor system.

FIG. 33 illustrates an alternative embodiment of a suture anchor system used to reattach torn tissue to a bone. In FIG. 33, a generally flat bracket 3302 is used to join the torn labrum L to the acetabular rim A having a cartilage surface C. Pins or screws 3304 are used to secure one end of the bracket 3302 to the bone and the other end of the bracket to the labrum L. A suture 3306 may be coupled to the pins 3304 and used to adjust tension thereby approximating the torn labrum L with the rim A. The pins may be sharp pins or any of the anchor embodiments disclosed above. Alternatively, in place of pin 3304, a suture may be attached to bracket 3302 with a pin or other coupling member on its free end adapted for coupling back to bracket 3302 or to pin 3304, or for driving into bone. In alternative embodiments, the bracket may be designed to clip onto the labrum and/or the acetabular rim and therefore one or both pins may be optional. The bracket generally has similar properties as described above with respect to bracket 2704, and any of the cinching mechanisms disclosed herein may be incorporated into one or both pins in order to tension the suture.

While the above is a complete description of the preferred embodiments of the invention, various alternatives, modifications, and equivalents may be used. The various features of the embodiments disclosed herein may be combined or substituted with one another. Therefore, the above description should not be taken as limiting in scope of the invention which is defined by the appended claims.

What is claimed is:

1. A method of knotless suturing comprising:
   providing a delivery instrument carrying a first anchor and a second anchor, wherein a continuous length of suture is coupled directly with the first anchor and directly with the second anchor;
   advancing the delivery instrument to a treatment region comprising treatment tissue;
   placing the first anchor into a first region of the tissue;
   coupling the suture to a portion of the treatment tissue;
   attaching the second anchor to the first anchor;
   tensioning the suture; and
   securing the suture without knotting the suture by moving the suture through a cinching mechanism in the first or the second anchor, wherein the cinching mechanism is adapted to allow the suture to move through the cinching mechanism in a first direction while movement of the suture through the cinching mechanism in a second direction opposite the first direction is constrained independently of the position of the second anchor relative to the first anchor.

2. The method of claim 1, wherein the second anchor is stationary relative to the first anchor during the entire step of securing the suture.

3. The method of claim 1, wherein the tissue comprises bone and placing the first anchor comprises drilling a pilot hole into the bone, the pilot hole sized to receive the first or the second anchor.

4. The method of claim 1, further comprising deflecting a distal portion of the delivery instrument.

5. The method of claim 1, wherein the first region of tissue comprises the acetabulum and the treatment tissue comprises an acetabular labrum.

6. The method of claim 1, wherein attaching the second anchor to the first anchor comprises inserting the second anchor into a central channel of the first anchor and locking the two anchors together to prevent axial movement of the first anchor relative to the second anchor.

7. The method of claim 1, wherein the delivery instrument further comprises an actuator mechanism near a proximal end of the instrument and placing the first anchor comprises actuating the actuator mechanism to expose the first or the second anchor from the delivery instrument.

8. The method of claim 1, wherein securing comprises clamping the suture between a deflectable arm and an inner wall of the first or the second anchor.

9. The method of claim 8, wherein the arm is integral with either the first or the second anchor.

10. The method of claim 1, wherein attaching comprises placing the second anchor in a central channel within the first anchor.

11. The method of claim 10, wherein the cinching mechanism is disposed in an inner channel of the second anchor.

12. The method of claim 1, wherein the delivery instrument has a longitudinal axis, and wherein placing the first anchor comprises placing the first anchor into the first region at an angle transverse to the longitudinal axis of the delivery instrument.

13. The method of claim 1, wherein attaching the second anchor to the first anchor comprises actuating a jaw disposed on the delivery instrument.

* * * * *